United States Patent
Lyte et al.

(10) Patent No.: US 11,357,803 B2
(45) Date of Patent: Jun. 14, 2022

(54) PROBIOTIC COMPOSITIONS FOR PRODUCTION OF DOPAMINE

(71) Applicant: Iowa State University Research Foundation, Inc., Ames, IA (US)

(72) Inventors: Mark Lyte, Ames, IA (US); Daniel Nicholas Villageliu, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 88 days.

(21) Appl. No.: 16/649,016

(22) PCT Filed: Sep. 21, 2018

(86) PCT No.: PCT/US2018/052128
§ 371 (c)(1),
(2) Date: Mar. 19, 2020

(87) PCT Pub. No.: WO2019/060661
PCT Pub. Date: Mar. 28, 2019

(65) Prior Publication Data
US 2020/0297784 A1 Sep. 24, 2020

Related U.S. Application Data

(60) Provisional application No. 62/561,745, filed on Sep. 22, 2017.

(51) Int. Cl.
*A61K 35/744* (2015.01)
*A61K 9/00* (2006.01)
(Continued)

(52) U.S. Cl.
CPC .......... *A61K 35/744* (2013.01); *A61K 9/0053* (2013.01); *A61K 31/198* (2013.01); *A61K 31/675* (2013.01)

(58) Field of Classification Search
CPC .. A61K 9/0053; A61K 35/741; A61K 35/744; A61K 31/675; A61K 31/198;
(Continued)

(56) References Cited

U.S. PATENT DOCUMENTS 8,771,675 B2 7/2014 Zink et al.
9,399,048 B2 7/2016 Tsai et al.
(Continued)

FOREIGN PATENT DOCUMENTS

DE 10206995 A1 * 9/2003 ........... A23L 33/135
DE 10206995 A1 9/2003
(Continued)

OTHER PUBLICATIONS

Barrett et al., "γ-Aminobutyric acid production by culturable bacteria from the human intestine", Journal of Applied Microbiology, vol. 113, pp. 411-417, May 10, 2012.
(Continued)

*Primary Examiner* — Jana A Hines
(74) *Attorney, Agent, or Firm* — McKee, Voorhees & Sease, PLC

(57) ABSTRACT

The present invention is directed to synbiotic compositions of probiotic strains and prebiotics, along with uses thereof for targeted human and animal applications, for example, in promoting health and well-being and/or treating therapeutic conditions. The present invention is also directed to methods of probiotic selection and detection of strains with the ability to produce neurochemicals in the gastrointestinal tract of a subject, providing a microbial endocrinology-based mechanism and approach for optimization of synbiotic delivery of a probiotic with a neurochemical precursor. Still further the present invention is directed to industrial applications for production of dopamine utilizing methods and media suitable for the same.

12 Claims, 29 Drawing Sheets

(51) Int. Cl.
*A61K 31/198* (2006.01)
*A61K 31/675* (2006.01)

(58) Field of Classification Search
CPC ...... A61K 45/06; A61K 2300/00; C12Q 1/02; G01N 2500/10
USPC .......... 424/9.1, 9.2, 93.1, 93.4, 234.1, 278.1
See application file for complete search history.

(56) References Cited

U.S. PATENT DOCUMENTS

| | | | |
|---|---|---|---|
| 9,427,000 | B2 | 8/2016 | Boileau et al. |
| 9,580,680 | B2 | 2/2017 | Boileau et al. |
| 2006/0165822 | A1 | 7/2006 | Van Der Giessen et al. |
| 2008/0171106 | A1 | 7/2008 | Zink et al. |
| 2014/0301995 | A1 | 10/2014 | Mayra-Makinen et al. |
| 2015/0250833 | A1 | 9/2015 | Rubio Nistal et al. |
| 2016/0058808 | A1 | 3/2016 | Hsiao et al. |
| 2016/0129057 | A1 | 5/2016 | Jeon et al. |
| 2017/0184569 | A1 | 6/2017 | Keshavarzian et al. |

FOREIGN PATENT DOCUMENTS

| | | |
|---|---|---|
| JP | 55102394 A | 8/1980 |
| WO | 2016113363 A1 | 7/2016 |

OTHER PUBLICATIONS

Derrien et al., "Mucin-bacterial interactions in the human oral cavity and digestive tract", Gut Microbes, vol. 1:4, pp. 254-268, Jul. 2010.

EFSA, "Scientific Opinion on the safety and efficacy of Oralin (Enterococcus faecium) as a feed additive for calves for rearing, piglets, chickens for fattening, turkeys for fattening and dogs; EFSA Panel on Additives and Products or Substances used in Animal Feed (FEEDAP)", EFSA Journal, vol. 12(6), 19 pages, Feb. 20, 2015.

Galland, Leo, "The Gut Microbiome and the Brain", Journal of Medicinal Food, vol. 17(12), pp. 1261-1272, Oct. 9, 2014.

Gibson et al., "Use of a Three-Stage Continuous Culture System to Study the Effect of Mucin on Dissimilatory Sulfate Reduction and Methanogenesis by Mixed Populations of Human Gut Bacteria", Applied and Environmental Microbiology, vol. 54, No. 11, pp. 2750-2755, Nov. 1988.

Hemarajata et al., "Effects of probiotics on gut microbiota: mechanisms of intestinal immunomodulation and neuromodulation", Therapeutic Advances in Gastroenterology, vol. 6(1), pp. 36-51, 2013.

Leung et al., "Effects of porphyrins and inorganic iron on the growth of Prevotella intermedia", FEMS Microbiology Letters, vol. 209, pp. 15-21, Jan. 3, 2002.

Lyte, Mark, "Probiotics function mechanistically as delivery vehicles of neuroactive compounds: Microbial endocrinology in the design and use of probiotics", Bioessays, vol. 33, pp. 574-581, 2011.

Mackie et al., "InfoGest Consensus Method", the Impact of Food Bioactives on Health, Chapter 2, pp. 13-22, 2015.

Marques et al., "Simulated Biological Fluids with Possible Application in Dissolution Testing", Dissolution Technologies, pp. 15-28, Aug. 31, 2011.

Sarkar et al., "Psychobiotics and the Manipulation of Bacteria-Gut-Brain Signals", Trends in Neurosciences, vol. 39, No. 11, pp. 763-781, Nov. 2016.

Villageliu et al., "Dopamine production in Enterococcus faecium: a microbial endocrinology-based mechanism by which probiotics may influence host physiology", Research Manuscript from Iowa State University of Science and Technology, 17 pages, Jul. 22, 2018.

Villageliu et al., "A microbial endocrinology-based simulated small intestinal medium for the evaluation of neurochemical production by gut microbiota", FEMS Microbiology Ecology, vol. 94, 9 pages, May 20, 2018.

"List of dopaminergic drugs", Wikipedia, https://en.wikipedia.org/w/index.php?title=List_of_dopaminergic_drugs&oldid=795790534, 5 pages, Nov. 15, 2018.

Iowa State University Research Foundation, Inc. in connection with PCT/US2018/052128 filed Sep. 21, 2018, "The International Search Report and the Written Opinion of the International Searching Authority, or the Declaration", 25 pages, dated Feb. 6, 2019.

Iowa State University Research Foundation, Inc. in connection with PCT/US2018/052128 filed Sep. 21, 2018, "Correction to ISRWO mailed Feb. 6, 2019", 21 pages, mailed Feb. 26, 2019.

* cited by examiner

PROBIOTIC COMPOSITIONS FOR PRODUCTION OF DOPAMINE

CROSS REFERENCE

This is a U.S. National Phase application claiming priority to PCT/US18/52128 filed Sep. 21, 2018, which claims priority to the earlier filed U.S. Provisional Application having Ser. No. 62/561,745, filed Sep. 22, 2017, and hereby incorporates subject matter of these applications in their entirety.

GRANT REFERENCE

This invention was made with government support under contract Grant No. N00014-15-1-2706 awarded by the Department of Defense, Office of Naval Research. The Government has certain rights in this invention.

FIELD OF THE INVENTION

The present invention is directed to synbiotic compositions and formulations along with uses thereof for targeted clinical and veterinary applications, for example, in promoting health and well-being and/or treating therapeutic conditions. The present invention is also directed to methods of probiotic selection and detection of strains with the ability to produce neurochemicals including dopamine in the gastrointestinal tract. Still further the present invention is directed to industrial applications for production of dopamine utilizing methods and media suitable for the same. The present invention provides a microbial endocrinology-based mechanism and approach for optimization of synbiotic delivery of a probiotic with a neurochemical precursor to beneficially aid in the use of such synbiotics for a variety of conditions and diseases.

BACKGROUND OF THE INVENTION

Probiotics are designated as living microorganisms that may be used for both maintenance of health as well as treatment of specific clinical conditions ranging from gastrointestinal infection to the treatment of neuropsychiatric-related behavioral issues. Probiotics are also extensively used in the farm production industry (chickens, pigs, fish, and cattle) as well as in the treatment of companion animals (dogs, cats, horses). Similarly, probiotics are also extensively used in humans to treat gastrointestinal inflammation and associated conditions negatively impacting the well-being of humans.

The mechanisms by which probiotics may influence animal and human physiology are still unclear. As a result, a critical impediment to the more widespread use of probiotics in medicine is the lack of understanding of the mechanism(s) by which they may exert their purported benefits. By not understanding the mechanism it then becomes nearly impossible to screen the large libraries of probiotics that exist to identify those strains which may be of benefit. The discovery described herein provides a screening approach based upon the microbial endocrinology concept which the inventor has pioneered in the scientific literature.

The concept of microbial endocrinology is based on the ability of microorganisms, such as those classified as probiotics, to produce the same neurochemicals that are produced in the neuroendocrine systems of animals or humans. Such production of neurochemicals would mean that a probiotic can interact with the animal's neurophysiology by acting as a neurochemical delivery vehicle with the potential to influence host health and disease pathogenesis as these typically involve neurochemicals. Thus, identification of a probiotic's ability to produce a specific neurochemical is an important step in the screening process for desirable probiotics and understanding of their mechanism of action in an animal or human. It is well-known that probiotic organisms do not proliferate in artificial media in a manner consistent with their behavior in a natural environment, such as the gastrointestinal tract.

There is a recognized self-protective mechanism for certain neurochemicals, including dopamine which can influence self-protective mechanisms of the gastrointestinal tract. It is recognized that gastric epithelial cells possess dopaminergic receptors and that dopamine agonists can ameliorate gastric ulcers by increasing the secretion of protective mucus and bicarbonate. In addition, dopamine can influence $Na^+$, $Cl^-$ and water absorption as well as $K^+$ and bicarbonate secretion throughout various regions of the GI tract and can stimulate water absorption in vivo. Studies of inflammatory bowel disease (IBD) have also recognized the importance of dopamine as a modulator of immune response and inflammation. An association of reduced endogenous dopamine production and responsiveness with human IBD has been demonstrated. For example, in an animal model of IBD induced with 2,4-dinitrofluorobenzene, the dopamine agonist bromocriptine significantly ameliorated illness by reducing mortality, histopathologic changes such as ulceration and behavioral abnormalities including changes in feeding patterns. In contrast, the dopamine antagonist domperidone significantly increased illness severity with a marked increase in mortality as well as in histopathologic changes. More recently, a study in zebra-fish showed that dopamine receptor agonists alleviate enterocolitis-like inflammation whereas receptor antagonists exacerbate inflammation.

There is also an industrial need for the production of neurochemicals, including dopamine. Industrial production of dopamine has been largely limited to chemical synthesis processes, namely enzymatic systems that use tyrosine phenol-lysase. This provides a two-step reaction for dopamine synthesis from catechol (or pyruvate or ammonia) into L-DOPA and thereafter dopamine. There remains a need for more efficient synthesis methods for the neurochemical. This is further amplified by the various industrial applications of use creating a market demand that has not yet been met by these synthetic methods.

Accordingly, it is an objective of the invention is to produce a synbiotic composition or formulation for delivery of a probiotic with a neurochemical precursor to beneficially produce neurochemicals to ameliorate, treat or prevent gastrointestinal inflammation.

A still further object of the invention is to provide methods of treatment, administering and use of a synbiotic composition or formulation including a probiotic and a neurochemical precursor to ameliorate, treat or prevent gastrointestinal inflammation.

A still further object of the invention is to provide methods of treatment and/or prophylaxis for health maintenance and various diseases and/or conditions associated with dopamine.

Further, it is an objective of the claimed invention to develop a detection or selection methodology for probiotics in targeted clinical and veterinary applications.

It is a further object of the invention is to develop a screening methodology and medium for the same to identify probiotics capable of producing neurochemicals in the gastrointestinal tract of a subject in need thereof.

It is a still further object of the invention is to develop a medium simulating small intestinal medium which allows for the growth of enteric bacteria in an environment reflective of their host-based environment.

It is a still further object of the invention is to develop methods of producing the neurochemical dopamine from a novel medium that allows for the growth of certain bacteria capable of converting precursors into dopamine.

Other objects, advantages and features of the present invention will become apparent from the following specification taken in conjunction with the accompanying figures.

BRIEF SUMMARY OF THE INVENTION

An advantage of the invention is the ability to screen and identify which probiotic/bacterial strains will benefit human/animal health, including for example treatment of gastrointestinal inflammation. It is an advantage of the present invention that certain probiotic bacteria, including certain *Enterococcus* spp. and *Vagococcus* spp., are capable of producing neurochemicals, including dopamine in the gastrointestinal tract of an animal and/or human. Such probiotic bacterial strains are advantageously combined with neurochemical precursors, such as L-DOPA, to influence host physiology in animals, including, but not limited to, farm production and companion animals, and humans.

In an embodiment, the present invention provides a method for selecting or identifying probiotic bacterial strains capable of producing neurochemicals in the gut of an animal or human, comprising the steps of: contacting a medium designed to simulate a salivary phase, gastric phase, and intestinal phase with a probiotic strain; and detecting production of neurochemicals in the medium by the probiotic strain, wherein the probiotic strain's ability to produce neurochemicals indicates a desirable probiotic strain for administering to a subject in need of treating inflammation and/or promoting health in the gut of an animal or human. As referred to herein, the gut includes the gastrointestinal tract as well as organs served by the blood supply to and from the gut.

In an embodiment, the present invention provides a method for treating a subject with gut inflammation and/or need for gut health with a probiotic strain capable of producing neurochemicals in the gut of the subject, comprising: administering to the subject a therapeutically effective amount of at least one probiotic strain; and administering to the subject a therapeutically effective amount of a precursor of the neurochemical in need of production in the gut of the subject. As referred to herein, the gut includes the gastrointestinal tract as well as organs served by the blood supply to and from the gut.

In another embodiment, the invention provides a synbiotic composition comprising: a therapeutically effective amount of at least one probiotic strain; and a therapeutically effective amount of a precursor or a co-factor of dopamine.

In a further embodiment, the invention provides a medium for selecting or identifying probiotic strains capable of producing neurochemicals in the gut of an animal or human comprising: agar inoculated with a simulated small intestine medium comprising: a salivary phase comprising a simulated salivary fluid stock electrolyte and an amylase solution; a gastric phase comprising a simulated gastric fluid stock electrolyte and a pepsin solution; and an intestinal phase comprising a bile salt solution, a pancreatin enzyme solution, hemin, and a simulated intestinal fluid stock electrolyte.

In a further embodiment, the invention provides a method of producing dopamine comprising: providing a medium selected for probiotic strains capable of producing dopamine, contacting the medium with at least one probiotic strain, and producing dopamine.

While multiple embodiments are disclosed, still other embodiments of the present invention will become apparent to those skilled in the art from the following detailed description, which shows and describes illustrative embodiments of the invention. Accordingly, the figures and detailed description are to be regarded as illustrative in nature and not restrictive.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 12A shows the latency to first grooming; FIG. 12B shows the longest time spent on open arms in an elevated plus maze; FIG. 12C shows the number of groomings in an elevated plus maze; FIG. 12D shows the time spent grooming in an elevated plus maze; FIG. 12E shows the total time spent immobile in an elevated plus maze; FIG. 12F shows the average speed spent in the center zone of an open field; FIG. 12G shows the latency to first grooming in an open field; FIG. 12H shows the longest visit to the center zone in an open field; FIG. 12I shows the number of entries to the center zone of an open field; FIG. 12J shows the time spent in the center zone of an open field; and FIG. 12K shows the time spent in the periphery zone of an open field.

FIG. 13A shows the latency to first entry into an open arm of an elevated plus maze; FIG. 13B shows the longest visit to the open arms of an elevated plus maze; and 13C shows the total time spent grooming in the elevated plus maze.

Figure 1A:
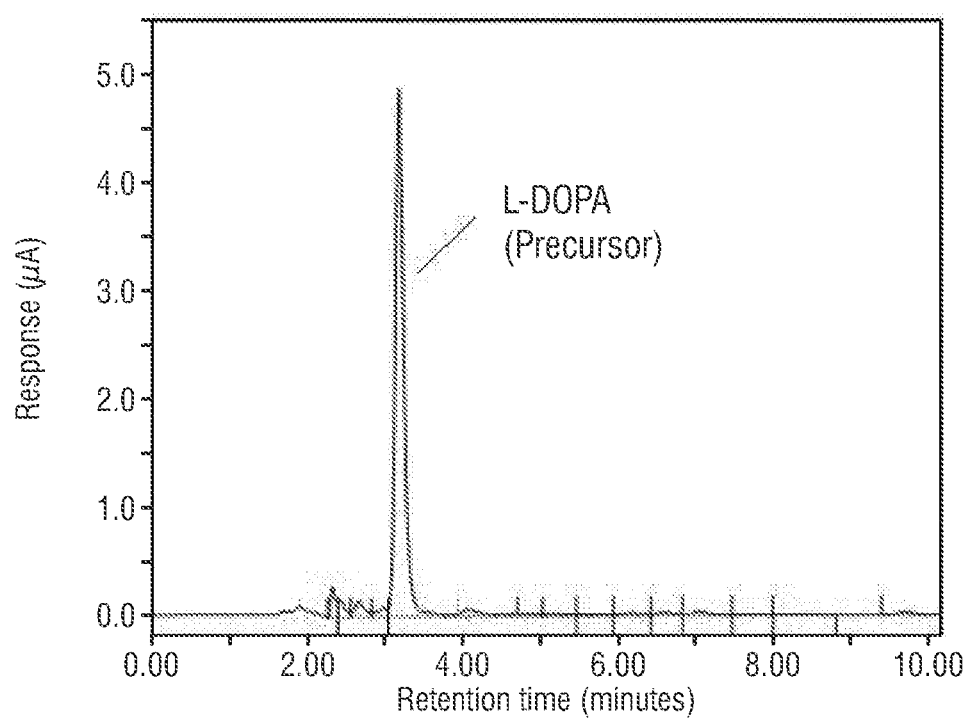
FIG. 1A is a graphical representation of a control sample (medium alone) and FIG. 1B is a graphical representation of *E. faecium* producing dopamine from L-DOPA in simulated small intestine medium (sSIM) which shows the evaluation of an *E. faecium* probiotic in comparison to a control (medium alone) to assess the ability to produce dopamine utilizing a precursor L-DOPA in medium simulating gastrointestinal conditions according to embodiments of the invention.

Reference to various embodiments does not limit the scope of the invention. Figures represented herein are not limitations to the various embodiments according to the invention and are presented for exemplary illustration of the invention.

DETAILED DESCRIPTION OF THE INVENTION

The present invention relates to methods for selecting or identifying probiotic strains capable of producing neurochemicals in the gut of an animal or human. The present invention further relates to methods for treating a subject with gut inflammation and/or need for gut health with a probiotic strain capable of producing neurochemicals in the gut of the subject. Still further the present invention relates to synbiotic compositions providing for administration to a subject comprising a therapeutically effective amount of at least one probiotic strain; and a therapeutically effective amount of a precursor of dopamine. The present methods and compositions have many advantages over conventional administration and/or screening of probiotic strains. Without being limited to the particular mechanisms and benefits of the invention, the methods and compositions overcome a lack of knowledge to in ability to select and use probiotics in medicine based on a desirable mechanism of action, namely a microbial endocrinology-based mechanism for probiotic strains to exert their purported benefits. The present invention overcomes these limitations and provides methods for selecting probiotic strains based upon microbial endocrinology, namely the ability of the strain to produce neurochemicals in the gut of a subject to exert beneficial effects.

The embodiments of this invention are not limited to particular methods of selection, methods of treatment and compositions, which can vary and are understood by skilled artisans. It is further to be understood that all terminology used herein is for the purpose of describing particular embodiments only and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾ This applies regardless of the breadth of the range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring techniques and equipment, with respect to any quantifiable variable, including, but not limited to, mass, volume, time, distance, and the like. Further, given solid and liquid handling procedures used in the real world, there is certain inadvertent error and variation that is likely through differences in the manufacture, source, or purity of the ingredients used to make the compositions or carry out the methods and the like. The term "about" also encompasses amounts that differ due to different equilibrium conditions for a composition resulting from a particular initial mixture. The term "about" also encompasses these variations. Whether or not modified by the term "about," the claims include equivalents to the quantities.

As used herein, the "alimentary tract" refers to the pathway by which food enters the body of a subject and solid wastes are expelled. The alimentary canal includes, for example, the mouth, pharynx, esophagus, stomach, small intestine, large intestine, and anus.

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

As used herein, an "effective amount" or "therapeutically effective amount" refers to the amount of a compound, such as a probiotic strain and/or precursor material that is sufficient to prevent, treat, reduce and/or ameliorate the symptoms and/or underlying causes of a disorder or disease. In an exemplary aspect, an "effective amount" or "therapeutically effective amount" refers to the amount of probiotic and/or precursor that is sufficient to prevent, inhibit, and/or treat gut inflammation and/or promoting health in the gut of an animal or human.

Also, as used herein, the term "gut" refers to the gastrointestinal tract as well as liver, spleen, pancreas, omentum, and other organs served by the blood supply to and from the gut.

The term "intestinal microbiota", as used herein, refers to the population of microorganisms inhabiting the gastrointestinal tract. The term was previously referred to as the intestinal flora.

The term "microbiome", as used herein, refers to a population of microorganisms from a particular environment, including the environment of the body or a part of the body. The term is interchangeably used to address the population of microorganisms itself (sometimes referred to as the microbiota), as well as the collective genomes of the microorganisms that reside in the particular environment. The term "environment", as used herein, refers to all surrounding circumstances, conditions, or influences to which a population of microorganisms is exposed. The term is intended to include environments in a subject, such as a human and/or animal subject.

"Microorganism" refers to an organism or microbe of microscopic, submicroscopic, or ultramicroscopic size that typically consists of a single cell. Examples of microorganisms include bacteria, viruses, parasites, fungi, certain algae, and protozoa. The term "microbial" indicates pertaining to, or characteristic of a microorganism.

As used herein, the term "neurochemical" refers to small organic molecules and peptides that participate in neural, immune and other general physiological activities. Neurochemicals can be produced within in various parts of a subject, such as the gut, brain, etc. Such biogenic neurochemicals are capable of eliciting neural activity. Exemplary neurochemicals include both neurotransmitters and neuromodulators, which can be either excitatory or inhibitor in nature. Exemplary neurochemicals include catecholamines. Further exemplary neurochemicals include glutamate, dopamine, serotonin, histamine, norepinephrine, epinephrine, phenethylamines, thyronamine compounds, tryptamine, GABA, acetylcholine, and the like.

"Non-pathogenic bacteria" refers to bacteria that under normal conditions do not cause a disease or harmful responses in a healthy host. In some embodiments, non-pathogenic bacteria are commensal bacteria. Examples of non-pathogenic bacteria include, but are not limited to *Bacillus* spp., *Bacteroides* spp., *Bifidobacterium* spp., *Brevibacteria* spp., *Clostridium* spp., *Enterococcus* spp., *Escherichia coli*, *Lactobacillus* spp., *Lactococcus* spp., *Saccharomyces* spp., and *Staphylococcus* spp. Naturally pathogenic bacteria may be genetically engineered to provide reduce or eliminate pathogenicity according to standard methods in the art.

The term "population", as used herein, refers to a plurality of individual organisms, in the context of this invention, the term refers in particular to a collection of organisms of diverse taxonomic affiliation, in particular bacteria.

"Prebiotic" is used to refer to a food or dietary supplement that confers a health benefit on a subject associated with modulating a microbiota. Prebiotics in most instances are not drugs, instead functioning due to changes to the resident bacteria either changing the proportions of the resident bacteria or the activities thereof and not functioning because of absorption of the component or due to the component acting directly on the subject. As referred to herein, a prebiotic includes a precursor and/or co-factor to a neurochemical for combined use with a probiotic.

"Probiotic" is used to refer to live, non-pathogenic microorganisms, e.g., bacteria or fungi, which can confer health benefits to a host organism that contains an appropriate amount of the microorganism. In some embodiments, the host organism is a mammal. In some embodiments, the host organism is a human. Some species, strains, and/or subtypes of non-pathogenic bacteria and yeast are currently recognized as probiotics. Examples of probiotics include, but are not limited to, *Candida* spp., *Debaryomyces* spp., *Debaryomyces* spp., *Enterococcus* spp., *Kluyveromyces* spp., *Kluyveromyces* spp., *Saccharomyces* spp., *Yarrowia* spp., *Bifidobacteria* spp., *Escherichia coli*, *Vagococcus* spp., *Carnobacterium* spp., *Melissococcus* spp. and *Lactobacillus* spp., e.g., *Candida humilis*, *Debaryomyces* hansenii, *Debaryomyces occidentalis*, *Kluyveromyces lactis*, *Kluyveromyces lodderae*, *Kluyveromyces marxianus*, *Saccharomyces cerevisiae*, *Saccharomyces boulardii*, *Yarrowia hpolytica*, *Bifidobacterium bifidum*, *Enterococcus faecium*, *Enterococcus faecalis*, *Enterococcus hirae*, *Enterococcus casseliflavus*, *Enterococcus gallinarum*, *Escherichia coli* strain Nissle, *Lactobacillus acidophilus*, *Lactobacillus bulgaricus*, *Lactobacillus paracasei*, *Lactobacillus plantarum*, *Vagococcus fluvaialis* (Dinleyici et al., 2014; U.S. Pat. Nos. 5,589,168; 6,203,797; 6,835,376). The probiotic may be a variant or a mutant strain of bacterium (Arthur et al., 2012; Cuevas-Ramos et al., 2010; Olier et al., 2012; Nougayrede et al., 2006).

Non-pathogenic bacteria may be genetically engineered to enhance or improve desired biological properties, e.g., survivability. Non-pathogenic bacteria may be genetically engineered to provide probiotic properties. Probiotic bacteria and/or yeast may be genetically engineered to enhance or improve probiotic properties. Without being limited to a particular mechanism of the invention, probiotics differ in their ability to produce neurochemicals in the gut of a subject and therefore have differing abilities to treat a subject according to the methods disclosed herein. Non-pathogenic bacteria may be used for probiotic or synbiotic compositions used to treat subjects, while either pathogenic or non-pathogenic bacteria may be used for production of dopamine in media. Pathogenicity, or virulence, of *E. faecium* may be defined as in the European Food Safety Authority, *Scientific Opinion on the safety and efficacy of* Oralin® (*Enterococcus faecium*) *as a feed additive for calves for rearing, piglets, chickens for fattening, turkeys for fattening and dogs*, EFSA Journal 2014; 12(6):3727, 19 pp. (doi:10.2903/j.efsa.2014.3727) in section 2.1.1.

As used herein, the term "*Mucuna*" is interchangeable with *Mucuna puriens*, and as such "*Mucuna* powder" is also interchangeable with *Mucuna puriens* powder.

The term "sample," as used herein, refers to any sample suitable for analyzing or typing according to the methods of the present invention. A sample may be collected from an organism (e.g., human or other mammal subject) and can be in any form, including without limitation a solid material such as a tissue, cells, a cell pellet, a cell extract, or a biopsy, or a biological fluid such as urine, blood, stool, saliva, amniotic fluid, exudate from a region of infection or inflammation, or the like.

As used herein, a "subject" typically includes an animal, more specifically a human subject. In one aspect, the subject is suffering from one or more symptoms of anxiety, depression, gut inflammation, fever, fatigue, abdominal pain, abdominal cramping, blood in the stool, reduced appetite, unintended weight loss or weight gain and/or other negative health indicators related thereto any one or more of such symptoms. A subject may also include any farm production or companion animal, including, but not limited to, poultry such as, but not limited to, chickens, pigeon, and turkeys, and fish such as, but not limited to, catfish, salmon, koi, and tilapia.

The term "synbiotic" or "synbiotic composition", as used herein, refers to combining probiotics and prebiotics in a form of synergism. In a particular aspect, the prebiotics include neurochemicals and its precursors and/or co-factors to be utilized by the probiotic of the synbiotic composition. A synbiotic composition can include a co-formulated composition containing both components and additional functional ingredients required for the delivery thereof. More generally, a synbiotic treatment or method is provided by the delivery of both probiotics and prebiotics to a subject in need thereof, regardless of whether the components are delivered separately to the subject.

By "treatment", "prevention" or "amelioration" of an adverse condition is meant delaying or preventing the onset of such a disease or disorder, reversing, alleviating, ameliorating, inhibiting, slowing down or stopping the progression, aggravation or deterioration the progression or severity of a condition associated with such an adverse condition. In one embodiment, at least one symptom of an adverse condition is alleviated by at least 1%, at least 5%, at least 10%, at least 20%, at least 30%, at least 40%, or at least 50%.

As used herein, the term "administering" refers to the placement of a compound or composition into a subject by a method or route which results in at least partial localization of the compound or composition to the gut or other hollow organ (e.g. oral cavity, vagina) such that a desired effect is produced. A compound or composition described herein can be administered in a human or animal reservoir by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

A probiotic and/or synbiotic may be administered as a lyophilized powder or in a tablet form. The lyophilized powder may be added to a liquid such as, but not limited to, water or food for ingestion. The tablet may be a chewable tablet. The probiotic may be administered live or heat inactivated dead cells, and in whole or in part. The parts of the probiotic may include cellular components, such as, but not limited to, the DNA or protein which are capable of rendering their beneficial effects.

Substrates may be administered in any pharmaceutically acceptable formulation such as, but not limited to, a tablet or as part of a composition comprising the substrate and a pharmaceutically acceptable carrier.

Tablets and capsules for administration may be in unit dose form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tableting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, polysorbate 80, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavoring or coloring agents.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The term "sufficient amount of time", as used herein, refers to time it takes for a compound, material, composition comprising a compound of the present invention, or an organism which is effective for producing some desired effect in at least a sub-population of cells.

As used herein, "substantially free" may refer to any component that the composition of the invention lacks or mostly lacks. When referring to "substantially free" it is intended that the component is not intentionally added to compositions of the invention. Use of the term 'substantially free" of a component allows for trace amounts of that component to be included in compositions of the invention because they are present in another component. However, it is recognized that only trace or de minimus amounts of a component will be allowed when the compositions is said to be "substantially free" of that component. Moreover, the term if a composition is said to be "substantially free" of a component, if the component is present in trace or de minimus amounts it is understood that it will not affect the effectiveness of the compositions. It is understood that if an ingredient is not expressly included herein or its possible inclusion is not stated herein, the invention composition may be substantially free of that ingredient. Likewise, the express inclusion of an ingredient allows for its express exclusion thereby allowing a composition to be substantially free of that expressly stated ingredient.

Media Having a Gastrointestinal-Like Environment

In one aspect, the present invention involves a media having a gastrointestinal-like environment of a human or animal (simulated small intestinal media, sSIM or SIM) developed to make the media suitable for microbial growth unlike the InfoGest Consensus Method media found in Mackie and Rigby (InfoGest Consensus Method. In: Verjoeckx, K, et al. (eds). *The Impact of Food Bioactives on Health: In vitro and In vivo Models*. Cham: Springer International Publishing, 2015; 13-22). In an aspect, the medium employed simulates gastrointestinal conditions of digestion.

In an aspect, the medium includes a salivary phase, gastric phase, and intestinal phase. In an aspect, the medium comprises a simulated salivary fluid (SSF) comprising of salivary electrolyte solution and an amylase solution for the salivary phase. In an aspect, the medium comprises a simulated gastric fluid (SGF) comprising of a gastric electrolyte solution and an enzyme solution for the gastric phase. In an aspect, the medium comprises a simulated intestinal fluid (SIF) comprising of a bile salt solution, an enzyme solution, hemin, and an intestinal electrolyte solution for the intestinal phase.

The various phases may comprise of different electrolytes and solutions. In an embodiment, an oral phase is made by mixing feed into the SSF in about a 1:1 ratio for about 60 seconds, for about 90 seconds, for about 120 seconds, for about 180 seconds, for about 300 seconds, or longer. In other embodiments, depending on the feed and the SSF concentrations, this ratio can be readily altered to obtain desired concentrations of ions and enzymes. For example, if the SSF is made as a concentrated solution and the feed is mainly liquid or semi-solid, the feed to SSF ratio may be about 1.5:1, about 2:1, about 3:1, or more.

In an embodiment, the SSF comprises water to adjust for desired concentrations; pH agents to adjust to a pH of about 6.0 to about 8.0, from about 6.5 to about 7.5, or from about 6.8 to about 7.2; a salivary electrolyte solution comprising potassium chloride, potassium phosphate monobasic, magnesium chloride, sodium bicarbonate, and ammonium carbonate; and an amylase solution of α-amylase. The salivary electrolyte solution, or a solution further supplemented with salts, such as calcium chloride, should provide a potassium ion concentration of about 10 mM to about 30 mM, from about 15 mM to about 25 mM, or from about 15 mM to about 20 mM; a sodium ion concentration of about 5 mM to about 25 mM, from about 10 mM to about 20 mM, or from about 10 mM to about 15 mM; a chloride ion concentration of about 10 mM to about 30 mM, from about 15 mM to about 25 mM, or from about 15 mM to about 20 mM; a dihydrogen phosphate ion concentration of about 1 to about 10 mM, from about 2 to about 5 mM, or from about 2 to about 4 mM; a carbonate and bicarbonate ion concentration of about 5 mM to about 25 mM, from about 10 mM to about 20 mM, or from about 10 mM to about 15 mM; a magnesium ion concentration of about 0.05 mM to about 0.25 mM, from about 0.10 mM to about 0.20 mM, or from about 0.10 mM to about 0.18 mM; an ammonia ion concentration of about 0.05 mM to about 0.25 mM, from about 0.10 mM to about 0.20 mM, or from about 0.10 mM to about 0.15 mM; and a calcium concentration of about 0.5 to about 10 mM, from about 1 to about 5 mM, or from about 1 to about 3 mM. The final activity of α-amylase should be from about 50 U/mL to about 250 U/mL, from about 100 U/mL to about 200 U/mL, or from about 125 U/mL to about 175 U/mL.

In further embodiments, additional surface-active proteins which may be found in human or animal, such as mucin, may be added to the oral phase.

The oral phase can either be directly used to make the gastric phase or can be frozen for future use.

In an embodiment, the gastric phase is made by mixing a fresh or thawed, if frozen, oral phase with the SGF in about a 1:1 ratio for about 30 minutes, for about 45 minutes, for about 60 minutes, for about 90 minutes, for about 120 minutes, for about 150 minutes, or longer. In other embodiments, depending on the oral phase and SGF concentrations, this ratio can be readily altered to obtain desired concentrations of ions and enzymes. For example, if the SGF is made as a concentrated solution and the oral phase is not, the oral phase to SGF ratio may be about 1.5:1, about 2:1, about 3:1, or more. Alternatively, if the oral phase is concentrated, the oral phase to SGF ratio may be about 1:1.5, about 1:2, about 1:3, or less.

In an embodiment, the SGF comprises water to adjust for desired concentrations; pH agents, such as HCl, to adjust to a pH of about 1.5 to about 4.0, from about 2.0 to about 3.5, or from about 2.5 to about 3.5; a gastric electrolyte solution comprising potassium chloride, potassium phosphate monobasic, magnesium chloride, sodium bicarbonate, ammonium carbonate, and sodium chloride; and an enzyme solution of pepsin. The gastric electrolyte solution, or a gastric electrolyte solution supplemented with other salts, such as calcium chloride, should provide a potassium ion concentration of about 3 mM to about 15 mM, from about 5 mM to about 10 mM, or from about 6 mM to about 8 mM; a sodium ion concentration of about 60 mM to about 85 mM, from about 65 mM to about 80 mM, or from about 70 mM to about 75 mM; a chloride ion concentration of about 60 mM to about 85 mM, from about 65 mM to about 80 mM, or from about 70 mM to about 75 mM; a dihydrogen phosphate ion concentration of about 0.1 to about 1.5 mM, from about 0.5 to about 1.0 mM, or from about 0.7 to about 1 mM; a carbonate and bicarbonate ion concentration of about 15 mM to about 35 mM, from about 20 mM to about 30 mM, or from about 22 mM to about 28 mM; a magnesium ion concentration of about 0.01 mM to about 0.20 mM, from about 0.05 mM to about 0.15 mM, or from about 0.08 mM to about 0.12 mM; an ammonia ion concentration of about 0.10 mM to about 10 mM, from about 0.50 mM to about 5.0 mM, or from about 0.8 mM to about 1.5 mM; and a calcium concentration of about 0.05 to about 1.00 mM, from about 0.10 to about 0.50 mM, or from about 0.10 to about 0.30 mM. The final activity of pepsin should be from about 500 U/mL to about 4000 U/mL, from about 1000 U/mL to about 3000 U/mL, or from about 1500 U/mL to about 2500 U/mL.

In further embodiments, the SGF may contain mucin. The mucin may serve as a rich carbon and energy source for the probiotics and may increase the suitability of the media for microbial growth. If mucin is added to the SGF, it should comprise from about 0.5 mg/mL to about 5.0 mg/mL, from about 0.7 mg/mL to about 2.0 mg/mL, or from about 0.7 mg/mL to about 1.5 mg/mL.

The oral phase can either be directly used to make the gastric phase or can be frozen for future use. Additionally, if supplemented with a sufficient carbon source, such as mucin, the gastric phase may be suitable for the culture of some bacteria found in the stomach, such as, but not limited to, *H. pylori*.

In an embodiment, the intestinal phase is made by mixing the gastric phase with the SIF in about a 1:1 ratio for about 30 minutes, for about 45 minutes, for about 60 minutes, for about 90 minutes, for about 120 minutes, for about 150 minutes, or longer, preferably for about 120 minutes. In other embodiments, depending on the gastric phase and the SIF concentrations, this ratio can be readily altered to obtain desired concentrations of ions and enzymes. For example, if the is SIF is made as a concentrated solution and the gastric phase is not, the oral phase to SIF ratio may be about 1.5:1, about 2:1, about 3:1, or more. Alternatively, if the gastric phase is concentrated, the gastric phase to SIF ratio may be about 1:1.5, about 1:2, about 1:3, or less.

In an embodiment, the SIF comprises water to adjust for desired concentrations; pH agents, such as NaOH, to adjust to a pH of about 6.0 to about 8.0, from about 6.5 to about 7.5, or from about 6.8 to about 7.2; an intestinal electrolyte solution comprising potassium chloride, potassium phosphate monobasic, magnesium chloride, sodium bicarbonate, and sodium chloride; and an enzyme solution. The intestinal electrolyte solution, or an intestinal electrolyte solution supplemented with other salts, such as calcium chloride, should provide a potassium ion concentration of about 3 mM to about 15 mM, from about 5 mM to about 10 mM, or from about 6 mM to about 8 mM; a sodium ion concentration of about 110 mM to about 135 mM, from about 115 mM to about 130 mM, or from about 120 mM to about 125 mM; a chloride ion concentration of about 45 mM to about 65 mM, from about 50 mM to about 60 mM, or from about 53 mM to about 58 mM; a dihydrogen phosphate ion concentration of about 0.1 to about 1.5 mM, from about 0.5 to about 1.0 mM, or from about 0.6 to about 1 mM; a carbonate and bicarbonate ion concentration of about 75 mM to about 95 mM, from about 80 mM to about 90 mM, or from about 82 mM to about 88 mM; a magnesium ion concentration of about 0.20 mM to about 0.40 mM, from about 0.25 mM to about 0.35 mM, or from about 0.30 mM to about 0.35 mM; and a calcium concentration of about 0.05 to about 15.0 mM, from about 1.0 to about 10.0 mM, or from about 2.0 to about 8.0 mM.

The enzyme solution may be made from a human or animal pancreatin extract, which may comprise a mix of trypsin, chymotrypsin, pancreatic amylase, lipase, ribonuclease, and/or protease. The enzyme solution may also be made from individual enzymes. The final activity of trypsin may be from about 50 U/mL to about 200 U/mL, from about 75 U/mL to about 150 U/mL, or from about 90 to about 120 U/mL based on the TAME (p-toluene-sulfonyl-L-arginine methyl ester) assay; the final activity of chymotrypsin may be from about 10 U/mL to about 40 U/mL, from about 15 U/mL to about 35 U/mL, or from about 20 U/mL to about 30 U/mL based on the BTEE (benzoyl-L-tyrosine ethyl ester)

assay; the final activity of pancreatic amylase may be from about 100 U/mL to about 300 U/mL, from about 150 U/mL to about 250 U/mL, or from about 175 U/mL to about 225 U/mL based on the liberation of maltose from starch; the final activity of lipase may be about 1000 U/mL to about 3000 U/mL, from about 1500 U/mL to about 2500 U/mL, or from about 1750 U/mL to about 2250 U/mL based on the release of free fatty acid from tributyrin.

The bile solution may be made from bile salts or fresh bile. The bile salts may have a final concentration of about 1 mM to about 20 mM, from about 5 to about 15 mM, or from about 7 to about 12 mM. The bile salts may comprise a mix of cholic acid salts and/or deoxycholic acid salts. Derivatives of cholic acid and/or deoxycholic acid, such as taurohyodeoxycholate, glycohyodeoxycholate, taurocholate, glycocholate, taurochenodeoxycholate, glycochenodeoxycholate, taurodeoxycholate, glycodeoxycholate, and/or other derivatives may also comprise the bile salts in various amounts to mimic a specific human or animal if desired. For example, a bovine bile salt mix may comprise of about 25% to about 35% taurocholate, about 40% to about 50% glycocholate, about 1% to about 3% taurochenodeoxycholate, about 1% to about 5% glycochenodeoxycholate, about 5% to about 10% taurodeoxycholate, and about 5% to about 15% glycodeoxycholate, whereas a porcine salt mix may comprise of about 35% to about 40% taurohyodeoxycholate, about 30% to about 35% glycohyodeoxycholate, about 1% to about 3% taurochenodeoxycholate, and about 25% to about 30% glycochenodeoxycholate.

The hemin solution should be added after the gastric phase is mixed with the SIF. The hemin solution may comprise about 0.01% to about 0.10% hemin, about 0.1% to about 0.8% hemin, or about 0.2% to about 0.8% hemin and about 100 mM to about 150 mM, from about 110 mM to about 140 mM, or about 120 mM to about 130 mM potassium phosphate dibasic dissolved in water.

After the hemin is added, the sSIM may be degassed for anaerobic probiotics by cycles of freeze/thaw in liquid nitrogen. This will also render the sSIM sterile. The sSIM may then be used or frozen at about −80° C. for future use.

Mixing at every step may simulate gastric mixing, such as by using a stomacher. While other methods, such as a magnetic stir bar may be used, the mixing may not be sufficient to create a homogenous mixture.

In an aspect, the medium is an agar inoculated with the simulated small intestine medium comprising the salivary phase, gastric phase, and intestinal phase. In an aspect, the salivary phase and gastric phase a mixed together to produce gastric phase products. Thereafter, the gastric phase products are combined with the intestinal phase before cryopreservation and degassing.

Methods for Selecting or Identifying Probiotic Strains Capable of Producing Neurochemicals in the Gut In one aspect, the present invention involves a method for selecting or identifying probiotic strains capable of producing neurochemicals in the gut of an animal or human. In one aspect, the method includes contacting a medium having a gastrointestinal-like environment with a probiotic strain for evaluation and detecting whether the probiotic strain produces neurochemicals in the medium. In an aspect, the medium employed provides a gastrointestinal-like environment to determine whether probiotic strains will physiologically function as neurochemical delivery vehicles to produce physiologically significant quantities of neurochemicals, such as dopamine in a gastrointestinal-like environment if given access to the dopamine precursor L-3,4-dihydroxyphenylalanine (L-DOPA). In an embodiment, the medium employed providing a gastrointestinal-like environment is sSIM.

The gastrointestinal-like environment possesses biochemical characteristics comparable to gastrointestinal contents. In an aspect, the medium includes precursor molecules for the evaluated probiotic strains to use in synthesizing neurochemicals, including for example L-DOPA, L-tyramine, L-tyrosine, or choline. In an embodiment, the input food for sSIM contains a high level of L-DOPA. Non-limiting examples are foods high in L-DOPA including *Mucuna pruiens, Vicia faba*, and from the genera of *Phanera, Pillostigma, Canavalia*, and *Dalbergia*. The various plants may be ground into a powder and added as a food supplement in the salivary phase of sSIM, and may comprise about 0% to about 20%, 0.15% to about 15%, or about 0.15% to about 10%. In other embodiments, the precursors may be added in purified form, and may be added to reach a final concentration in sSIM in about 0 µM to about 5 mM, from about 50 µM to about 3 mM, or about 100 µM to about 2.5 mM. In an aspect, the probiotic strain is a bacterial strain. In a preferred aspect, the bacterial strain is an *Enterococcus* spp. and/or *Vagococcus* spp. as described herein.

In an aspect, the methods include the detection of a production of neurochemicals on the medium. In an aspect, the production of neurochemicals on the medium when combined with a precursor to the neurochemicals. In an aspect, the neurochemicals detected include dopamine, glutamate, serotonin, histamine, norepinephrine, epinephrine, phenethylamines, thyronamine compounds, tryptamine, GABA, acetylcholine and the like. In a preferred aspect, the neurochemicals detected include dopamine. Detection may be done with any method that can directly report the presence or amount of the neurochemicals, including, but not limited to, ELISA, liquid chromatography, such as ultra-high-performance liquid chromatography (UHPLC), or mass spectrometry. Optionally, metabolites, such as but not limited to 3-methoxytyramine, catecholamines, and phenol-containing aromatic amines, may be detected in samples (Villageliu, D, et al., 2018, *A microbial endocrinology-based simulated small intestinal medium for the evaluation of neurochemical production by gut microbiota*, FEMS Microbiol Ecol, 94(7); doi: 10.1093/femsec/fiy096, herein incorporated by reference).

In an aspect, probiotic strains demonstrating neurochemical production in the amount of at least about 10 ng/g dry weight. In another aspect, probiotic strains demonstrating neurochemical production in the amount of at least about 100 ng/g, at least about 500 ng/g, at least about 1 µg/mL, at least about 5 µg/mL, at least about 10 µg/mL, at least about 20 µg/mL, at least about 30 µg/mL, at least about 40 µg/mL, at least about 50 µg/mL, at least about 60 µg/mL, at least about 70 µg/mL, at least about 80 µg/mL, at least about 90 µg/mL, at least about 100 µg/mL, at least about 110 µg/mL, at least about 120 µg/mL, at least about 130 µg/mL, at least about 140 µg/mL, at least about 150 µg/mL, or greater.

In another aspect, the methods can further include an initial step of screening a subject's microbiome for the presence or absence of bacterial strains capable of producing neurochemicals in the gut of the subject. Beneficially, it is identified herein that the microbiome can be a prolific source of dopamine in the gut, including the gastrointestinal track and provides a mechanism for efficacy of certain probiotic strains capable of producing neurochemicals, such as, but not limited to, dopamine.

In such an aspect, a biological sample is preferably received from a subject in a non-invasive manner and the biological sample is used to contact probiotic strains contained therein to the medium to determine the ability to produce neurochemicals in the gut of the subject. In variations, non-invasive manners of sample reception can use any one or more of: a permeable substrate (e.g., a swab configured to wipe a region of a subject's body, toilet paper, a sponge, etc.), a non-permeable substrate (e.g., a slide, tape, etc.), a container (e.g., vial, tube, bag, etc.) configured to receive a sample from a region of a subject's body, and any other suitable sample-reception element. In a specific example, samples can be collected from one or more of a subject's nose, skin, genitals, mouth, and gut in a non-invasive manner (e.g., using a swab and a vial). However, one or more biological samples of the set of biological samples can additionally or alternatively be received in a semi-invasive manner or an invasive manner. In variations, invasive manners of sample reception can use any one or more of: a needle, a syringe, a biopsy element, a lance, and any other suitable instrument for collection of a sample in a semi-invasive or invasive manner. In specific examples, samples can comprise blood samples, plasma/serum samples (e.g., to enable extraction of cell-free DNA), and tissue samples.

In such an aspect of the invention where bacterial strains are obtained from a sample of a subject, the growth and expansion of bacterial strains to be screened can be accomplished by standard methods known those of skill in the art. For example, probiotics and/or strains obtained from a subject are grown for a sufficient amount of time, for example, growth may be for 4, 6, 8, 10, 11, 12, 13, 14, 15, 16, 17, 18, 19, or 20 hours. Likewise, incubation typically occurs at 37° C., however temperatures may be adjusted from about 20° C. to about 40° C. to influence, for example, growth rate of said strains.

In another aspect, the growth and expansion may be performed on a media that simulates a gastrointestinal environment. In an embodiment, sSIM is used to grow the probiotics for 4, 6, 8, 10, 11, 12, 13, 14, 15, 16, 17, 18, 19, 20, 24, or 48 hours or longer from about 20° C. to about 40° C., at about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., or higher.

In one embodiment, the methods of the present invention are useful to predict clinical benefits of treating a subject suffering from conditions such as, for example, gastrointestinal inflammation. In one aspect, the methods include screening the microbiome of the subject to determine the presence or absence of bacterial strains in the subjects' microbiome which possess the capability to produce neurochemicals, including dopamine, when combined with a neurochemical precursor, including L-DOPA and/or L-Tyrosine.

In another embodiment, the screening and targeting of the neurochemical production in the gut of a subject described according to embodiments of the invention provide targets for various therapeutic modalities. Such therapeutic modalities can include drug applications, synbiotic composition applications, and other therapeutic applications including general health and well-being of a subject.

Methods for Treating a Subject

In one aspect, the present invention involves a method for treating a subject with gut inflammation and/or need for gut health with a probiotic strain capable of producing neurochemicals in the gut of the subject. As one skilled in the art recognizes, there is a biochemical signaling in the gut-brain axis joining the microbiota, the alimentary tract (including the gastrointestinal tract) and the central nervous system. The gut-brain axis includes the microbiota in the alimentary tract, central nervous system, neuroendocrine and neuroimmune systems (e.g. hypothalamic-pituitary-adrenal axis), sympathetic and parasympathetic arms of the autonomic nervous system, and the gut microbiota. Beneficially, the methods of treatment are suitable for adjuvant treatment of various therapeutic treatments of pathologies of the gut. These and other applications will be readily apparent based on the disclosure herein.

The methods of treatment based on the ability to produce dopamine in the gut provide various applications of use. One skilled in the art appreciates the production of dopamine is dependent on precursor substrate concentration, the target tissue and the differential expression of differing types of receptors/effector mechanisms. For example, in circular muscle, dopamine can induce contractions with an $EC_{50}$ of $6.3 \times 10^{-6}$ mol/L. In contrast, in longitudinal muscle, dopamine can produce relaxation with an $EC_{50}$ of $2.9 \times 10^{-5}$ mol/L. Disruption of the dopaminergic transporters results in altered colonic motility. As shown in FIGS. 3A-3H, even the weakest producing viable strain of $E.$ $faecium$ ML1088 can produce dopamine levels of $2.4 \times 10^{-4}$ mol/L and intravenous dopamine dosing for the treatment of shock is typically 1 to 5 µg/kg/min. Accordingly, the methods of producing dopamine in the gut—even one milliliter of cecal material having the capacity to generate over 130 µg of dopamine—present physiological significance of the treatment methods described herein.

The methods of treatment are further suitable for use in treating and/or preventing various gastrointestinal conditions, including for example, ulcers, namely gastric ulcers, diarrhea, inflammatory bowel disease (IBD) and associated symptoms and conditions, feeding conditions causing behavioral abnormalities, enterocolitis-type inflammation, and the like.

The methods of treatment are further suitable for use in treating and/or preventing various diseases and conditions associated with dopamine. In an exemplary aspect, inflammation, such as inflammatory bowel disease, are well-suited for treatment and prevision as the provision of dopamine may alleviate and/or assist with treatment thereof. Accordingly, various other diseases and conditions associated with the neurochemical dopamine would benefit from the methods and/or compositions disclosed herein.

Still further, the methods of treatment are further suitable for use in treatment and/or maintaining general health and well-being of a subject.

In one aspect, the methods include administering to the subject a therapeutically effective amount of at least one probiotic strain and administering to the subject a therapeutically effective amount of a precursor and/or co-factor of the neurochemical in need of production in the gut of the subject. In an aspect, the subject is an animal or human. In an aspect, a therapeutically effective amount of a probiotic strain can include from about $10^4$ CFU to about $10^{12}$ CFU, from about $10^5$ CFU to about $10^{11}$ CFU, or from about $10^5$ CFU to about $10^{10}$ CFU. In an aspect, a therapeutically effective amount of a precursor and/or co-factor of a neurochemical can include up to about 1 mg/kg, about 10 mg/kg, about 50 mg/kg, about 100 mg/kg, or about 200 mg/kg of L-DOPA. Therapeutic ranges for other precursor and/or co-factor will depend on various factors present.

In an aspect, the probiotic strain is a bacterial strain. In a preferred aspect, the bacterial strain is an $Enterococcus$ spp.

and/or *Vagococcus* spp. Various *Enterococcus* spp., including *Enterococcus faecium* and *Enterococcus hirae*, are found in probiotic mixtures as well as in fermentation products. The bacteria are beneficially resistant to gastric juice and bile salts, a trait advantageous when attempting to deliver these organisms as an oral probiotic. Various *Vagococcus* spp. exhibit similar activity to the *Enterococcus* spp.

In an aspect, the precursor of the neurochemical is provided as a therapeutic agent. In a further aspect, the precursor of the neurochemical is provided as a food source. In a further aspect, the precursor of the neurochemical can be preloaded on the probiotic strain, such as a bacterial strain that is grown/germinated in a medium containing the precursor of the neurochemical.

In a preferred aspect, the precursor of the neurochemical is L-3,4-dihydroxyphenylalanine (L-DOPA). In a further preferred aspect, the precursor L-DOPA is provided from a food and/or dietary supplement source (e.g. herbal extracts), including for example plant foods including broad beans, *Mucuna pruriens, Vicia faba*, and sources from the genera *Parkinsoiiia, Phanera, Piliostigina, Prosopis, Cassia, Canavalia*, and *Dalbergia*, and *Vigna*.

In an aspect, the precursor can be provided as the product of another bacterial strain, or of a transformed bacterial strain, or as a co-culture with another strain, or as a pure chemical added, which generates the prebiotic composition. An exemplary precursor may be organisms containing, such as an organism naturally expression or an organism transformed to express, tyrosine hydrolase which can convert tyrosine into L-DOPA. Transforming bacteria using heat shock, electroporation, and particle bombardment is well known in the art.

In an aspect, the co-factor of the neurochemical dopamine can include pyridoxal phosphate (Pyridoxal 5-phosphate, PAL-P, PLP, Vitamin B6 phosphate).

In an aspect, the probiotic strain and precursor and/or co-factor of the neurochemical are co-administered in a single delivery system to the subject. In a further aspect, the single delivery system can be a co-formulation of the probiotic strain and the precursor and/or co-factor or a co-packaged formulation of the probiotic strain and the precursor and/or co-factor. In an alternative aspect, the probiotic strain and precursor and/or co-factor of the neurochemical are co-administered to the subject in distinct or separate delivery systems. In a further aspect, the probiotic strain and precursor and/or co-factor of the neurochemical can be separately administered in sequence, wherein the probiotic strain is administered first and thereafter the precursor and/or co-factor of the neurochemical is administered second. Alternatively, the probiotic strain and precursor and/or co-factor of the neurochemical can be separately administered in sequence, wherein the precursor and/or co-factor of the neurochemical is administered first and thereafter the probiotic strain is administered second.

In an aspect, the various embodiments of the probiotic strain and the precursor and/or co-factor of the neurochemical are administered orally to the subject. Oral administration can include various dosage forms as one skilled in the art will ascertain, including for example, tablets, capsules, aqueous or oily suspensions, solutions, emulsions, syrups or elixirs, dry products for reconstitution with water or other suitable vehicle before use.

In an aspect, the probiotic strains produce the neurochemical in the gut of the subject in the amount of at least about 1 µg/mL (micrograms/mL), at least about 5 µg/mL, at least about 10 µg/mL, at least about 20 µg/mL, at least about 30 µg/mL, at least about 40 µg/mL, at least about 50 µg/mL, at least about 60 µg/mL, at least about 70 µg/mL, at least about 80 µg/mL, at least about 90 µg/mL, at least about 100 µg/mL, at least about 110 µg/mL, at least about 120 µg/mL, at least about 130 µg/mL, at least about 140 µg/mL, at least about 150 µg/mL, or greater. In further aspects, the probiotic strains produce the neurochemical in the gut of the subject in the amount of at least about 1 ng/mL to 1 mg/mL.

Synbiotic Compositions

Synbiotic compositions include a therapeutically effective amount of a probiotic strain and a therapeutically effective amount of a precursor of a neurochemical. A therapeutically effective amount of a probiotic strain can include from about $10^4$ CFU to about $10^{12}$ CFU, from about $10^5$ CFU to about $10^{11}$ CFU, or from about $10^5$ to about $10^{10}$ CFU. In an aspect, a therapeutically effective amount of a precursor of a neurochemical, specifically L-DOPA, can include up to about 1 mg/kg, about 10 mg/kg, about 50 mg/kg, about 100 mg/kg, or about 200 mg/kg of L-DOPA.

In an aspect, the probiotic strain is a bacterial strain. In a preferred aspect, the bacterial strain is an *Enterococcus* spp. and/or *Vagococcus* spp.

In an aspect, the precursor of the neurochemical is L-3,4-dihydroxyphenylalanine (L-DOPA). In an aspect, the co-factor is pyridoxal phosphate. In another aspect, the precursor L-DOPA is provided from a food source and/or a therapeutic agent.

The synbiotic compositions are provided for oral administration. Oral administration can include various dosage forms as one skilled in the art will ascertain, including for example, tablets, capsules, aqueous or oily suspensions, solutions, emulsions, syrups or elixirs, dry products for reconstitution with water or other suitable vehicle before use.

Tablets and capsules for oral administration may be in unit dose form, and may contain conventional excipients such as binding agents, for example syrup, acacia, gelatin, sorbitol, or polyvinyl-pyrrolidone; fillers for example lactose, sugar, maize-starch, calcium phosphate, sorbitol or glycine; tableting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, polysorbate 80, or acacia; non-aqueous vehicles (which may include edible oils), for example almond oil, fractionated coconut oil, oily esters such as glycerin, propylene glycol, or ethyl alcohol; preservatives, for example methyl or propyl p-hydroxybenzoate or sorbic acid, and if desired conventional flavoring or coloring agents.

Tablets and capsules may be formulated as a time release tablet or capsule in order to target different organs along the alimentary track.

Methods for Producing Industrial Quantities of Dopamine

In one aspect, the present invention involves a method for producing dopamine for industrial applications. The methods include providing a probiotic strain(s) capable of producing neurochemicals to a medium. In some aspects, a medium having a gastrointestinal-like environment, including either a precursor and/or co-factor for dopamine, or providing a precursor and/or co-factor to a medium in combination with the probiotic strain(s), and producing dopamine. In an embodiment, the media is sSIM. In other aspects, any media can be employed, such as but not limited to tryptic soy broth (TSB), Luria Broth (LB), Brain Heart Infusion (BHI) Broth, De Man Rogosa and Sharpe (MRS) Broth, thioglycolate broth, and variants, and the probiotic strain, such as *E. faecium* strains ML1089, ML1086, ML1081, or ML1082, is provided to the media in combination with either a precursor and/or co-factor for dopamine. Beneficially, the methods provide for the production of dopamine using any commercially-available media with the introduction of the precursor and/or co-factor for dopamine. In an aspect, the method for producing dopamine for industrial application further includes a step of isolating dopamine from the media, such as, but not limited to, using UHPLC to extract out the dopamine.

In an aspect, any media suitable for inoculating a probiotic strain in combination with a dopamine precursor and/or co-factor as described herein can be employed for production of dopamine. Beneficially, it is the combined administration of the probiotic strain in combination with a dopamine precursor and/or co-factor on the media which provides increased conversion of the precursor and/or cofactor by the probiotic strain to produce dopamine as was not previously appreciated.

In an aspect, a medium employed simulates gastrointestinal conditions of digestion. In an aspect, the medium employed provides a gastrointestinal-like environment to determine whether probiotic strains will physiologically function as neurochemical delivery vehicles to produce physiologically significant quantities of neurochemicals, such as dopamine, in a gastrointestinal-like environment if given access to a precursor, such as the dopamine precursor L-3,4-dihydroxyphenylalanine (L-DOPA), and/or a co-factor such as pyridoxal phosphate. In an aspect, the media possesses biochemical characteristics comparable to gastrointestinal contents. In an aspect, the media includes precursor molecules for the evaluated probiotic strains to use in synthesizing neurochemicals, including for example L-DOPA and/or pyridoxal phosphate. In an aspect, the methods include producing dopamine grown on the media.

In an aspect, the media includes a salivary phase, gastric phase, and intestinal phase. In an aspect, the media comprises a simulated salivary fluid stock electrolyte and an amylase solution for the salivary phase. In an aspect, the media comprises a simulated gastric fluid stock electrolyte and a pepsin solution for the gastric phase. In an aspect, the media comprises a bile salt solution, a pancreatin enzyme solution, hemin, and a simulated intestinal fluid stock electrolyte for the intestinal phase. In an embodiment, the media is sSIM. In a further embodiment, the media is sSIM where the food input into the salivary phase is supplemented with a or powder or other food, such as, but not limited to, a *Mucuna* powder or *Vicia faba* green pods, high in L-DOPA. In another embodiment, the sSIM media is supplemented with purified L-DOPA. In some embodiments, the concentration of available L-DOPA in sSIM about 90 µM, about 140 µM, about 500 µM, about 1 mM, about 2.5 mM, or more. The available precursor can be adjusted depending on the conversion ability of the probiotic and the desired final concentration of the neurotransmitter.

In an aspect, the media is an agar inoculated with the simulated small intestine media comprising the salivary phase, gastric phase, and intestinal phase.

In an aspect, the salivary phase and gastric phase are mixed together to produce gastric phase products. Thereafter, the gastric phase products are combined with the intestinal phase before cryopreservation and degassing.

In an aspect, any methods of isolating dopamine from a medium employed herein can be employed as will be appreciated by those skilled in the art, such as, but not limited to, pressure systems, affinity beads, and/or filters. In an embodiment, dopamine is extracted using UHPLC.

In an aspect, the probiotic strain is a bacterial strain. In a preferred aspect, the bacterial strain is an *Enterococcus* spp. and/or *Vagococcus* spp. as described herein. The precursors and/or co-factors described herein can be incorporated into a medium for the production of dopamine or alternatively provided to the medium with the probiotic strain for the production of dopamine. Beneficially, in an aspect of the invention, the bacterial strain conversion of the precursor and/or co-factor of dopamine into dopamine is at least about 10%, at least about 20%, at least about 30%, at least about 40%, at least about 50%, at least about 60%, at least about 70%, at least about 80%, at least about 90%, at least about 95%, or about 100% providing highly efficient production methods.

EXAMPLES

Example 1

In order to first establish that probiotics are capable of producing neurochemicals, the dopamine production of probiotics was evaluated. The evaluation of a commercially available probiotic formulation Probios® containing four probiotic species, including *E. faecium*, was conducted to determine the ability to produce the neurochemical dopamine. The probiotic strains were grown anaerobically for twenty-four hours on TSA agar with 5% ovine blood. Following plate growth, colonies were suspended in peptone water to make standardized suspensions for inoculation. Each suspension was adjusted such that the material to be inoculated had an OD600 measurement of 0.200 (+/−0.005).

The probiotic strains inoculated a specialized medium, simulated Small Intestinal Media (sSIM, see Example 4), designed to reflect physiological conditions in the gastrointestinal tract. 4.8 mL of sSIM was spiked with 100 µL of a 0.05 M L-DOPA solution. L-DOPA solution was prepared by weighing dry L-DOPA purchased from Sigma and dissolving it in 0.1M HCl. For a sample with a total volume of 5 mL, 4.8 mL of sSIM was mixed with 100 µL of L-DOPA spiking solution and 100 µL of bacterial suspension. This yielded a final L-DOPA concentration of 1 mM. Inoculated samples were grown at 37° C. anaerobically while being subjected to low speed (100 rpm) magnetic stir bar mixing. All conditions were run in triplicate.

The L-DOPA concentration was set to be high enough to be non-limiting in order to better resolve L-DOPA usage differences between various strains of Enterococci. At lower concentrations of L-DOPA, it is possible for all available L-DOPA to be consumed without reliably distinguishing the strains capable of greater production. Further, this concentration falls into a meaningful physiological range. Every milliliter of sSIM derives from the digestion of 125 mg of raw undigested dry material. As each mL of sSIM is spiked with 197 µg of L-DOPA in addition to the 10 µg/mL baseline provided by the sSIM, the total L-DOPA content would be roughly equivalent to a food consisting of 0.17% L-DOPA by mass. Naturally L-DOPA rich foods, like the green pods of broad/fava beans (*Vicia faba*), can reach concentrations as high as 6.75%. Similar L-DOPA concentrations might also be achieved by imbibing a tablet containing 100 mg L-DOPA (common prescription strength) along with a small 60-gram snack.

Figure 1B:
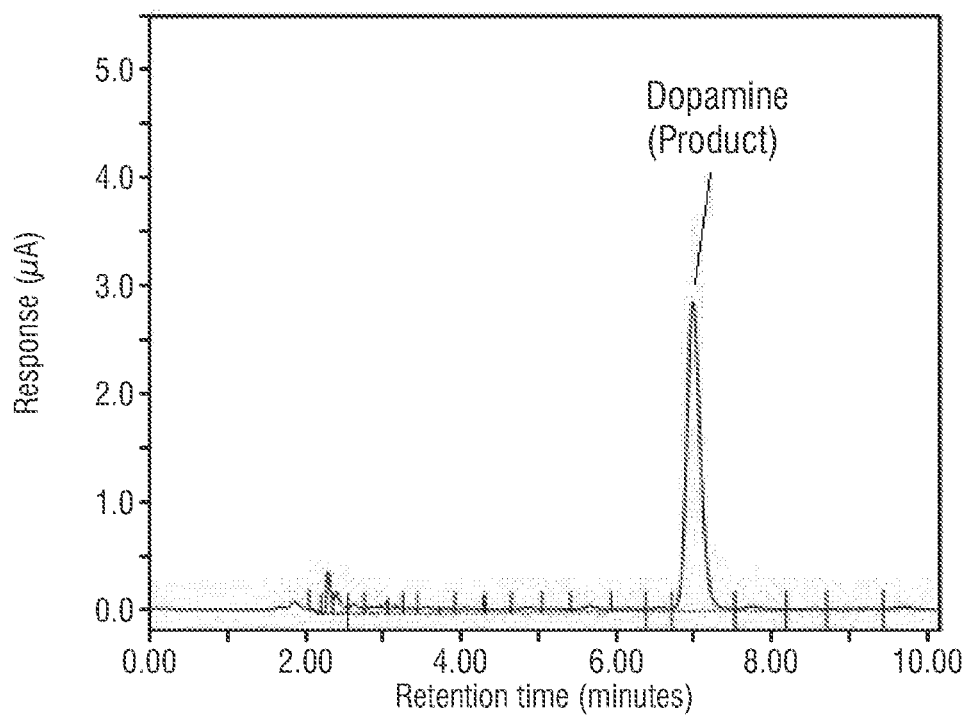

The results are shown in FIG. 1 where the Probios® product produced dopamine in the medium. The two HPLC chromatograms compare a control to the medium inoculated with a probiotic. The HPLC separates the individual components apart and the area under each peak determines the concentration of each metabolite. The peak for dopamine is much larger and the L-DOPA peak greatly decreases in the presence of the probiotic. Further characterization revealed that only the E. faecium component in the product was producing dopamine (data not shown). This shows that the E. faecium strains of Probios® are capable of converting L-DOPA into dopamine in the sSIM media.

Example 2

A similar evaluation was completed on another commercially available probiotic, Fortiflora which contains only E. faecium as well as E. faecium strains isolated from the environment (see Table 1). The probiotic strains of E. faecium were isolated from Probios and Fortiflora using standard microbiological techniques and identification by MALDI. All isolates identified by MALDI had highly reliable identification scores of >2.4.

The probiotic strains were grown and plated on medium as described in Example 1. The evaluated strains and sources thereof, along with the results of production of the dopamine in the medium are shown in Table 1 (as the average±SEM). The conversion efficiency was calculated as follows:

$$\text{Conversion Efficiency} = \frac{[L\text{-}DOPA]_i - [L\text{-}DOPA]_f}{[L\text{-}DOPA]_i} \times \frac{[Dopamine]_f - [Dopamine]_i}{[L\text{-}DOPA]_i - [L\text{-}DOPA]_f} \times 100 = \frac{[Dopamine]_f - [Dopamine]_i}{[L\text{-}DOPA]_i}$$

UHPLC was used in order to determine the amount of the various catecholamines. Dopamine, L-DOPA and other metabolites were isocratically separated by a reversed-phase column at a flow rate of 0.6 ml min-1 using a Dionex Ultimate 3000 HPLC system (pump ISO-3100SD, Thermo Scientific, Bannockburn, Ill.) equipped with a refrigerated automatic sampler (model WPS-3000TSL). The electrochemical detection system included a CoulArray model 5600A coupled with an analytical cell (microdialysis cell 5014B) and a guard cell (model 5020). Data acquisition and analysis were performed using Chromeleon 7 and ESA CoulArray 3.10 HPLC Software.

To evaluate the efficiency of the ultra-high-performance liquid chromatography with electrochemical detection (UHPLC-ECD) system to extract dopamine from the media the amount of predicted dopamine return was compared to the actual dopamine return. First, to evaluate a control sample of sSIM, freshly prepared stock solution was made by dissolving 47 mg of dopamine hydrochloride (FW: 189.64) into 5 mL of HPLC grade water for a concentration of 50 mM. One hundred microliters of the stock solution was added to 4.9 mL of sSIM medium for a concentration of 1 mM in a total volume of 5.0 mL. The mass of the dopamine (FW 153.18) component added would be expected to be 766 µg. Measurements of unsupplemented sSIM indicate only very trace quantities of dopamine (<2 µg/mL). For the purposes of this evaluation, 5 mL of sSIM should have 776 µg.

This estimate was then compared to the amount of dopamine returned by the UHPLC-ECD system. The 5 mL spiked sample was acidified by the addition of 50 µL of 10N HCl and centrifuged at 3000×g at 4° C. for 15 minutes to remove insoluble fiber, denatured proteins, and other precipitates. The supernatant was processed for UHPLC-ECD by passage through a 3 kDa molecular weight cut off filter. The UHPLC-ECD determination of dopamine concentration in the supernatant was 122 mcg/mL. To determine the total volume of supernatant, the volume of the dry pellet (0.275 grams) was subtracted from the total volume of 5 mL medium (4.691 grams) to yield the supernatant mass (4.416 grams). The density of the supernatant was determined to be 1.02 grams/mL. Thus, a final volume of 4.33 mL of supernatant was present in a typical 5 mL sSIM sample. 122 mcg dopamine/mL×4.33 mL yields the total dopamine mass of 528 mcg (recovery of 68.1%.) The discrepancy can likely be attributed to losses from the molecular exclusion filter as well as residual dopamine associated with material forming the pellet.

TABLE 1

| Strain | Source | Avg. L-DOPA (µg/mL) | Avg. Dopamine (µg/mL) | L-DOPA Consumed (µg) | Dopamine Produced (µg) | Conversion Efficiency (%) |
|---|---|---|---|---|---|---|
| CONTROL |  | 179.10 ± 0.99 | 2.00 ± 0.01 | 0.00 | 0.00 |  |
| ML1081 | Fortiflora | 32.93 ± 0.37 | 89.75 ± 1.71 | 146.18 | 87.75 | 63.1 |
| ML1082 | Probios | 2.61 ± 0.05 | 135.73 ± 2.65 | 176.49 | 133.73 | 96.1 |
| ML1085 | Caine urine | 52.34 ± 2.55 | 79.88 ± 1.31 | 126.76 | 77.88 | 56.0 |
| ML1086 | Canine incision | 2.86 ± 0.31 | 108.00 ± 2.18 | 176.24 | 106.00 | 76.2 |
| ML1087 | Feline urine | 167.43 ± 2.64 | 11.68 ± 0.70 | 11.68 | 9.68 | 7.0 |
| ML1088 | Avian yolk sac | 114.95 ± 4.61 | 38.89 ± 2.98 | 64.16 | 36.88 | 26.5 |
| ML1089 | Canine bile | 17.83 ± 2.90 | 106.45 ± 3.69 | 161.28 | 104.45 | 75.1 |

In addition to dopamine, L-DOPA recovery was also assayed using the same approach. Briefly, 197 µg L-DOPA/mL sSIM (227 µg L-DOPA/mL supernatant) is spiked in. Baseline sSIM supernatant contains about 10 µg/mL. For 4.33 mL of supernatant, a total L-DOPA mass of 983 µg is expected. Samples were determined by HPLC to have 180

μg L-DOPA/mL supernatant; therefore, a total of 779 μg was recovered yielding a total recovery of 79.2%.

Figure 2:
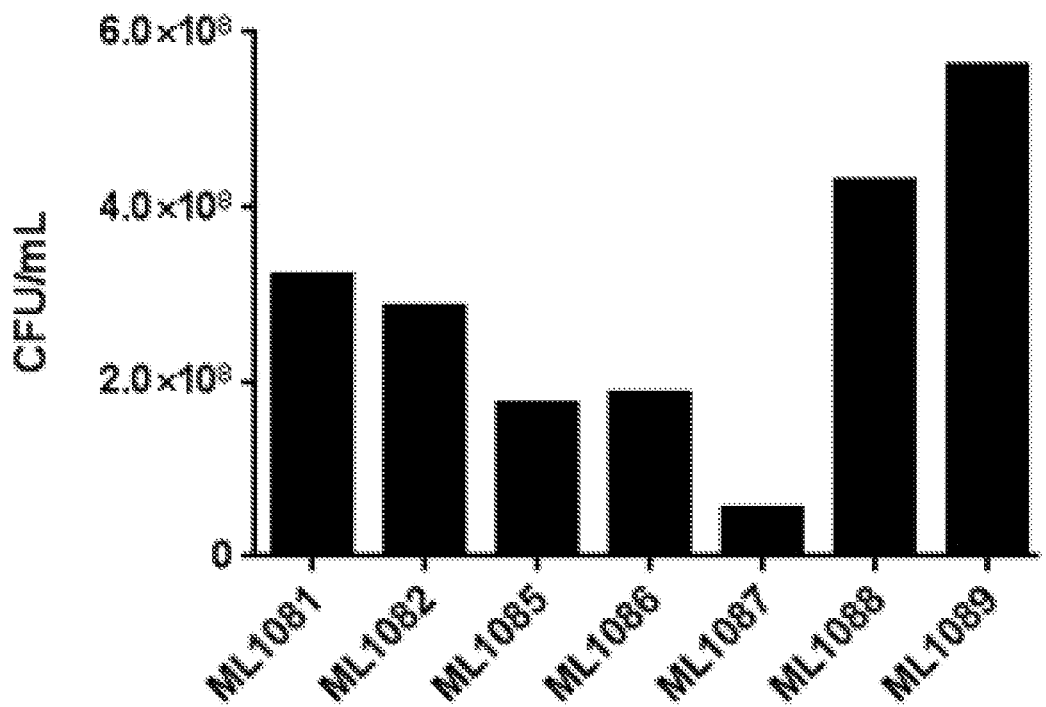
FIG. 2 is a graphical representation showing the growth of various strains of *E. faecium* in a media simulating gastrointestinal conditions, sSIM, according to embodiments of the invention.
Figure 3A:
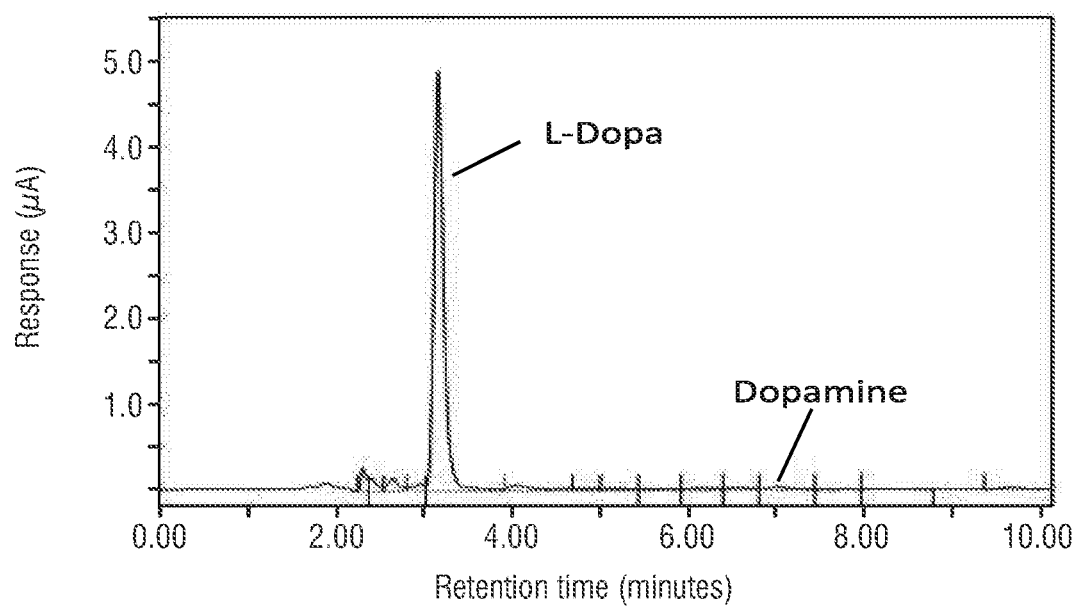
FIG. 3A is a graphical representation showing the chromatogram of the control sSIM demonstrating no conversion of L-DOPA conversion without a monoculture of *E. faecium* in sSIM supplemented with $1.0 \times 10^{-3}$ M L-DOPA.
Figure 3B:
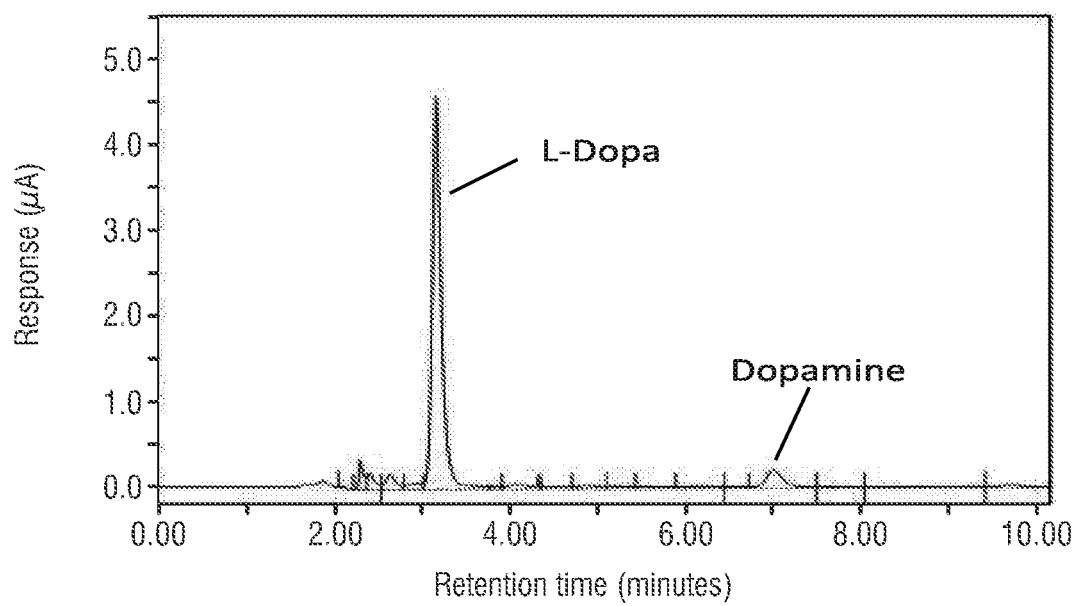
FIG. 3B is a graphical representation of strain ML1087 grown in $1.0 \times 10^{-3}$ M L-DOPA supplemented sSIM.
Figure 3C:
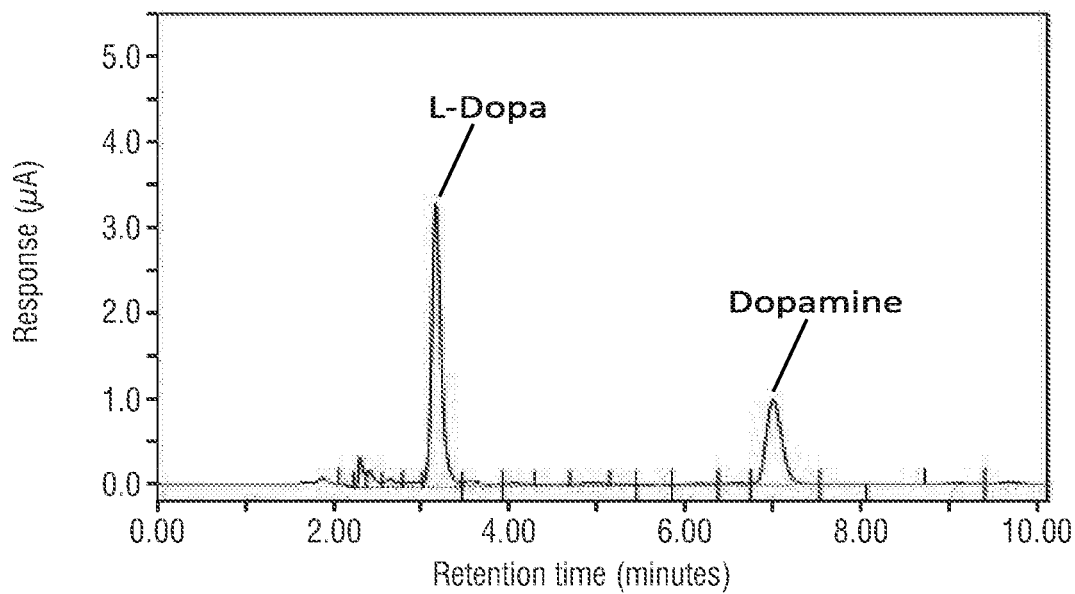
FIG. 3C is a graphical representation of ML1088 grown in $1.0 \times 10^{-3}$ M L-DOPA supplemented sSIM.
Figure 3D:
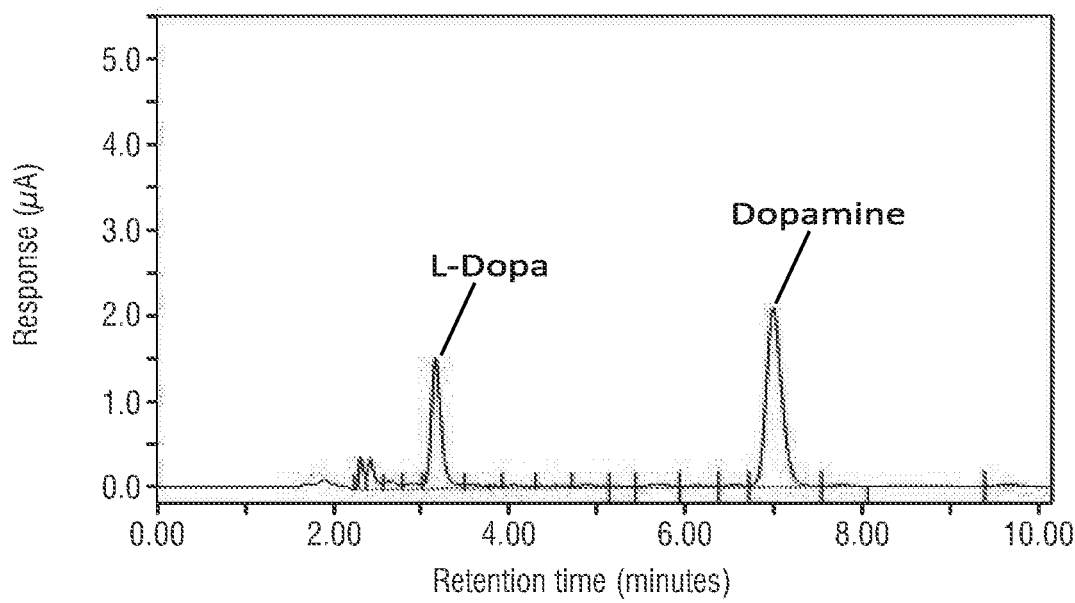
FIG. 3D is a graphical representation of ML1085 grown in $1.0 \times 10^{-3}$ M L-DOPA supplemented sSIM.
Figure 3E:
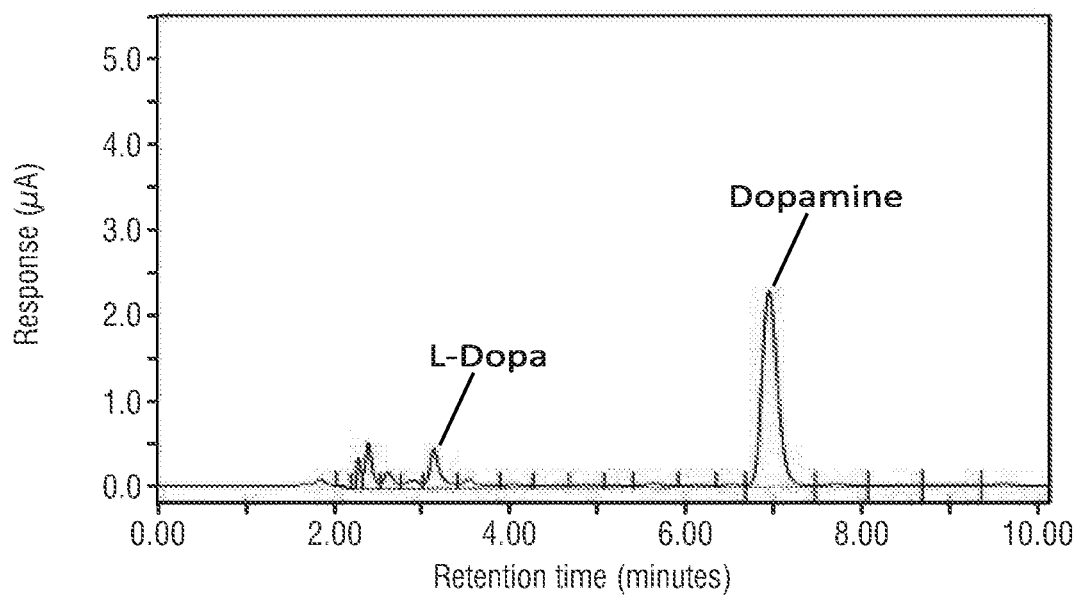
FIG. 3E is a graphical representation of ML1089 grown in $1.0 \times 10^{-3}$ M L-DOPA supplemented sSIM.
Figure 3F:
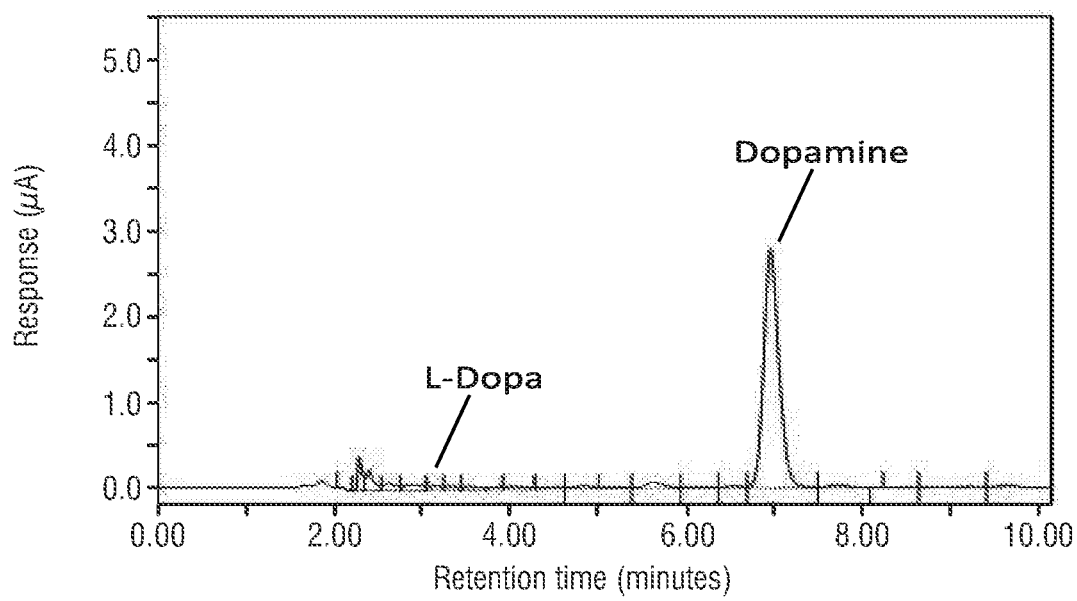
FIG. 3F is a graphical representation of ML1086 grown in $1.0 \times 10^{-3}$ M L-DOPA supplemented sSIM.
Figure 3G:
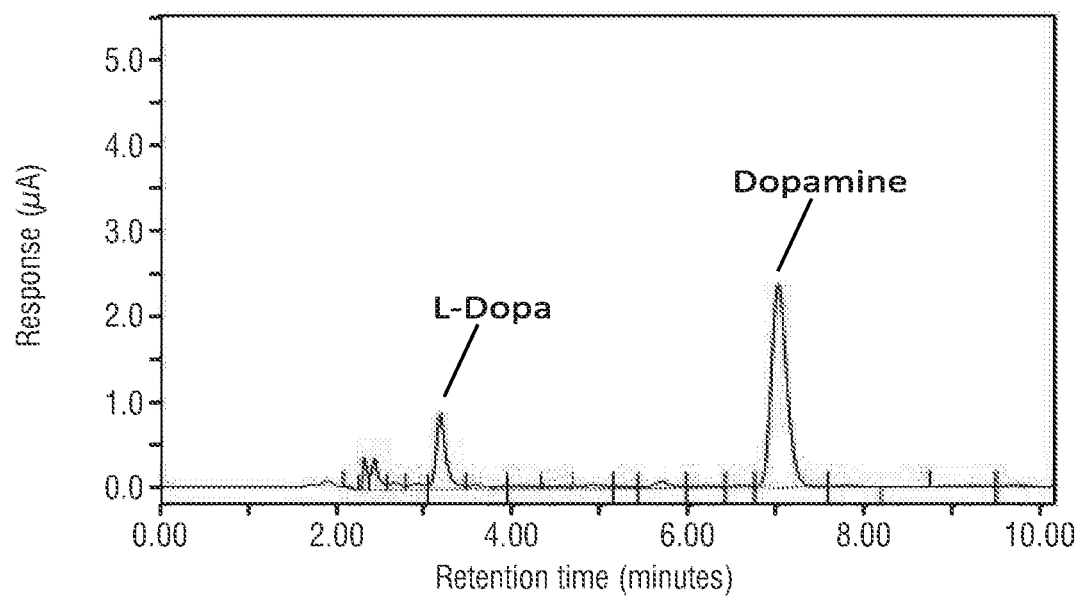
FIG. 3G is a graphical representation of ML1081 grown in $1.0 \times 10^{-3}$ M L-DOPA supplemented sSIM.
Figure 3H:
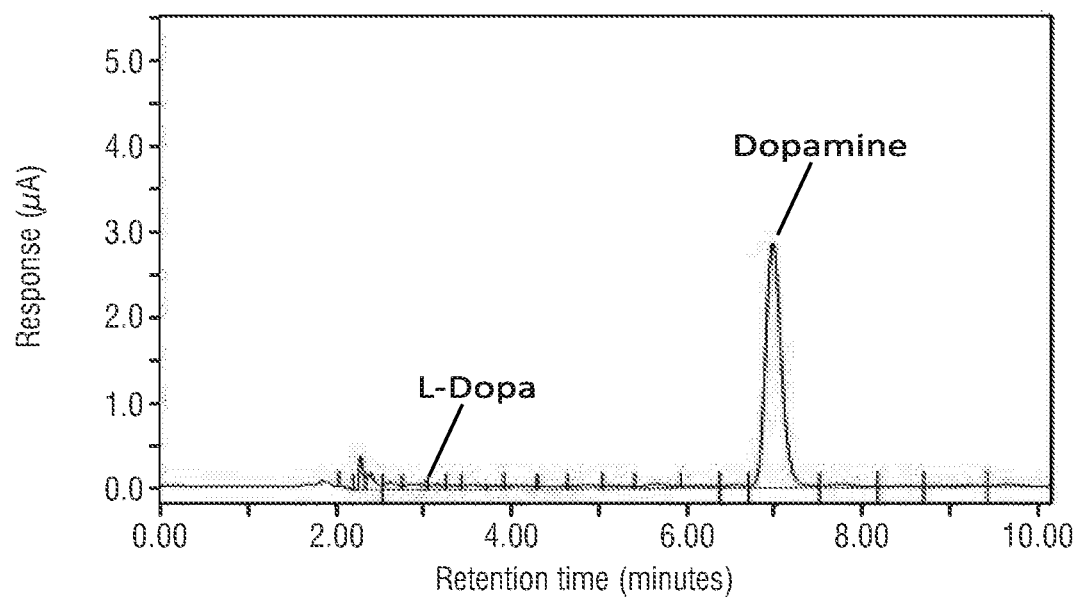
FIG. 3H is a graphical representation of ML1082 grown in $1.0 \times 10^{-3}$ M L-DOPA supplemented sSIM.

The results are shown in Table 1 and FIGS. 3A-3H where the strains of *E. faecium* grown in sSIM supplemented with $1.0 \times 10^{-3}$ M L-DOPA are depicted. Both dopamine production and L-DOPA utilization efficacy were evaluated along with population differences (FIG. 2) between strains.

The results show the probiotic strain isolated from Probios® consistently demonstrated the greatest level of production at over 133 μg/mL in sSIM. This production was more than 26% greater than the next highest producer, a clinical strain designated ML1086. Both of these strains demonstrated comparable levels of population growth and the consumption of L-DOPA appeared to be exhaustive in both of these samples with less than 2% of the starting L-DOPA remaining in both samples. Differences in the final dopamine concentrations of these samples appear to arise from differing efficiencies in the conversion of L-DOPA to dopamine. ML1082 demonstrated a conversion efficiency of 96%, 20% higher than the efficiency of ML1086.

The probiotic strain isolated from Probios® consistently demonstrated the greatest level of dopamine production (133 μg/mL, Conversion Efficiency (C.E.) 96%). Among the other samples, there was a high level of variation in the capacity to produce dopamine and in the ability to reproduce within the gastrointestinal-like contents of the sSIM. The strain ML1088 demonstrated one of the highest observed levels of population growth but was a relatively poor producer of dopamine (37 μg/mL, C.E. 27%). ML1087 produced the lowest amount of dopamine (10 μg/mL, C.E. 7%), likely due to poor growth in the sSIM ($5.45 \times 10^7$ CFU/mL). All other strains were able to achieve growths on the order of $1.0 \times 10^8$ CFU/mL with prolific strains like ML1089 achieving population over a full order of magnitude greater than ML1087. This data confirms the capacity to produce dopamine from L-DOPA may be a common trait among members of the *Enterococcus* spp. as each tested strain demonstrated some capacity to generate dopamine.

However, the conversion efficiency of L-DOPA to dopamine varies greatly among individual *E. faecium* isolates (FIGS. 3A-3H). Thus, if dopamine production is beneficial to the host, then not all strains of *E. faecium* would be expected to be equally suitable for roles in probiotics.

Notably, the results described herein demonstrate an ability of all the tested *E. faecium* strains to produce amount some amount of dopamine, with some strains capable of producing dopamine in excess of the amounts known to impact gastrointestinal conditions. For example, the $EC_{50}$ of maximal response in the distal colon was only $2.0 \times 10^{-5}$ M, which is well below the production of dopamine exhibited by various *E. faecium* strains in this Example, including from $1.0 \times 10^{-4}$ M to $1.0 \times 10^{-3}$ M.

These results also show that depending on a subject's condition, various strains may be administered to fine tune the treatment for the condition. For example, if a subject was greatly in need of dopamine, strain ML1082 may be administered to the subject along with L-DOPA. In comparison, if a subject was slightly below dopamine levels, strain ML1087 may be administered.

Example 3

Figure 4:
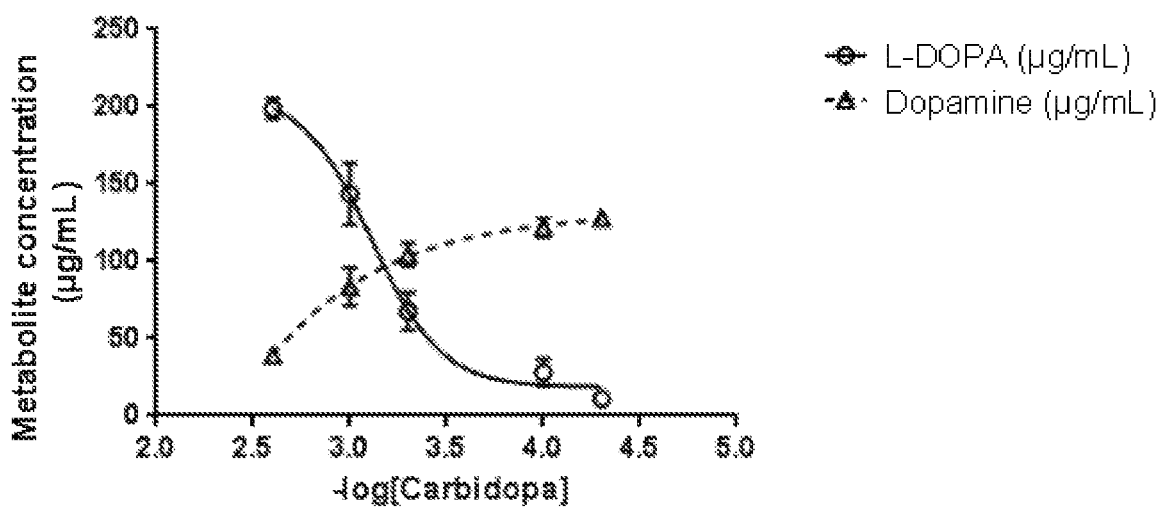
FIG. 4 shows the dopamine production of an *E. faecium* strain, ML1082, demonstrated dose-dependent inhibition in the presence of the L-DOPA decarboxylase inhibitor Carbidopa.

To further verify the strains were producing dopamine from L-DOPA, carbidopa, an inhibitor of neurotransmitter production, including dopamine, was added to sSIM. The dopamine production of our most efficient strain, ML1082, also demonstrated dose-dependent inhibition in the presence of the L-DOPA decarboxylase inhibitor Carbidopa (FIG. 4). A L-DOPA rich diet or a commonly prescribed 100 mg dose of L-DOPA would yield a concentration of about $1.0 \times 10^{-3}$ M concentration in sSIM. It follows then that a tablet that has 1:10 Carbidopa:L-DOPA tablet would likely result in a Carbidopa concentration of approximately ⅒th that on the order of $1.0 \times 10^{-4}$ M ($-\log$ [Carbidopa]=4).

FIG. 4 shows the concentration of carbidopa decreases going from left to right on this reverse logarithmic plot. A functional approximation of the $IC_{50}$ for dopamine was calculated to be $1.53E^{-3}$. The $IC_{50}$ was similar to the L-DOPA concentration of $1.26 \times 10^{-3}$ M, a finding that may indicate a competitive inhibitory mechanism for the bacterial enzyme.

Example 4

As probiotics do not grow normally or well in currently available media, sSIM was developed and evaluated. For the development of sSIM, catecholamines as well as acetylcholine serve as examples of neurochemicals that are quantifiable. However, the procedures herein can be adapted for many other neurochemicals or molecules of interest. The composition of sSIM closely approximates the electrolyte composition, osmolarity, pH and the digestive enzyme content of each phase of digestion. The products of digestion are therefore expected to be similar to products produced in vivo. Included in the matrix are essential precursors and cofactors necessary for neurochemical production as well as nutrients such as B vitamins, bile, and hemin. The medium also contains insoluble fiber, digestive enzymes, neurochemical precursors, and mucin which are inherent to the gastrointestinal contents yet seldom included in conventional media recipes. This complexity can directly influence the behavior of microorganisms and their production of neurochemicals.

The preparation of sSIM represents, in large part, modifications to the InfoGest Consensus Method protocol, in which food is sequentially digested over a salivary phase, gastric phase, and intestinal phase, because the InfoGest Consensus Method is not suitable for microbial growth. In the initial salivary phase, 60 g of ground and autoclaved Teklad Global Diet #2019S (Envigo, Madison, Wis.) was mixed with a salivary solution containing 11.7 mL sterile $H_2O$, 300 μL 0.3M $CaCl_2$, 42 mL simulated salivary fluid stock electrolyte (SSFSE) and 6 mL alpha-amylase solution. SSFSE was made by taking one liter of deionized distilled $H_2O$ and adding 1.41 g KCl, 625 mg $KH_2PO_4$, 1.43 g $NaHCO_3$, 38 mg $MgCl_2$ and 7 mg $(NH_4)_2CO_3$. This electrolyte was autoclaved and then titrated with 10 N HCl to a pH 7.0. Alpha-amylase solution was made by dissolving 30 mg alpha-amylase (Sigma, St. Louis, Mo.) into 10 mL of SSFSE. Before mixing with feed, the complete salivary solution was warmed to 37° C. The mixing of feed with the salivary solution occurred in a stomacher bag (Thermo Scientific, Sunnyvale, Calif.). The material was hand kneaded for two minutes to ensure all material is wetted.

The gastric phase began immediately following the salivary phase. To the products of the salivary phase, a gastric solution comprised of 90 mL simulated gastric fluid stock electrolyte (SGFsE), 60 μL 0.3 M $CaCl_2$, 2.4 mL 1 M HCl, 3.54 mL sterile $H_2O$, 120 mg type III mucin (Sigma, St. Louis, Mo.), and 24 mL pepsin enzyme solution was added. SGFsE was prepared by dissolving 643 mg KCl, 153 mg $KH_2PO_4$, 2.625 g $NaHCO_3$, 3.4475 g NaCl, 30 mg MgCl and 60 mg $(NH_4)_2CO_3$ into 1 L of sterile deionized distilled water. This solution was autoclaved and adjusted to pH 3.00 using 10 N HCl. The pepsin enzyme solution was prepared by mixing 2.00 g pepsin (Sigma, St. Louis, Mo.) with 25 mL SGFsE. The complete gastric solution was warmed to 37° C. prior to usage. Once the salivary products and complete gastric solution had been mixed, the entire mixture was paddle blended at 180 rpm using a triple mix paddle blender for two hours at 37° C.

The intestinal phase began immediately following the gastric phase. To the gastric phase products, an intestinal solution composed of 30 mL bile salt solution, 60 mL pancreatin enzyme solution, 480 µL, hemin solution, 132 mL simulated intestinal fluid stock electrolyte ($SIF_{SE}$), 480 µL 0.3 M CaCl2, 1.8 mL 1 N NaOH and 15.72 mL sterile $H_2O$ was added. $SIF_{SE}$ was made with 634 mg KCl, 136 mg $KH_2PO4$, 8.93 g $NaHCO_3$, 83 mg $MgCl_2$ and 2.805 g NaCl. $SIF_{SE}$ was autoclaved and adjusted to pH 7.0 using 10 N HCl. Bile salt solution was made by dissolving 2.02 g bovine bile salts (Sigma, St. Louis, Mo., product # B3883) into 30 mL $SIF_{SE}$. Pancreatin enzyme solution consisted of 6.9 g porcine pancreatin (Sigma, St. Louis, Mo.) dissolved into 60 mL $SIF_{SE}$. Hemin solution was made by dissolving 500 mg hemin (Sigma, St. Louis, Mo.) and 1.74 g $K_2HPO_4$ into 100 mL sterile water. Prior to usage, the complete intestinal solution was warmed to 37° C. Once the gastric phase products and complete intestinal solution were mixed, the mixture was paddle blended at 120 rpm for two hours at 37° C. Cryopreservation and degassing was carried out by flash freezing in liquid nitrogen and followed by thawing under a vacuum for a total of 3 cycles. sSIM was stored at −80° C.

Samples of prepared media (100 µL) were inoculated on plates of blood agar (TSA with 5% bovine blood) (Remel Inc., San Diego, Calif.), Miller LB agar (Difco™, Sparks, Md.) and Lactobacilli MRS agar (Difco™, Sparks, Md.), incubating anaerobically and aerobically to check for sterility. Broths of BHI (brain heart infusion) (BBL™, Sparks, Md.) and MRS were also inoculated with 100 µL of media. No growth was observed in any condition after several days.

To inoculate the media and to determine if bacteria may grow in sSIM, samples of freshly collected swine feces (100 mg) were mixed with 5.0 mL of sSIM. Samples were grown anaerobically, at 37° C. with continuous stirring for 24 hours. Following growth, 100 µL it samples of spent media were taken and serially diluted in peptone water for plating on blood agar; remaining media was processed for the evaluation of metabolites. Spent media samples were grown on blood agar plates, anaerobically, at 37° C. and over the timeframe of one week. Plates were examined daily and colonies with distinct morphology were selected for identification by MALDI-TOF (MALDI Biotyper, Bruker Inc, Billerica, Mass.). Unique strains were preserved cryogenically using a 20% glycerol solution in BHI broth. For individual strain inoculation, isolates were grown on blood agar and incubated in anaerobic conditions at 37° C. Colonies were suspended into peptone water and $OD_{600}$ measurements were made to standardize the inoculation density. For *Lactobacillus reuteri*, a 100 µL of a solution of $5 \times 10^8$ CFU/mL was used to inoculate 4.9 mL of sSIM for an initial concentration of $10^7$ CFU/mL. Inoculated media were grown anaerobically, at 37° C. and with magnetic agitation for 24 hours.

Following inoculation and growth, to analyze neurotransmitter production, each sample was analyzed by UHPLC-EDC. Each sample of spent media was acidified with the addition of 10 µL of 10N HCl for every 1 mL of media. Samples were centrifuged (3000×g, 4° C. for 15 minutes) to remove insoluble fiber as well as precipitated proteins. The supernatant was further cleaned by passage through a molecular weight cut off (MWCO) filter. In most cases, passage through a 10 kDa MWCO was sufficient; however, occasionally there are organisms which produce products necessitating passage through a 3 kDa MWCO filter. Once filtered, samples were stored at −80° C. Metabolites typically appear stable over weeks, however, expedient evaluation is preferred due to possible degradation over prolonged storage. Samples processed in this manner can be run directly, extracted or derivatized depending on the metabolites of interest. Catecholamines are inherently electrically active and require no further preparation if electrochemical detection is used. In the case of acetylcholine, the post column addition of a solid phase reactor which utilizes immobilized acetylcholinesterase and choline oxidase allows for quantification.

The separation and quantification of catecholamines by UHPLC-ECD was done using a 150 mm, 3 µm Hypersil BDS C18 column (Thermo Scientific, Sunnyvale, Calif.) along with a buffered 10% acetonitrile mobile phase marketed as MD-TM mobile phase (Thermo Scientific, Sunnyvale, Calif.). Processed samples were diluted 10 to 100-fold using mobile phase to avoid overloading the column. Spiked samples were diluted an additional 100-fold. Samples were injected using a Dionex Ultimate 3000 autosampler while pressure is provided by a coupled Dionex Ultimate 3000 pump. Flow rate was set to 0.6 mL/minute with samples held at 4° C. by the autosampler. Components were detected by a 6041RS glassy carbon electrode set to 400 mV and mounted in the Dionex Ultimate 3000 RS Electrochemical detector (Thermo Scientific, Sunnyvale, Calif.).

In a complex mixture like sSIM, the recovery of any specific metabolite can dramatically vary by pH. Depending on the material digested, the media can contain some hydrophobic surfaces which can sequester and remove target molecules during ultra filtration. Using tools modeled after the work of Viswanadhan et al. (*Atomic physicochemical parameters for three dimensional structure directed quantitative structure-activity relationships. 4. Additional parameters for hydrophobic and dispersive interactions and their application for an automated superposition of certain naturally occurring nucleoside antibiotics,* 1989, J. Chem. Inf. Model, 29, 163-172), Log D vs. pH plots for several common catecholamines were created and utilized to better optimize clean-up conditions for UHPLC. Over the range of pH 2-4, lipophilicity remains stable for the compounds L-DOPA, dopamine, noradrenaline, adrenaline and serotonin. Within this pH, these listed compounds predominantly associate with the aqueous layer.

As validation of the recovery method, the recovery of isoproterenol, an isopropyl aminomethyl analog of adrenaline (epinephrine), often used as an internal standard for catecholamines, was tested by spiking the compound into sSIM, processing the medium by our recovery method and then performing an analysis by UHPLC-ECD. (−)-Isoproterenol hydrochloride (Sigma, Catalog Number 16504, St. Louis, Mo.) was spiked in 5 mL sSIM to yield final concentrations of 100 µg/mL, 10 µg/mL and 1 µg/mL. There is good agreement between our spiked concentration and measured concentration, with recovery being linear throughout the micromolar range (Table 2). The practical limits of detection are below 10 ng/mL (100 µg on column) for most catecholamines.

TABLE 2

| Mass isoproterenol spiked | Amount Recovered | % Agreement |
|---|---|---|
| 100 µg | 90.63 µg | 90.63 |
| 10 µg | 9.22 µg | 92.20 |
| 1 µg | 1.19 µg | 81.00 |

The production of several neurochemicals including dopamine and acetylcholine is supported by sSIM. The results highlight the importance of providing an appropriate environment possessing the resources likely to be available in vivo for the production of neurochemicals. Past attempts to obtain medium that simulate the gastrointestinal environment have included autoclaving gastrointestinal contents such as rumen contents or feces. A drawback to approaches that rely on in vivo acquired material is that this material has the potential to demonstrate variability dependent on host factors. sSIM is simulates the natural complexity while minimizing variability (see FIGS. 5A-5C).

Figure 5A:
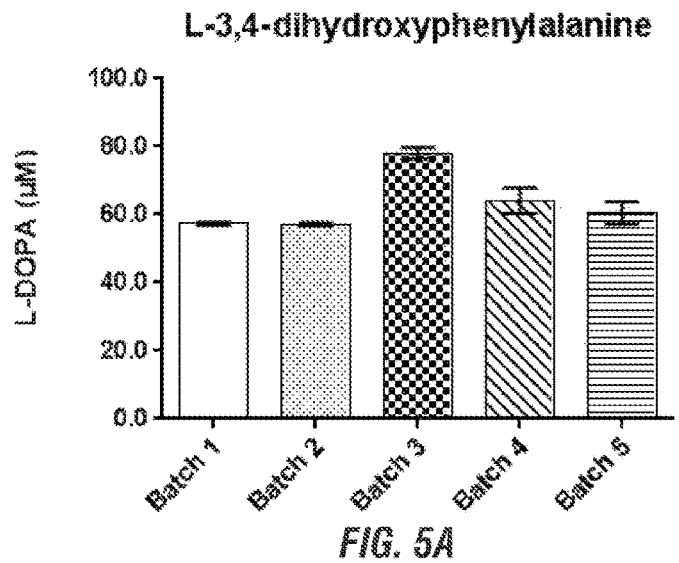
FIG. 5A is a graphical representation of the native abundance of L-DOPA found in sSIM across batch preparations.

Evaluation of the consistency of sSIM media show little real deviation among specific batches in relation to specific metabolites. As shown in FIG. 5A, with respect to L-DOPA, batch 1 measured 57.330 µM with a standard error of the mean (SEM) of 0.410 µM; batch 2: 57.15 µM (SEM: 0.42 µM); batch 3: 78.07 µM (SEM: 0.50 µM); batch 4: 64.10 µM (SEM: 1.20 µM); batch 5: 60.5 µM (SEM: 1.03 µM). The greatest deviation occurred in batch 3 which possessed a mean deviation of 30.7% relative to the mean of all other samples. All other samples fell within a mean deviation of 8% from the average mean.

Figure 5B:
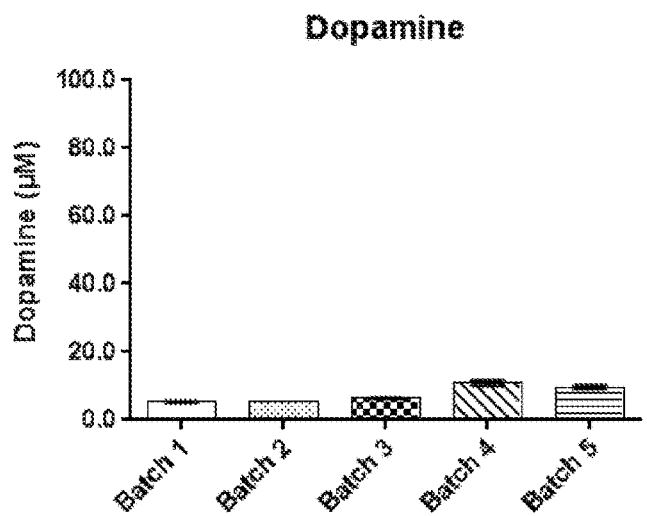
FIG. 5B is a graphical representation of the native abundance of dopamine found in sSIM across batch preparations.

As shown in FIG. 5B, dopamine in batch 1 measured 5.28 µM (SEM: 0.05 µM); batch 2: 5.38 µM (SEM: 0.04 µM); batch 3: 6.40 µM (SEM: 0.05 µM); batch 4: 10.86 µM (SEM 0.24 µM); batch 5: 9.66 µM (SEM: 0.15 µM). Batches four and five appeared distinct from batches 1 to 3, with batch four deviating 62.6% from the mean of all other batches.

Figure 5C:
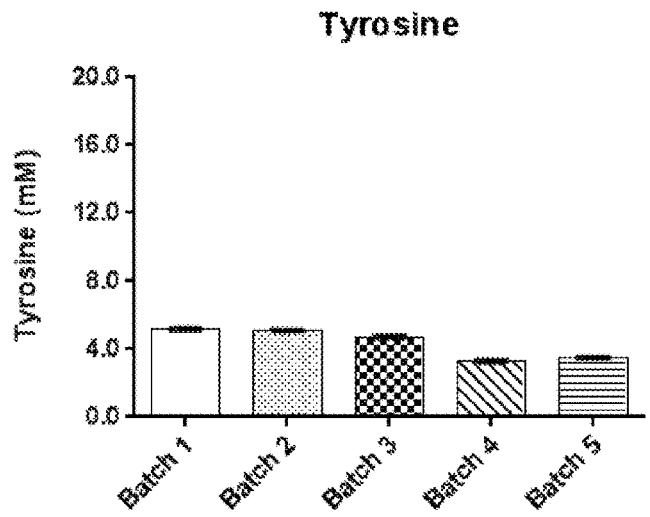
FIG. 5C is a graphical representation the native abundance of tyrosine found in sSIM across batch preparations.
Figure 6A:
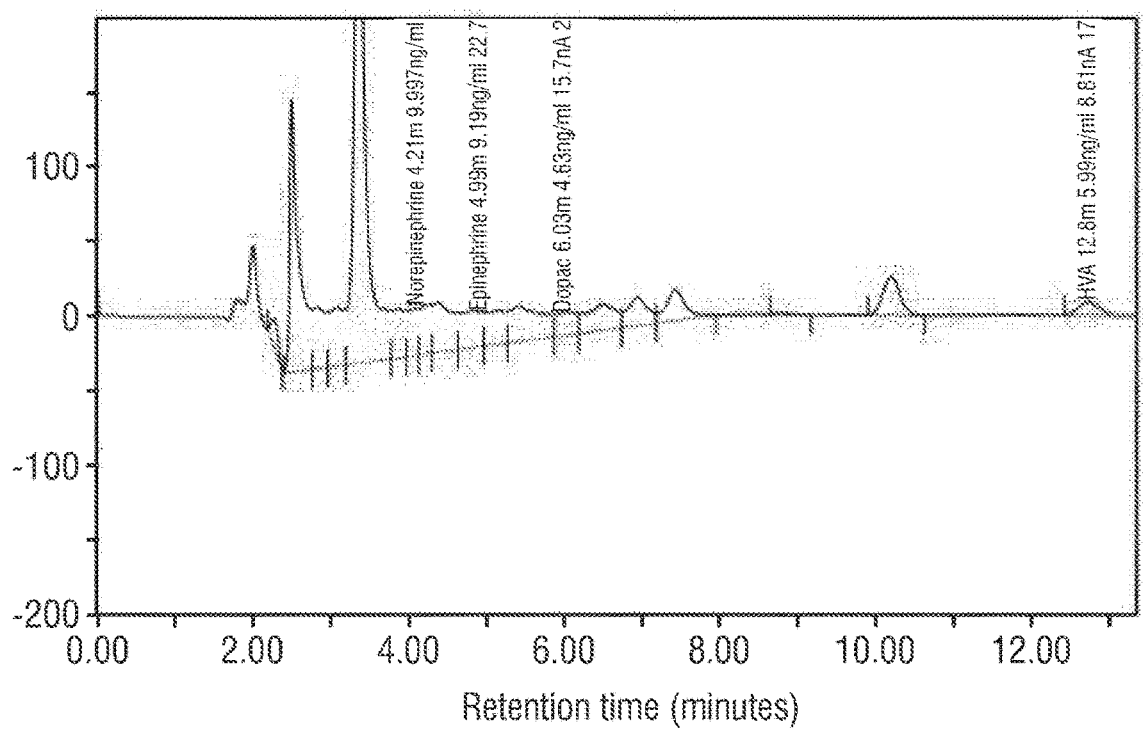
FIG. 6A is a graphical representation of electrochemical chromatographs of a control sample of sSIM without either *E. coli* or *E. faecium* or dopamine supplement.
Figure 6B:
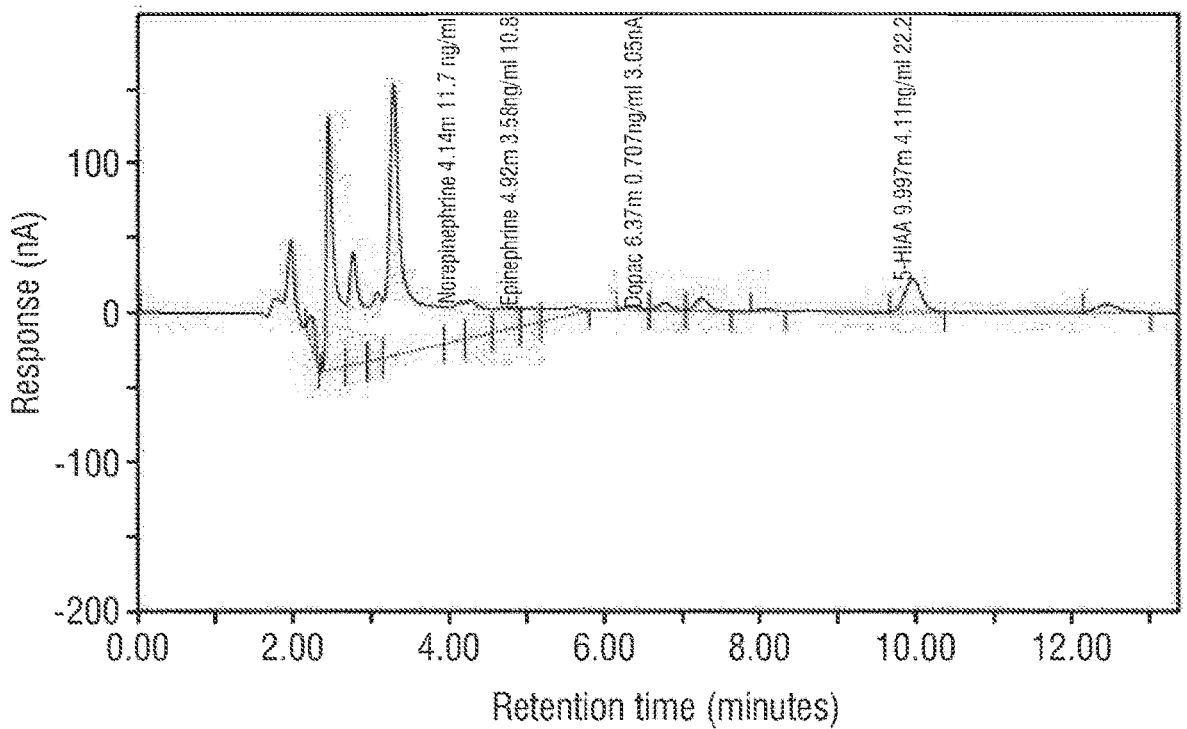
FIG. 6B is a graphical representation of electrochemical chromatographs of *E. coli* grown in sSIM without exogenous dopamine.
Figure 6C:
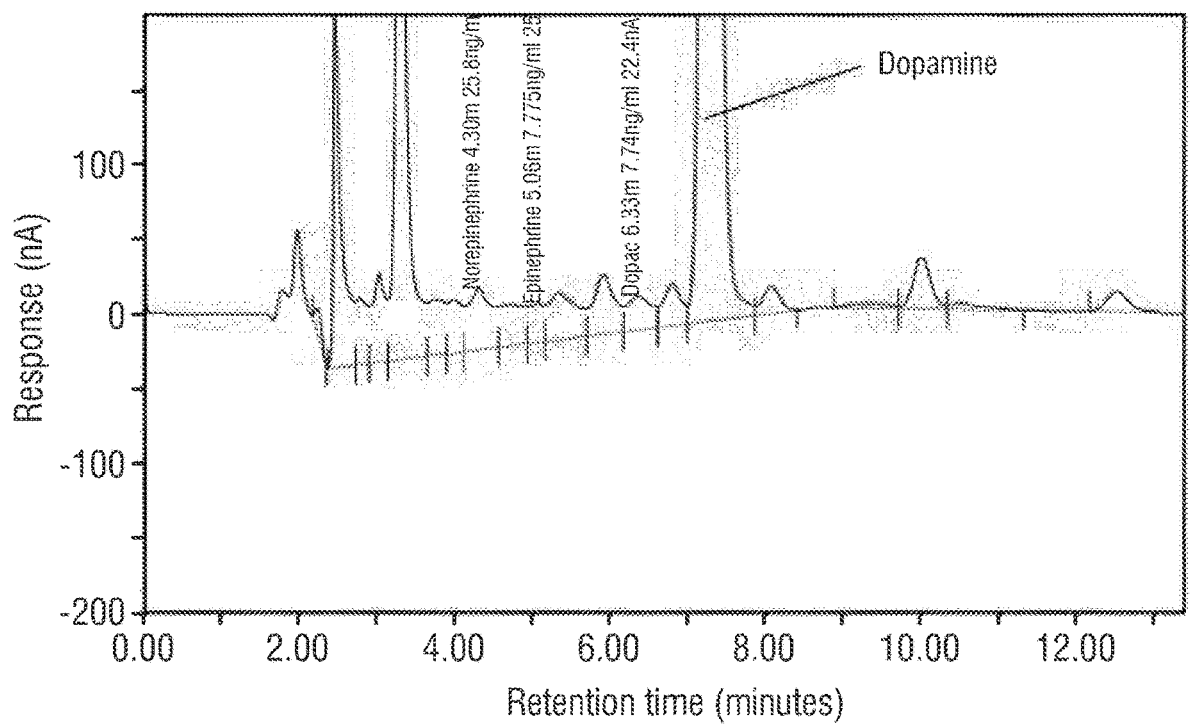
FIG. 6C is a graphical representation of a control of sSIM with 1 mM dopamine supplement without either *E. coli* or *E. faecium*, showing the detection of dopamine.
Figure 6D:
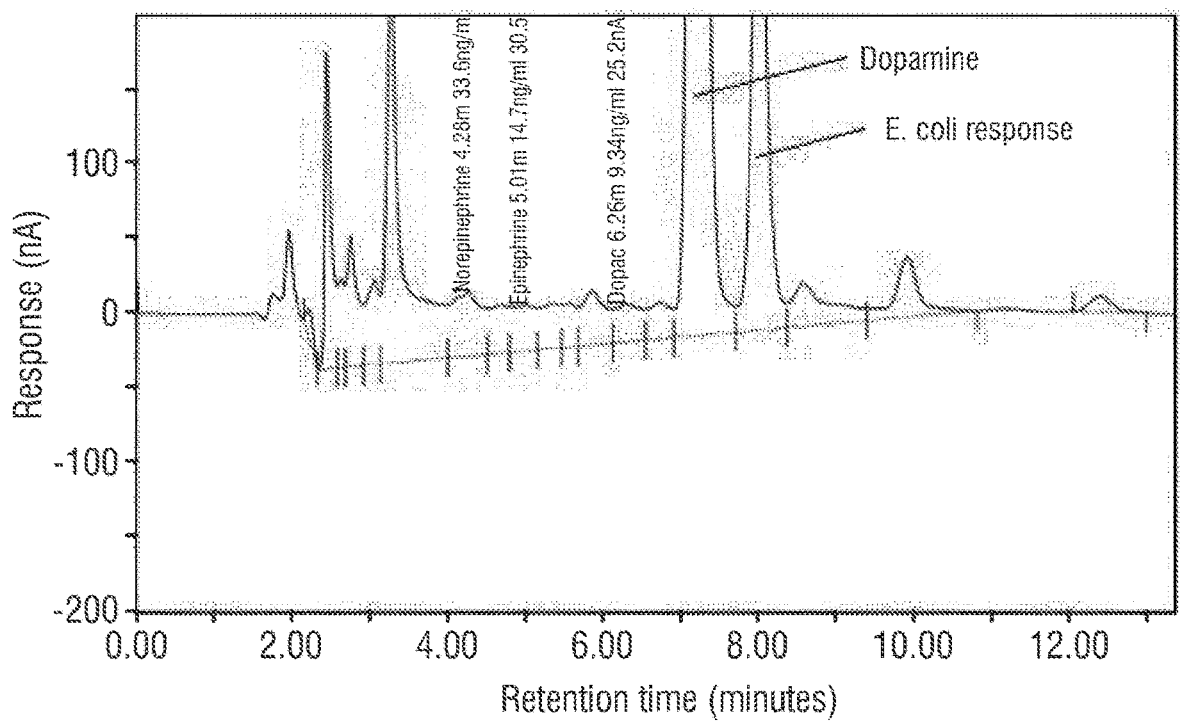
FIG. 6D is a graphical representation of *E. coli* grown in sSIM with 1 mM dopamine supplement, showing a response from *E. coli*.
Figure 6E:
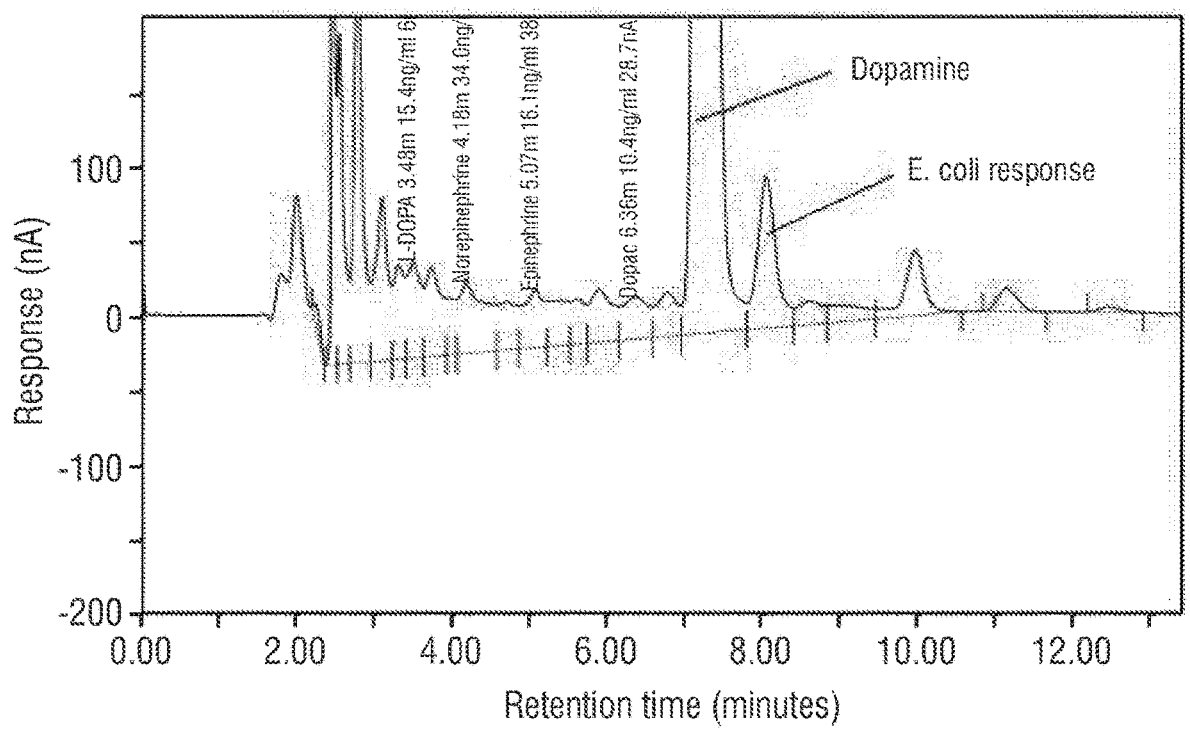
FIG. 6E is a graphical representation of a co-inoculation of *E. coli* and *E. faecium* in sSIM containing L-DOPA, but no dopamine supplement and showing a response similar to a monoculture of *E. coli* grown in the presence of dopamine.
Figure 6F:
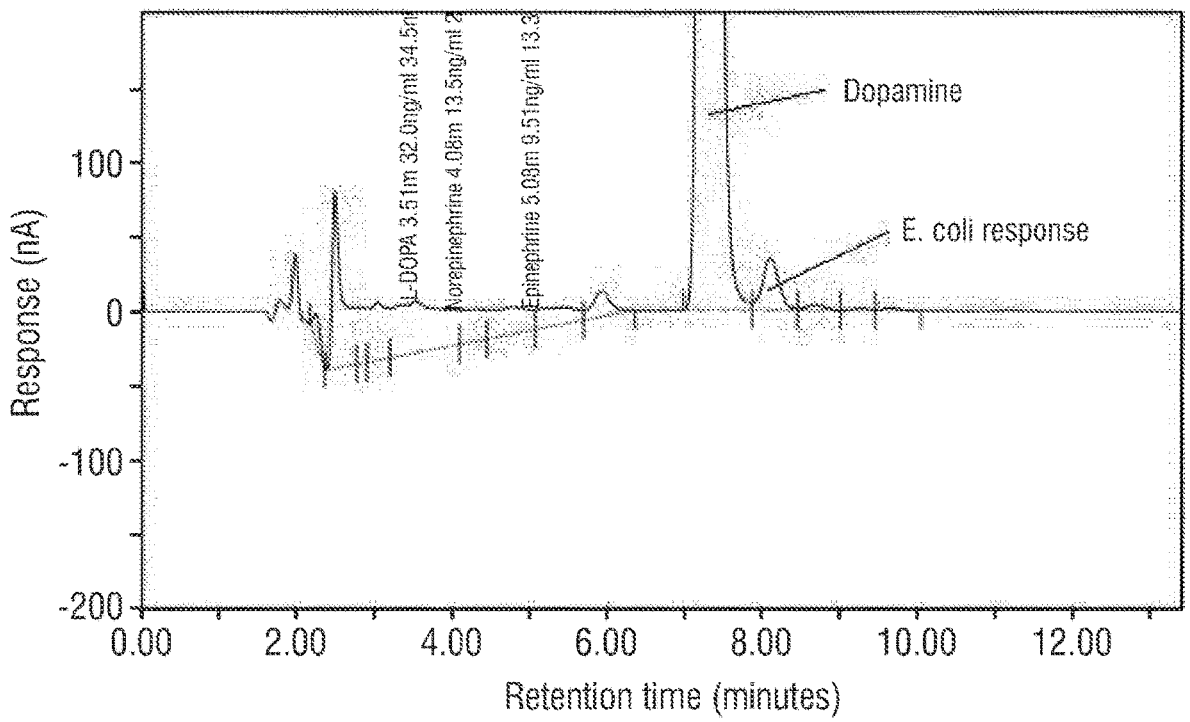
FIG. 6F is a graphical representation of *E. coli* grown in Luria Broth supplemented with 1 mM dopamine, showing a greatly reduced response by *E. coli* to the presence of dopamine than in sSIM.

As shown in FIG. 5C, the concentration of tyrosine in batch 1 measured 5.08 mM (SEM: 0.09 mM); batch 2: 5.11 mM (SEM: 0.07 mM); batch 3: 4.72 mM (SEM: 0.03 mM); batch 4: 3.29 mM (SEM: 0.03 mM); batch 5: 3.50 mM (SEM: 0.02 mM). Some of this deviation is due to the age of the starting material, as batches 4 and 5 used slightly older starting material than batches 1-3. The importance of these deviations will vary by application and the amounts present. For example, a batch with a 62.6% deviation in dopamine suggests a large deviation mathematically. However, this deviation results from only a 0.77 µg/L mass difference between batches and may not in fact be biologically important. Overall, our data demonstrates that acceptable reproducibility across batches can be achieved using the described methodology as was evidenced by the very low deviation between batches 1-3 (See FIGS. 5A-5C). Though sSIM is primarily an adaptation of the InfoGest Consensus Method (Mackie and Rigby, 2015), there are several important modifications which are important for a microbial medium. Unlike the original InfoGest Consensus Method, sSIM is supplemented with type III gastric mucin and hemin. Mucin can influence bacterial behavior in the gut. Fully processed, the medium contains 250 µg/mL of mucin and in vivo, mucin levels well in excess of this have been suggested. Since porphyrin bound iron is a required microbial factor for the growth of some enteric species such as *Prevotella intermedia*, 5 µg/mL (7.7 µM) hemin was supplemented. Porphyrins are naturally found in the GI tract as various breakdown products of heme and are excreted into GI tract via bile. Some examples include bilirubin or urobilinoid pigments which can be found in the stools of adults in these respective levels 5-20 mg/day and 50-250 mg/day.

Another key aspect of sSIM preparation is that the gastric and intestinal phases make use of a triple mix paddle blender. This is unlike InfoGest Consensus Method which relies on magnetic agitation. The more rigorous blending provided by the paddle blender approximates the mechanical forces of the stomach and also allows for a more homogeneous mixture.

Autoclaving sSIM can produce a usable medium, however much of the inherent digestive enzyme activity will be lost. To avoid enzymatic degradation, yet achieve conditions needed to produce a sterile medium, a cryogenic approach was used. This involved several cycles of flash freezing in liquid nitrogen followed by thawing under vacuum (750 mbar). As the medium thaws under vacuum, dissolved gasses such as oxygen bubble out of solution. This has the added advantage of making the medium suitable for anaerobic work. The medium is stored at −80° C. to limit further digestion by the enzymes present. Medium prepared in this manner shows no growth by direct microscopy or by broth and plate screens after five days.

Samples are first acidified to pH 3.0-3.3 using HCl. The pH range of 2-4 is ideal to work with for several reasons. Acidification causes a precipitation of many proteins which can interfere with passage through MWCO filters and subsequent electrochemical analysis. Within this pH range, the log D remains fairly constant for many catecholamines, including dopamine. This is also true of overall solubility (log S) for the majority of catecholamines as log S is higher at an acidic pH than it is at a neutral one. Within this pH range, overall recovery is consistent between samples even though pH values may differ slightly between samples. The acidic environment also disfavors oxidative processes which convert the catechol group of catecholamines to their respective quinones.

The results show that sSIM is a suitable medium to simulate the contents of the mammalian small intestine to utilize a microbial endocrinology approach. Beneficially, the combination of a simulated digestion medium with UHPLC-EC allows for a range of neurochemical experiments to be designed and conducted.

Example 5

To further test the dopamine production and conversion efficiency of additional probiotic strains, several additional strains were evaluated for ability to produce dopamine. An additional *Enterococcus, E. hirae* (ML1122), was evaluated along with *Vagococcus, V. fluvialis*, according to the methods in Example 2. The *E. hirae* utilized 100% of L-DOPA to dopamine. The results are shown in Table 3 and show exemplary conversion efficiency ranges of the probiotics which supplements the data set forth in Table 1.

TABLE 3

| Strain | Species | Avg. L-DOPA (μg/mL) | Avg. Dopamine (μg/mL) | L-DOPA Consumed (μg/mL) | Doiamine Produced (μg/mL) | Conversion Efficiency (%) |
|---|---|---|---|---|---|---|
| ML1122 | Enterococcus hirae | 0.0 | 73.5 | 143.0 | 71.5 | 64.4 |
| ML1113 | Vagococcus fluvialis | 75.5 | 23.8 | 67.6 | 21.8 | 19.6 |
| ML1114 | Vagococcus fluvialis | 89.0 | 9.9 | 54.0 | 7.9 | 7.1 |
| ML1115 | Vagococcus fluvialis | 87.0 | 8.7 | 56.0 | 6.7 | 6.0 |

Example 6

Dopamine has been documented as capable of influencing the growth profile of organisms like E. coli and as sSIM better simulates an intestinal environment, sSIM was inoculate with E. coli and spiked with 0.001 M dopamine in order to test for the effects of dopamine in a gastrointestinal setting on E. coli. As shown in FIGS. 6A-6F, a novel chemical response by E. coli to dopamine was detected. Dopamine has been documented as capable of influencing the growth profile of organisms like E. coli. Although this is a well-established finding, the chemical-mechanistic effects of catecholamines on prokaryotes are relatively poorly understood. Neurochemical exposure has the potential not only to alter growth profiles and behavior, but it also appears to trigger the production of unique chemicals. Isocratic separation using high performance liquid chromatography followed by electrochemical detection demonstrates one such example. E. coli grown in the presence of dopamine produces a distinct chromatographic signal which is representative of a distinct chemical. Likely this signal represents a distinct catecholamine derivative.

Vicinal hydroxyl groups, particularly cis diols such as those in the aromatic ring of catecholamines, are known to possess a strong affinity for boronate. It has been determined that the chemical produced by E. coli in response to dopamine possesses this affinity. Liquid separation followed by solid phase extraction using affinity columns containing boronate (Biorad: Affigel boronate beads) has demonstrated that the chemical produced by E. coli in response to dopamine binds boronate. Likely, this is indicative of the presence of a cis diol group which supports the theory that the chemical is a derivative of dopamine. Although other biological chemicals besides catecholamines are known to possess cis-diol groups, the appearance of this peak following the administration of a catecholamine disfavors that argument.

Given the complexity of the sSIM, it is perhaps not surprising that this response is distinctly different from what is observed in a basic medium like LB. E. coli grown in LB supplied with dopamine produces little if any of this compound, as evidenced in FIG. 6F. LB may lack a necessary cofactor or the environment of sSIM allows for the expression of this unique behavior. Identification of this peak by attempting to match its retention time to that of other known catecholamine derivatives has so far not yielded any matches. Unique or not, this distinct behavior demonstrates the importance of using a more natural and complex media like sSIM in which responses like this can be observed. It is conceivable that this is a completely novel product not previously observed from E. coli because of the complex media.

Example 7

Additional data was obtained to demonstrate the industrial production of dopamine utilizing various media augmented with the neurotransmitter precursor L-DOPA. As shown in Table 4, significant levels of dopamine can be provided in commercially-available laboratory media in addition to the sSIM disclosed herein.

TABLE 4

| | Media (Augmented by L-DOPA prebiotic) | Average Dopamine Made (μg/mL) | Average Conversion Efficiency (%) |
|---|---|---|---|
| Strain ML1082 | TSB | 57 | 25% |
| | LB | 44 | 20% |
| | BHI | 54 | 24% |
| | MRS | 13 | 6% |
| Strain ML1086 | TSB | 68 | 30% |
| | LB | 43 | 19% |
| | BHI | 69 | 30% |
| | MRS | 55 | 24% |
| Strain ML1087 | TSB | 14 | 6% |
| | LB | 16 | 7% |
| | BHI | 8 | 3% |
| | MRS | 7 | 3% |
| Strain ML1089 | TSB | 44 | 19% |
| | LB | 20 | 9% |
| | BHI | 48 | 21% |
| | MRS | 28 | 12% |

As shown, several E. faecium strains were inoculated into broths supplemented with the prebiotic L-DOPA at 100 μM at approximately 5×10⁶ CFU/mL of broth. Following 24 hours of static culture at 37° C. the amount of dopamine produced by the individual strains into the culture medium was assessed using UHPLC-ECD. The media are as follows: TSB, tryptic soy broth; LB, Luria-Bertani broth; BHI, Brain-Heart Infusion broth; and MRS, deMan, Rogosa and Sharpe Lactobacilli broth.

However, when compared with Table 1, it can be seen that, except for the low producing strain ML1087, the production and conversion of the other strains is far lower in the commercial media than in sSIM. This shows that while the commercial media may be used, probiotic strains can produce more dopamine in sSIM.

Example 8

To test the production of another neurotransmitter, tyrosine, in sSIM three strains of E. faecium, ML1085, ML1087, and ML1089 (isolated from canine urine, feline urine and canine bile; respectively), were grown overnight at 37° C. anaerobically on TSA with 5% ovine blood. Colonies from each strain were suspended in peptone water and standardized to an $OD_{600}$ of 0.20. Cultures with an initial population density on the order of 6 to 7 logs per milliliter were prepared by inoculating 25 mL of sSIM with 500 µL of suspension. These samples were then grown at 37° C. anaerobically with agitation. Initially, and for every four hours over a 24-hour period, 1 mL of material was removed from each culture for neurochemical analysis by UHPLC-ECD and plate counts. Sampling was done in duplicate.

Figure 7A:
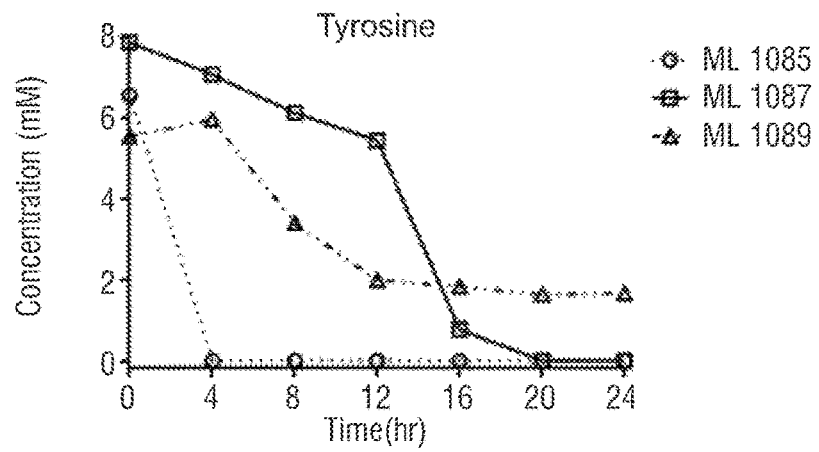
FIG. 7A is a graphical representation of the use of tyrosine over time by three strains of *E. faecium* grown in sSIM.
Figure 7B:
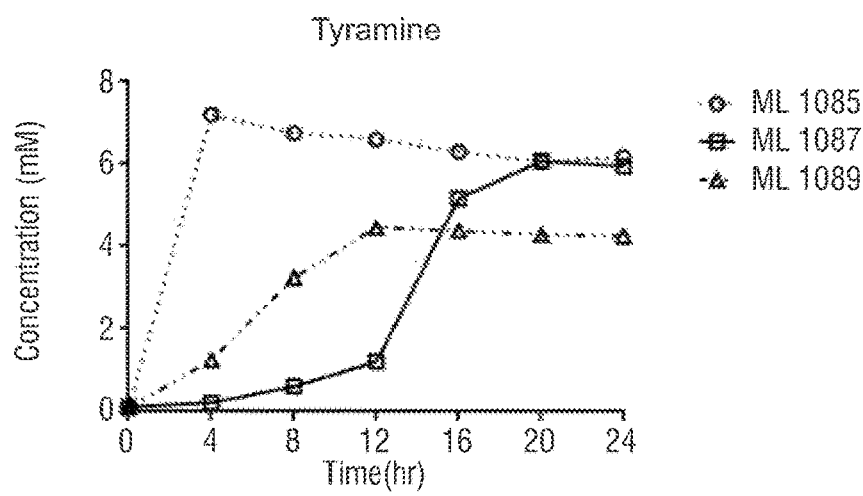
FIG. 7B is a graphical representation of the production of tyramine over time by three strains of *E. faecium* grown in sSIM.
Figure 7C:
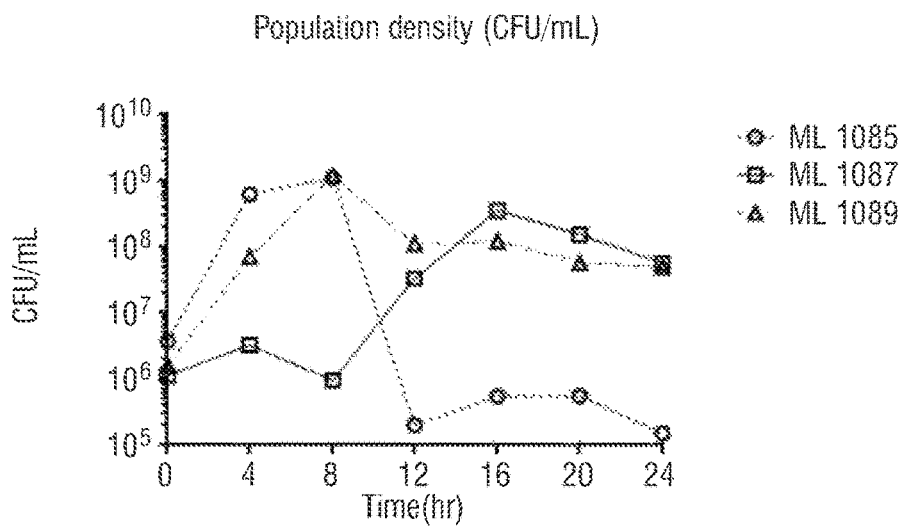
FIG. 7C is a graphical representation of the population density over time by three strains of *E. faecium* grown in sSIM.
Figure 9A:
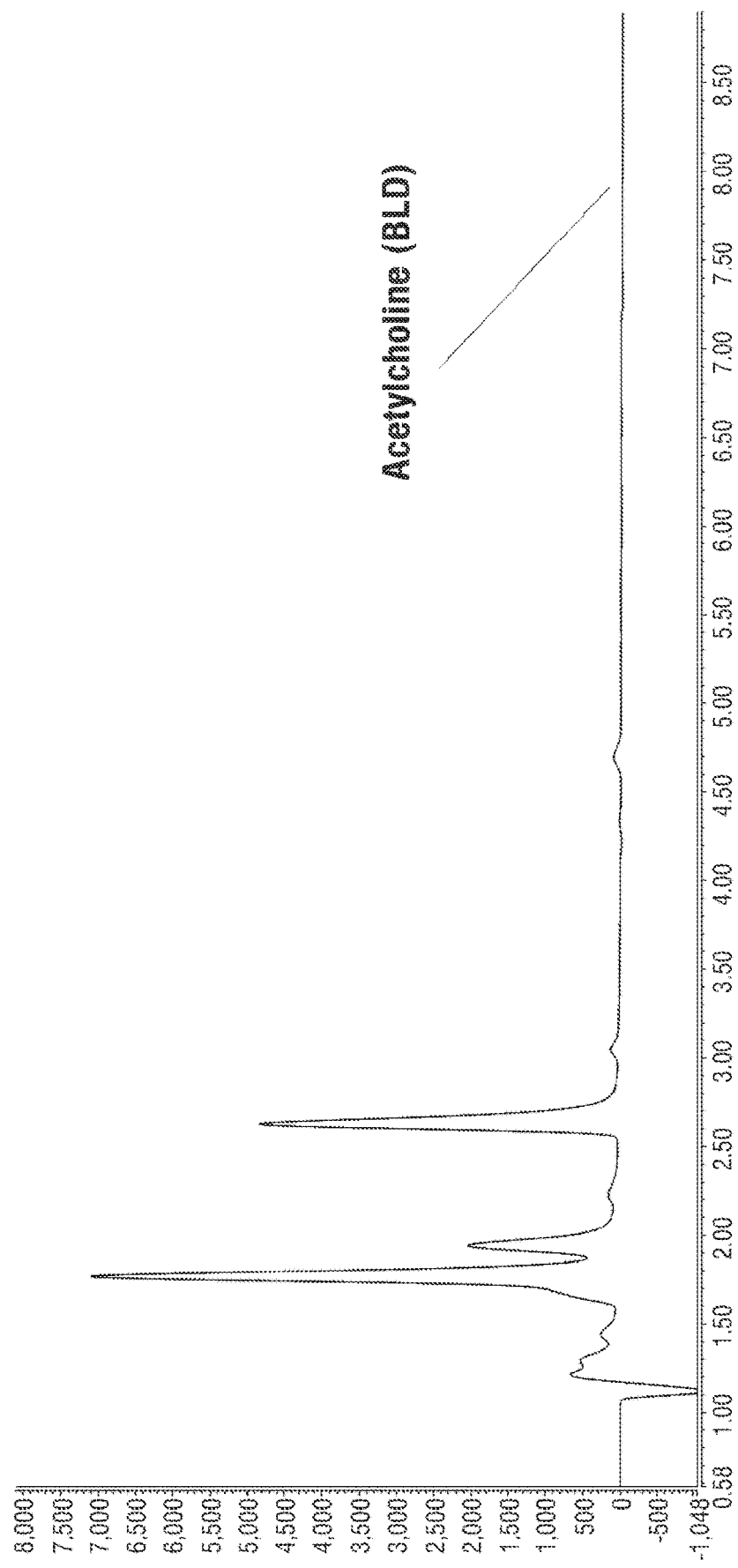
FIG. 9A is a graphical representation of the levels of dopamine and L-DOPA for multiple strains of *E. faecium* grown in BHI broth supplemented with L-DOPA compared to an uninoculated control.

As shown in FIG. 7A, ML1085 demonstrated the most rapid utilization of tyrosine, reaching complete tyrosine utilization and the highest level of tyramine reported by 4 hours (FIG. 7B). ML1087 exhibited a classic sigmoidal growth pattern with population density reaching a maximal point by 16 hours, far later than either other strain (FIG. 7C). Tyrosine utilization and tyramine accumulation changed marginally over the first twelve hours and then rapidly changed during the period of logarithmic growth. ML1089 reached a peak population of $10^9$ CFU/mL by 8 hours (FIG. 7C). Unlike ML1085, the strain ML1089 only underwent a marginal loss of population, subsisting at levels around $10^8$ CFU/mL for the remainder of the experiment (FIG. 7C). Although ML1089 subsisted and reached population levels matching or exceeding the highest observed in ML1085 or ML1087, the utilization of tyrosine to make tyramine was never exhaustive. Maximal conversion occurred by 12 hours and remained constant for the remainder of the experiment.

This shows that other neurotransmitters may be produced in place of or in addition to dopamine using sSIM.

Example 9

The production of another neurotransmitter, acetylcholine, in sSIM by Lactobacilli isolates was also tested. Multiple Lactobacilli isolates, including *Lactobacillus plantarum*, were recovered from the environment and screened for the production of acetylcholine in sSIM as described above. Isolated organisms were grown overnight, at 37° C. anaerobically on TSA blood with 5% ovine blood. Colonies from each strain were suspended in peptone water and standardized to an $OD_{600}$ of 0.20. Cultures were prepared by inoculating 5 mL of sSIM with 100 µL of peptone suspension and then incubated at 37° C. anaerobically with agitation. After 24 hours, the material was processed for analysis of acetylcholine by UHPLC-ECD, specifically the approach used for acetylcholine as discussed above. Each organism was cultured and analyzed in triplicate. Of the organisms tested, only *L. plantarum* demonstrated significant acetylcholine production and was used for subsequent examination.

Figure 8B:
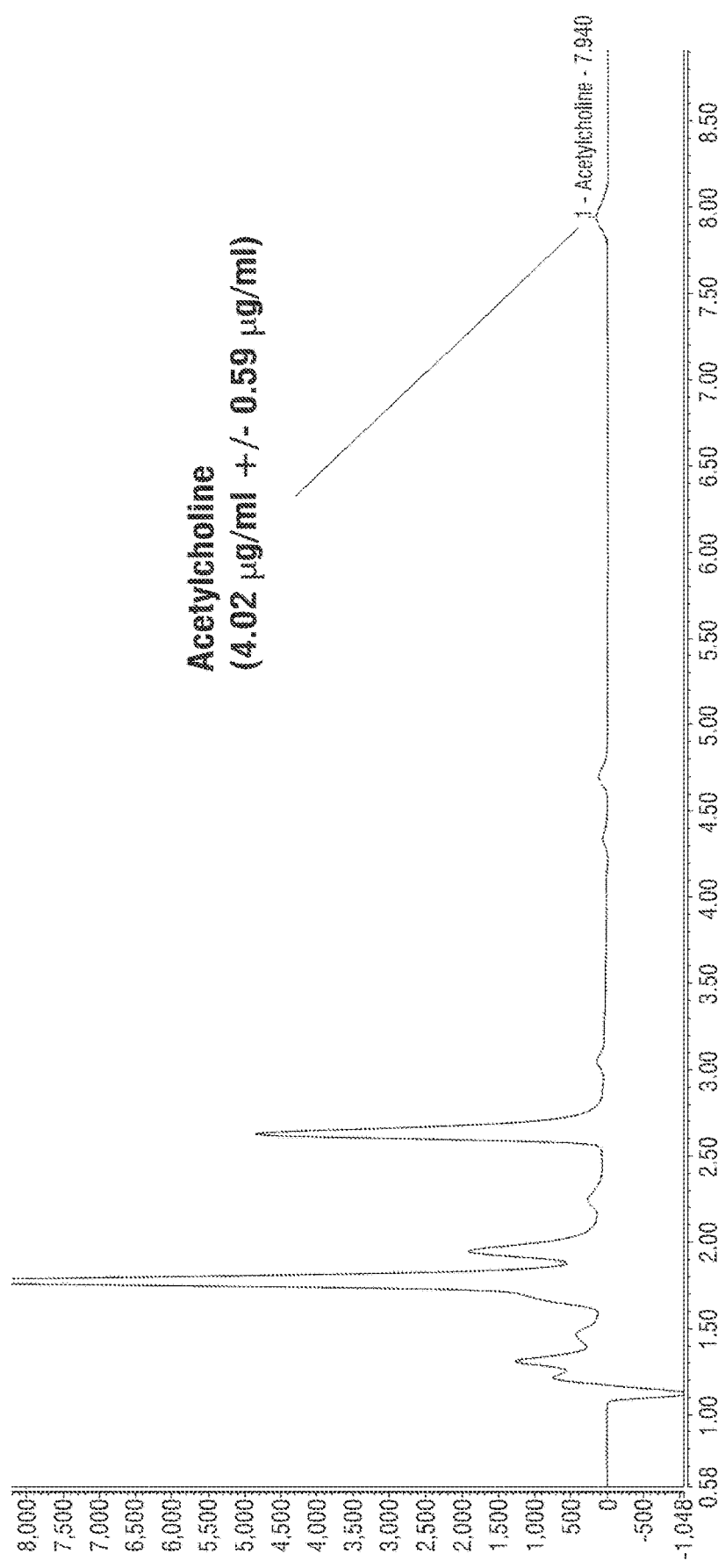
FIG. 8 is a graphical representation of acetylcholine in sSIM with or without an inoculation of *L. plantarum* showing the production of acetylcholine from choline in the presence of *L. plantarum*.
Figure 9A:
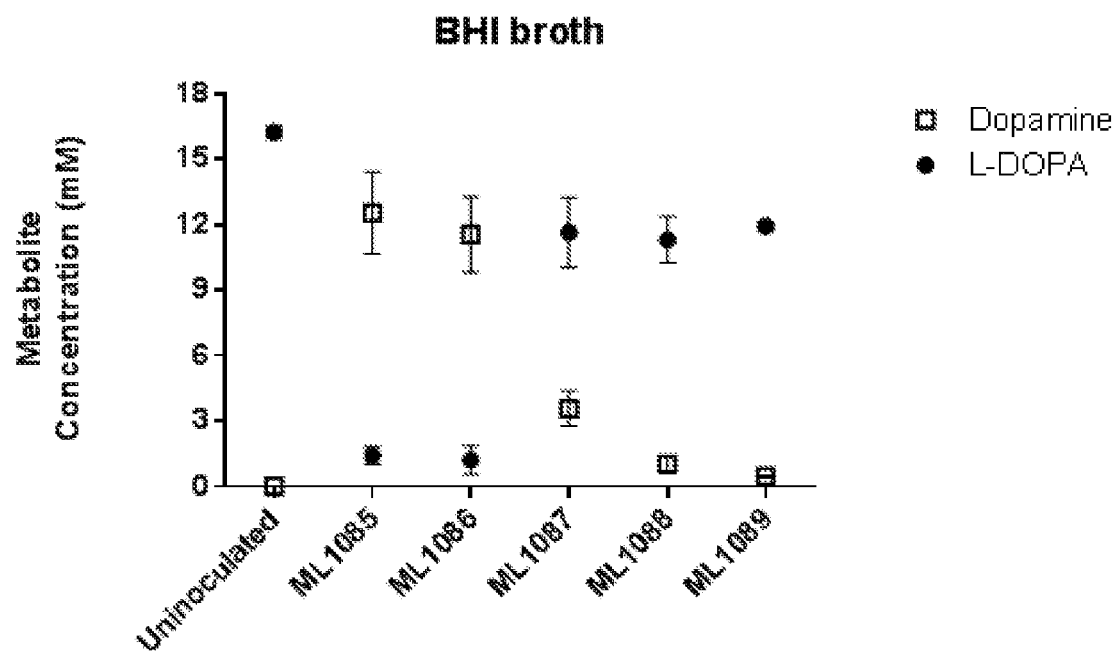
Figure 9B:
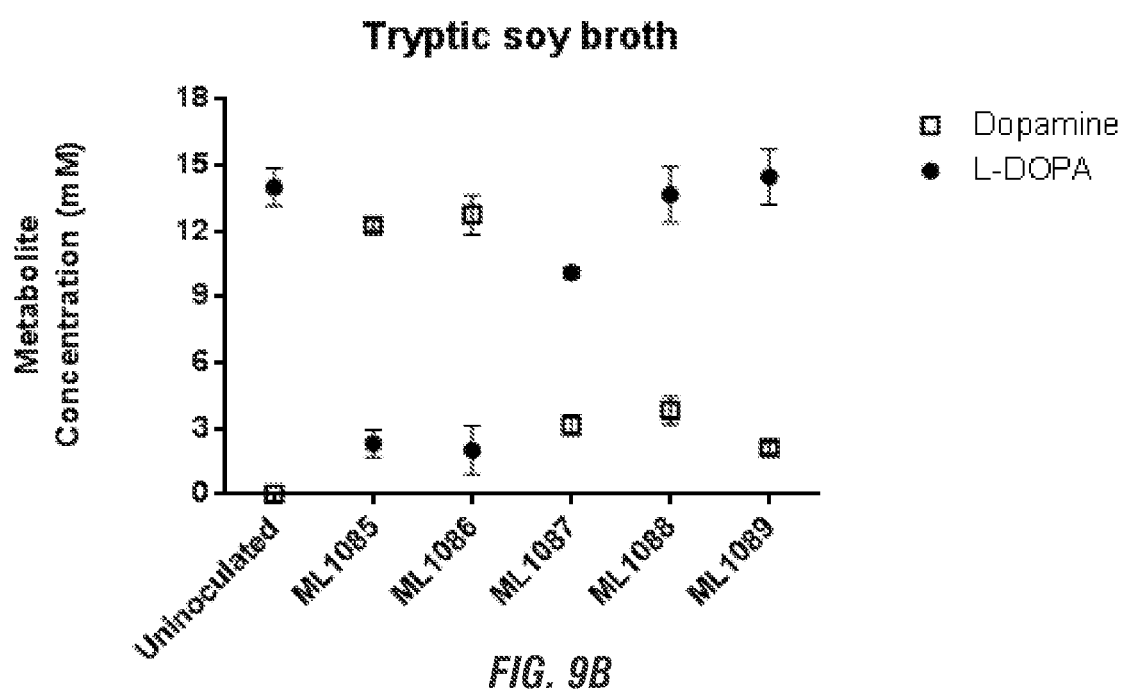
FIG. 9B is a graphical representation of the levels of dopamine and L-DOPA for multiple strains of *E. faecium* grown in Tryptic soy broth supplemented with L-DOPA compared to an uninoculated control.
Figure 9C:
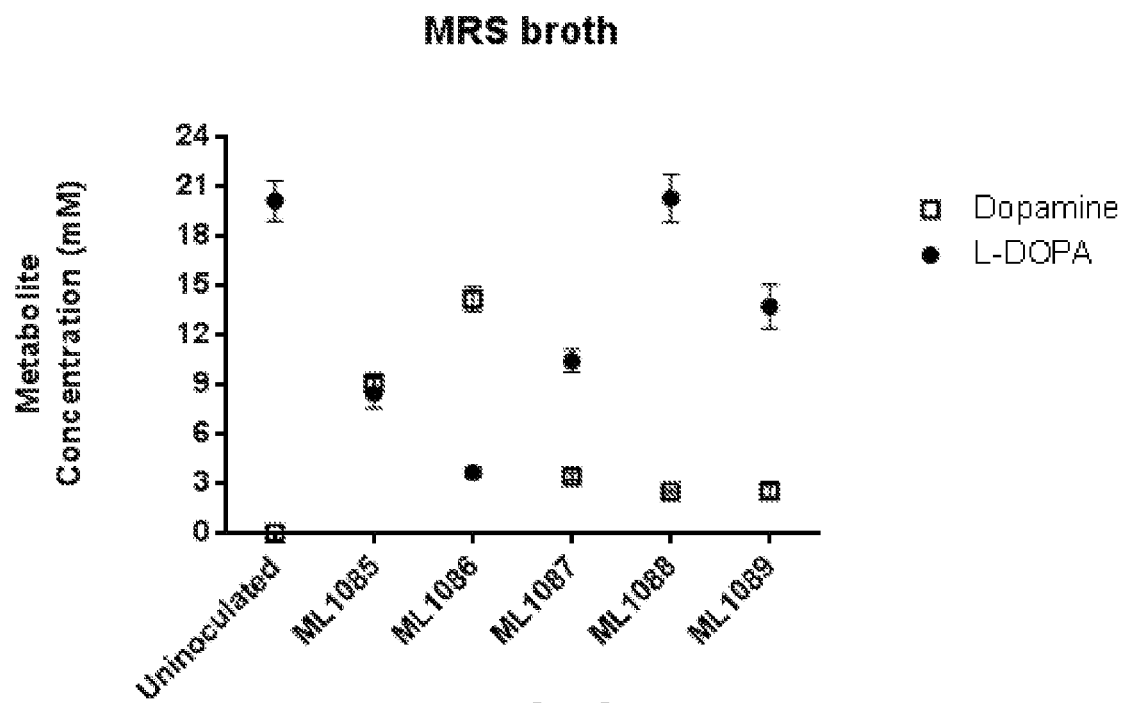
FIG. 9C is a graphical representation of the levels of dopamine and L-DOPA for multiple strains of *E. faecium* grown in MRS broth supplemented with L-DOPA compared to an uninoculated control.
Figure 9D:
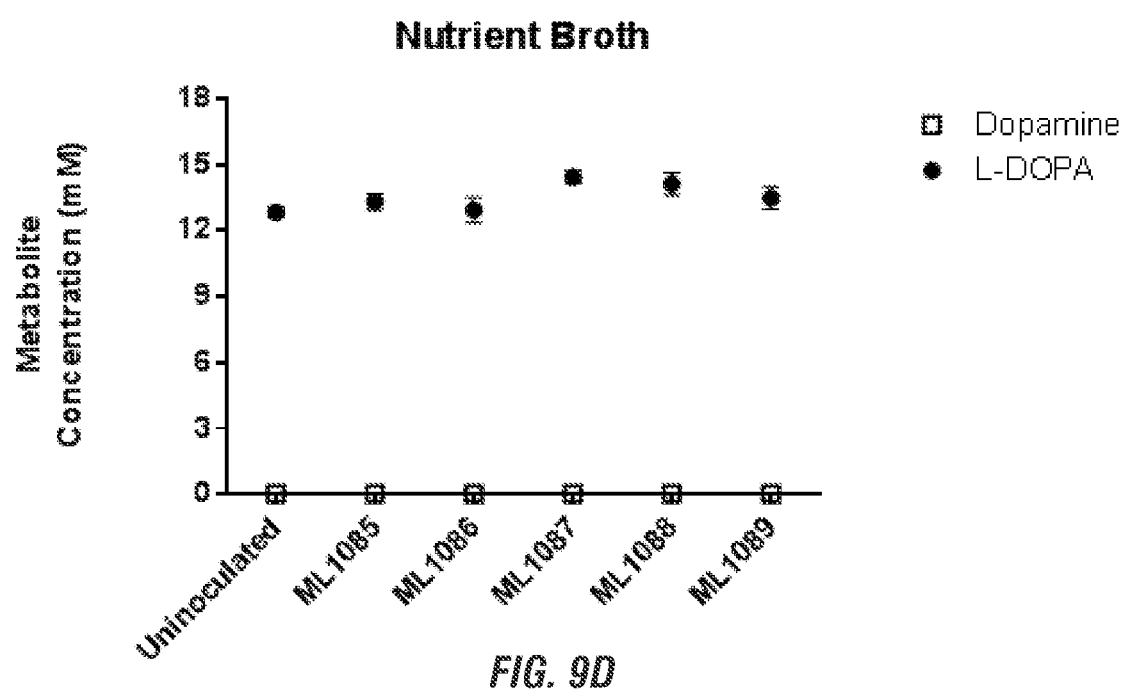
FIG. 9D is a graphical representation of the levels of dopamine and L-DOPA for multiple strains of *E. faecium* grown in Nutrient Broth supplemented with L-DOPA compared to an uninoculated control.
Figure 9E:
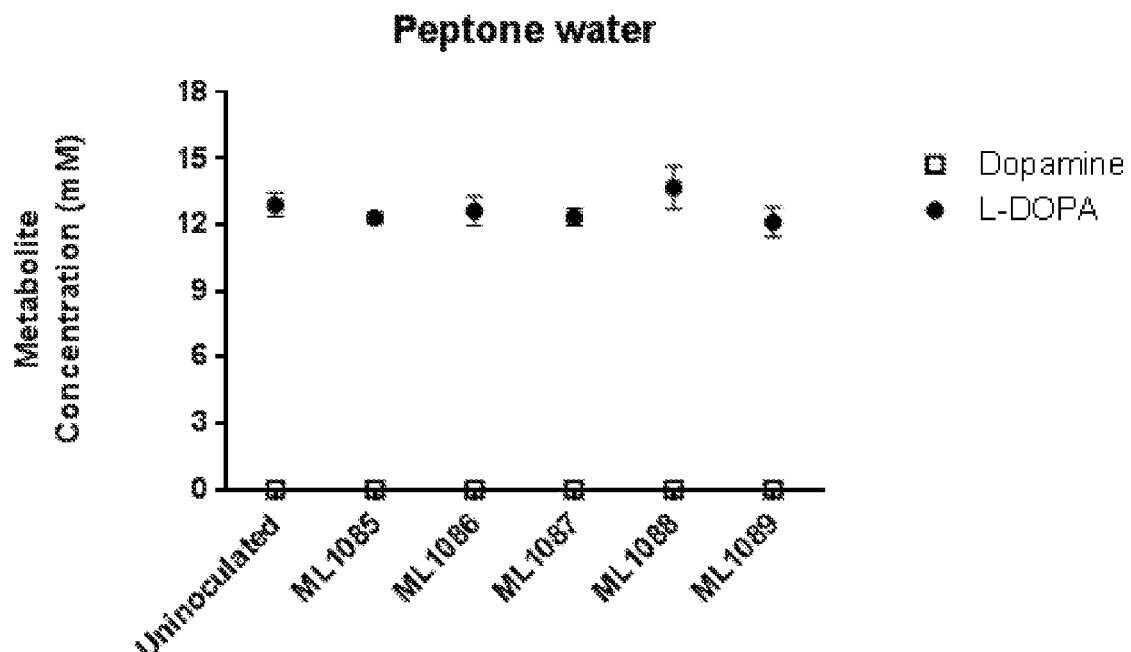
FIG. 9E is a graphical representation of the levels of dopamine and L-DOPA for multiple strains of *E. faecium* grown in Peptone water supplemented with L-DOPA compared to an uninoculated control.
Figure 9F:
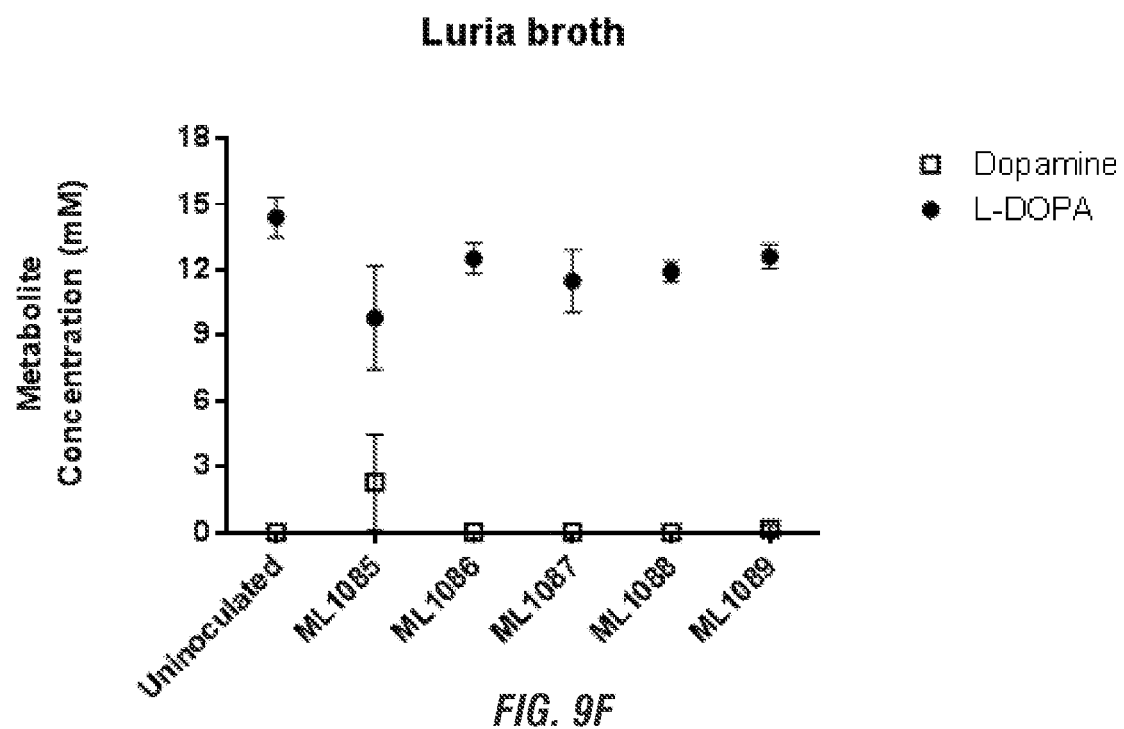
FIG. 9F is a graphical representation of the levels of dopamine and L-DOPA for multiple strains of *E. faecium* grown in Luria broth supplemented with L-DOPA compared to an uninoculated control.

*L. plantarum* has been documented to produce acetylcholine when cultured in a medium which supplies key chemicals including pantothenic acid. As shown in FIG. 8B, in sSIM, *L. plantarum* produced an average of 4.02 µg/mL of acetylcholine with a standard error of the mean of 0.59 µg/mL. The amount of acetylcholine produced in sSIM is consistent with what has been reported previously, in which the organism was reported to produce 4.8 µg/mL acetylcholine in a peptone-based media supplemented with pantothenic acid. As such, the use of sSIM and the biochemical environment it represents supports the production of acetylcholine by *L. plantarum*.

Example 10

To determine if there is a dose response of dopamine production in sSIM by *E. faecium*, the L-DOPA concentration of the media was varied in a concentration-dependent manner. The diet containing 7.5% *Mucuna* powder (by dry weight) was prepared by mixing 4.9 g of *Mucuna* powder (Transformational Foods, Santa Barbara, Calif., USA) with 60 grams of feed (Teklad Global Diet #2019S, Envigo, Madison, Wis., USA). The entirety of this mixture was digested per the in vitro digestion technique in Example 4. The product *Mucuna* media was subsequently diluted with media not containing *Mucuna* to create a variety of L-DOPA concentrations. The *E. faecium* strain ML1082 was grown anaerobically for 24 hours on TSA agar with 5% ovine blood. Following plate growth, colonies were suspended in peptone water to make standardized suspensions with an $OD_{600}$ measurement of 0.200 (+/−0.005). Inoculation was achieved by mixing 4.9 mL of media with 100 µL of bacterial suspension. Inoculated samples were grown for 24 hours at 37° C., anaerobically while being subjected to low speed (100 rpm) magnetic stir bar mixing. Samples were then processed by a standardized approach for catecholamines. All conditions were run in triplicate.

In a diet derived solely from lab feed, L-DOPA availability permits the production of approximately 70 µM of dopamine by the strain ML1082. When the dry weight of the feed digested consisted of 0.15% *Mucuna*, dopamine production reached over 100 µM, a diet of 1.5% *Mucuna* allowed dopamine production in excess of 350 µM and dopamine production reached 1500 µM with a diet of 7.5% *Mucuna* (see Table 5). Therefore, strain ML1082 shows a dosage dependent production of dopamine. This may also help in the treatment of a subject in that both the strain and the amount of precursor, such as L-DOPA, may both be used to fine tune administration of a treatment.

TABLE 5

| Growth Media | L-DOPA Available (µM) | L-DOPA Utilized (µM) | Dopamine Produced (µM) |
|---|---|---|---|
| Diet with 7.5% Mucuna | 2172 | 2143 | 1563 |
| Diet with 1.5% Mucuna | 497 | 489 | 358 |
| Diet with 0.15% Mucuna | 143 | 142 | 101 |
| Unsupplemented media | 90 | 89 | 71 |
| Media with 1 mM L-DOPA | 934 | 926 | 721 |

Example 11

To further test the ability of several strains of *E. faecium* to produce dopamine, strains were grown in a number of different commercially available media spiked with a maximal dosage of L-DOPA to avoid any possible ceiling effect if a strain was capable of effectively converting all the L-DOPA in the media into dopamine. In order to provide a maximum amount of L-DOPA that could be consumed in 24-hours without waste, one of the most productive strains of *E. faecium*, ML1082, was provided a great excess of L-DOPA in the media, amounting to 20 mM, plus what is available in the sSIM media. The total amount of L-DOPA remaining after 24 hours was determined as above using UHPLC-ECD. About half of the available 20 mM L-DOPA was utilized (data not shown), indicating that strain ML1082 was able to consume around 10 mM of L-DOPA without waste.

Six different commercially available media were assayed for bacterial production of dopamine: Luria Broth, MRS, Tryptic Soy Broth, BHI, Nutrient Broth, and peptone water. L-DOPA was prepared by using a minimal about of acid to dissolve all the L-DOPA. L-DOPA was dissolved into HPLC grade water in the amount of 1.97 grams of L-DOPA into 7.5 mL HPLC grade water with the addition of 1.25 mL of 10N HCl to yield a total volume of 10 mL. One hundred microliters of this L-DOPA solution was added to a total volume of 10 mL of each of the media tested to yield the target 10 mM.

Five strains of Enterococcus faecium, ML1085, ML1086, ML1087, ML1088, and ML1089, were grown in triplicate in the commercially available media with 10 mL L-DOPA. To inoculate, strains were grown aerobically, at 37° C., overnight on TSA agar plates containing 5% ovine blood. Cells were harvested and suspended in peptone water to achieve standard inoculation densities of 0.2 $OD_{600}$. 100 µl of each respective suspension was used to inoculate 10 mL of media. Uninoculated tubes of the respective supplemented media were used as controls. Tubes were grown without agitation for 24 hours, aerobically at 37° C. At 24 hours, broth cultures were acidified with the addition of 100 µL of 10N HCl. Acidified cultures were centrifuged at 3000×G, for 15 minutes at 4° C. to remove cells and denatured proteins. The supernatant was transferred to 3 kDa molecular weight cut off filter tubes and filtered by centrifugal force provided at 4300×G, at 4° C. Aliquots of respective samples were diluted 1000× into mobile phase and tested by UHPLC-ECD. Remaining sample partitions were stored at −80° C.

As shown in FIGS. 9A-9F and summarized in Table 6, only strains ML1085 and ML1086 produced a significant amount of dopamine in at least one of the commercial medium, specifically: BHI broth, Tryptic soy broth, and MRS broth. No appreciable amount of dopamine was produced in Nutrient Broth, peptone water, or Luria broth by any strain. Strains ML1087, ML1088, and ML1089 produced little to not dopamine in any of the commercial mediums.

Therefore, even within the same species and across different media types, the production of dopamine is highly variable. This shows the importance of screening bacteria for their ability to produce dopamine before using them in synbiotic compositions. The screen may allow the formulations of compositions of different levels of dopamine production. For example, E. faecium strain ML1085 may form high dopamine synbiotics while E. faecium strain ML1087 may form low dopamine synbiotics. The L-DOPA level in the synbiotics could also be adjusted to the strain to minimize excess L-DOPA in the synbiotic.

TABLE 6

| Media | Strain | Unused L-DOPA (Average µg/mL) | L-DOPA Consumed (Average µg/mL) | Dopamine Produced (Average µg/mL) | Conversion Efficiency (Average %) |
|---|---|---|---|---|---|
| BHI Broth | ML1085 | 279 | 2922 | 1921 | 77 |
|  | ML1086 | 239 | 2962 | 1768 | 71 |
|  | ML1087 | 2296 | 905 | 547 | 22 |
|  | ML1088 | 2230 | 971 | 155 | 6 |
|  | ML1089 | 2351 | 850 | 71 | 3 |
| TSB | ML1085 | 454 | 2303 | 1875 | 88 |
|  | ML1086 | 396 | 2361 | 1949 | 91 |
|  | ML1087 | 1988 | 770 | 483 | 23 |
|  | ML1088 | 2690 | 67 | 585 | 27 |
|  | ML1089 | 2658 | 100 | 294 | 14 |
| MRS | ML1085 | 1673 | 2299 | 1392 | 45 |
|  | ML1086 | 728 | 3244 | 2173 | 70 |
|  | ML1087 | 2062 | 1910 | 531 | 17 |
|  | ML1088 | 3734 | 238 | 382 | 12 |
|  | ML1089 | 2711 | 1261 | 394 | 13 |

Example 12

In vivo, the production of dopamine in various tissues from mice was also assessed using a gavage of E. faecium strain ML1082 with feed. For the synbiotic groups, the feed was supplemented with either a high L-DOPA containing food source, Mucuna powder, or purified L-DOPA (Sigma).

The gavage was prepared by culturing ML1082 until an $OD_{600}$ of 0.2 was achieved in peptone/20% glycerol was achieved. This culture was then inoculated in a 1:50 ratio of BHI media. The inoculated BHI was grown for 6 hours, aerobically, at 37° C. to correspond to the middle of the log phase of growth. The BHI was supplemented with 0.02 mg/mL of purified L-DOPA (about 1 mM L-DOPA). Culture population was measured at $OD_{600}$. Following culture, the cells were washed by centrifugation at 3,000×g for 10 minutes to pellet the cells followed by resuspension in PBS. Washing was performed twice. Cells were then pelleted and resuspended in PBS to create suspension of $5\times10^9$ CFU/mL calculated based on the $OD_{600}$ readings. This produces a gavage of $1\times10^9$ CFU/200 solution.

Feed was prepared in one of two ways depending on the source of L-DOPA. For supplementing with Mucuna powder, 12 g of 12.6 mg/g L-DOPA Mucuna powder was mixed with granulated feed to achieve a final concentration of about 0.5 mg/g L-DOPA feed. For purified L-DOPA, 1 g of purified L-DOPA is mixed in a 1:200 ratio with the feed powder. The mixed feed is then added to additional feed powder in a 1:4 ratio, creating a 1 mg/g L-DOPA feed.

Feed and gavages were prepared daily and fed/administered to the different groups of mice for either a 7-day trial or a 12-day trial. For the 7-day trial, 10 mice were in each of the control group given normal feed plus a PBS gavage, the ML1082 probiotic gavage with normal feed, and ML1082 gavage plus Mucuna powder supplemented feed group. Mice were fed ad libitum and gavaged with a 200 µL aliquot of either PBS or ML1082 (about $1\times10^9$ CFU) in PBS for 7 days. On days 5 and 7, behavioral studies were performed on the mice (see below). Mice were sacrificed on day 8 and organs harvested and blood taken. Additionally, fecal samples and body weight were collected from clean cages at day −2, −1, and every other day starting at day 0. Tissues collected were brain, duodenum, jejunum, ileum, cecum, cecal contents, proximal colon, distal colon, liver, lungs and blood. Liver, lungs, duodenum, jejunum, ileum, cecum, distal colon, and proximal colon were all assayed for dopamine content using UHPLC-ECD as above.

For the 12-day trial 10 mice were placed in each group of control mice given feed plus the PBS gavage, a probiotic supplemented diet of normal feed plus a $1\times10^9$ CFU gavage of ML1082, and a synbiotic diet of feed with 1 mg/g supplemented pure L-DOPA and a $1\times10^9$ CFU gavage of ML1082. Behavioral testing was performed on days 11 and 12 (see below), followed by sacrifice and sample collection for UHPLC-ECD as above.

Mice were allowed to acclimate for 7 days, followed by treatments. For the treatments, mice were brought into the prep room from the housing rack and left to equilibrate for 15 minutes. The mice were then put into a scruffing restraint and gavaged with either PBS or ML1082 culture in PBS directly into the stomach using a silicone tipped needle. The mice were then monitored and allowed to equilibrate for 30 minutes, followed by return to the housing rack.

Fecal or cecal matter collected on day 7 for just the 7-day trial was cultured in sSIM with or without *Mucuna* powder supplement overnight, followed by UHPLC-ECD, as described above, to determine the amount of dopamine produced in the media.

Figure 10A:
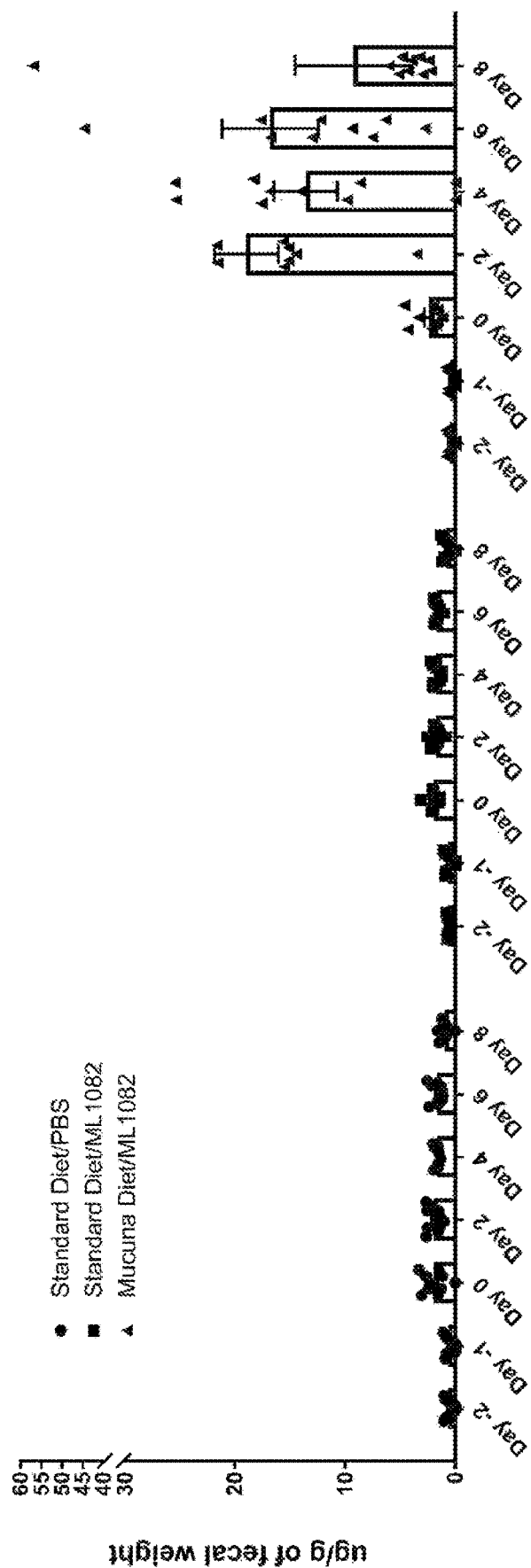
FIG. 10A is a graphical representation of the production of dopamine in feces of mice over time fed either a control diet consisting of a standard diet with PBS; a probiotic diet consisting of a standard diet supplemented with *E. faecium* strain ML1082; or a synbiotic diet consisting of a diet supplemented with *Mucuna* powder and *E. faecium* strain ML1082.
Figure 10B:
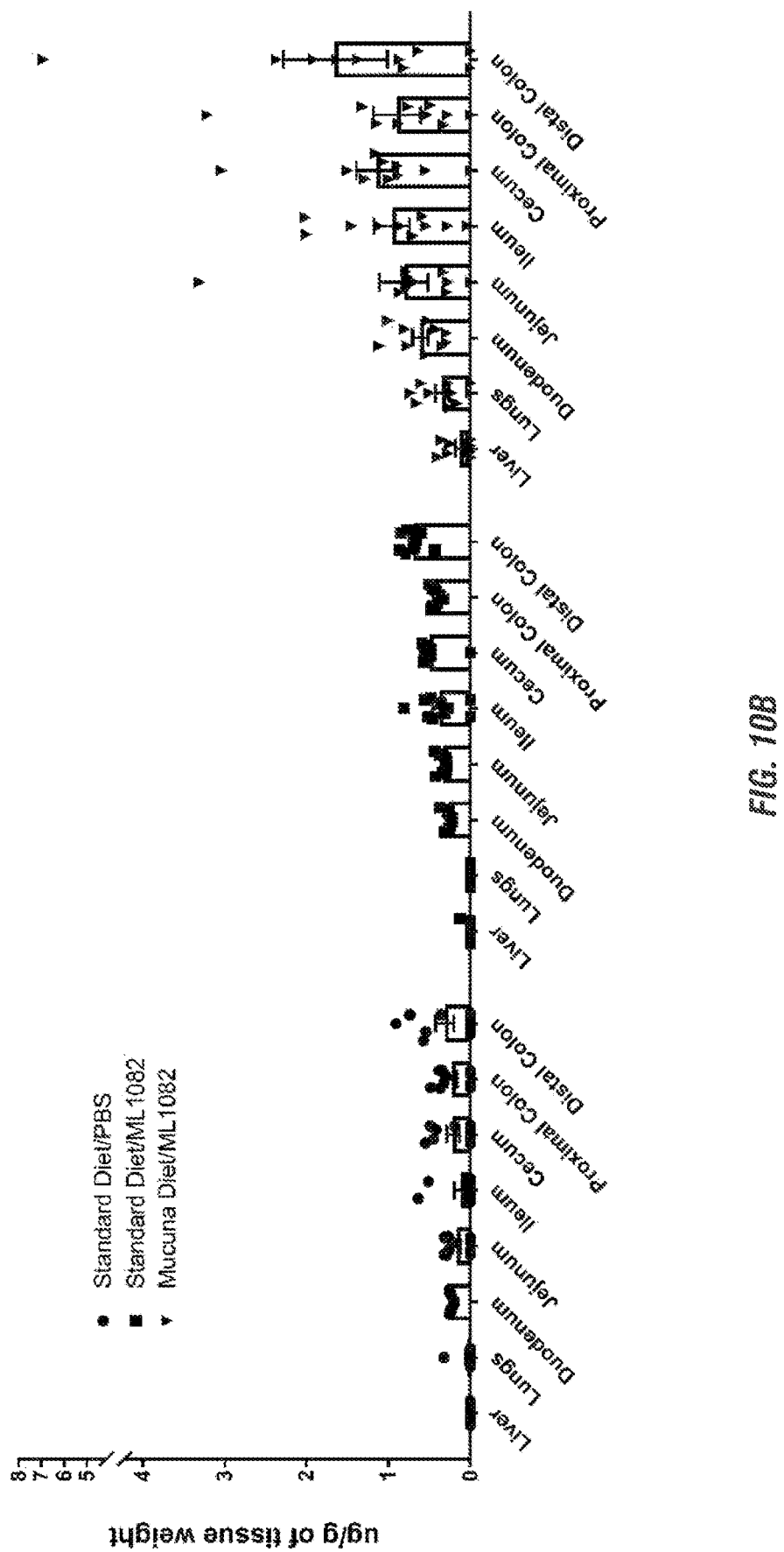
FIG. 10B is a graphical representation of the in vivo production of dopamine in mice fed either a control diet consisting of a standard diet with PBS; a probiotic diet consisting of a standard diet supplemented with *E. faecium* strain ML1082; or a synbiotic diet consisting of a diet supplemented with *Mucuna* powder and *E. faecium* strain ML1082 in various tissues.
Figure 10C:
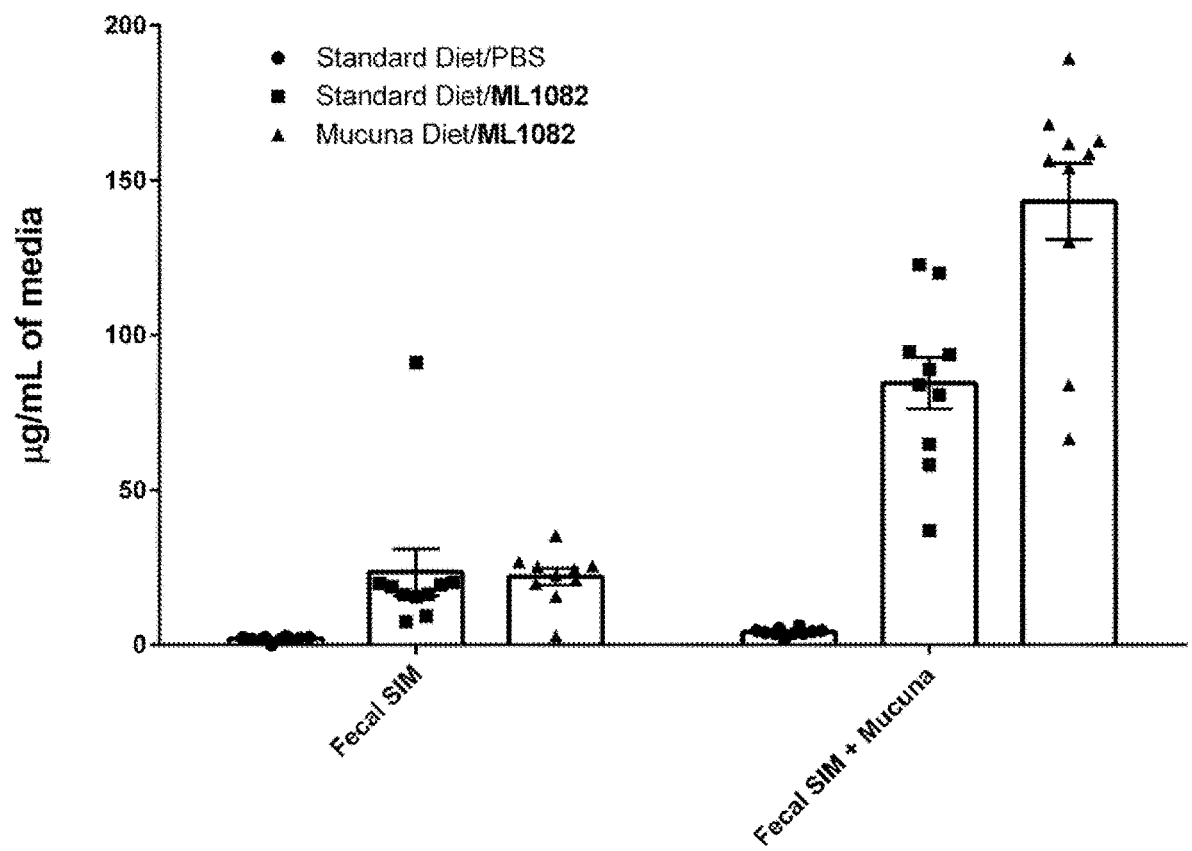
FIG. 10C is a graphical representation of production of dopamine in sSIM from extract cecal or fecal matter from mice fed either a control diet consisting of a standard diet with PBS; a probiotic diet consisting of a standard diet supplemented with *E. faecium* strain ML1082; or a synbiotic diet consisting of a diet supplemented with *Mucuna* powder and *E. faecium* strain ML1082.

As shown in FIG. 10A, mice fed the standard diet, or the standard diet supplemented with ML1082 did not show a large difference in dopamine production over time as measured in the collected fecal pellets. However, the synbiotic diet of ML1082 plus *Mucuna* powder supplemented feed resulted in a large increase in dopamine production as early as day 2. This elevated level was seen throughout the time course. Additionally, as show in FIG. 10B, in every organ but the liver, the synbiotic diet produced a larger increase in dopamine levels than the ML1082 supplemented diet alone. The ML1082 does show a slight increase in dopamine level compared to the controls in every tissue than the liver. The largest increase is seen in the distal colon of the synbiotic diet. Further, as shown in FIG. 10C, a higher amount of dopamine was found in the sSIM media of both the probiotic and synbiotic diets in the fecal samples when compared to the control diet. Further, when comparing sSIM media supplemented with additional *Mucuna* to unsupplemented media, the supplemented media produced an even greater amount of dopamine. Additionally, when comparing the probiotic diet to the synbiotic diet when the media is further supplemented with *Mucuna*, the cultures are able to produce an even greater amount of dopamine.

Without being bound to a particular theory, without additional supplementation, the cultures appear to utilize all available L-DOPA within the media overnight and the production of dopamine would be limited by the lower amount of L-DOPA present. Further, when supplemented with additional L-DOPA, the results indicate that not only can *E. faecium* reach the lower gut, but the synbiotic diet seems to further select for dopamine producing organisms than a probiotic diet alone in vivo.

For animals receiving the purified L-DOPA supplemented, the L-DOPA appeared to be absorbed into the body before it could interact with the probiotics (data not shown).

These results show that while a diet supplemented with a probiotic strain alone is capable of increasing the production of dopamine in the gut and throughout different tissues (FIG. 10B), a synbiotic of a high converting and producing probiotic strain of *E. faecium* and a diet supplemented with *Mucuna* powder produces a larger amount across nearly all tissues tested and at every day tested (FIG. 10A).

Further, the results show that the *Mucuna* powder prevents the L-DOPA being uptaken into the body before it is converted by the probiotic, unlike a supplement of pure L-DOPA. This difference indicates that a time release tablet or capsule may be used to target different portions of the gut. Due to the differences in innervation of the gut, this may be important to achieve desired effects, such as targeting the upper gut to effect mood, or the lower gut to help treat inflammation.

Figure 11A:
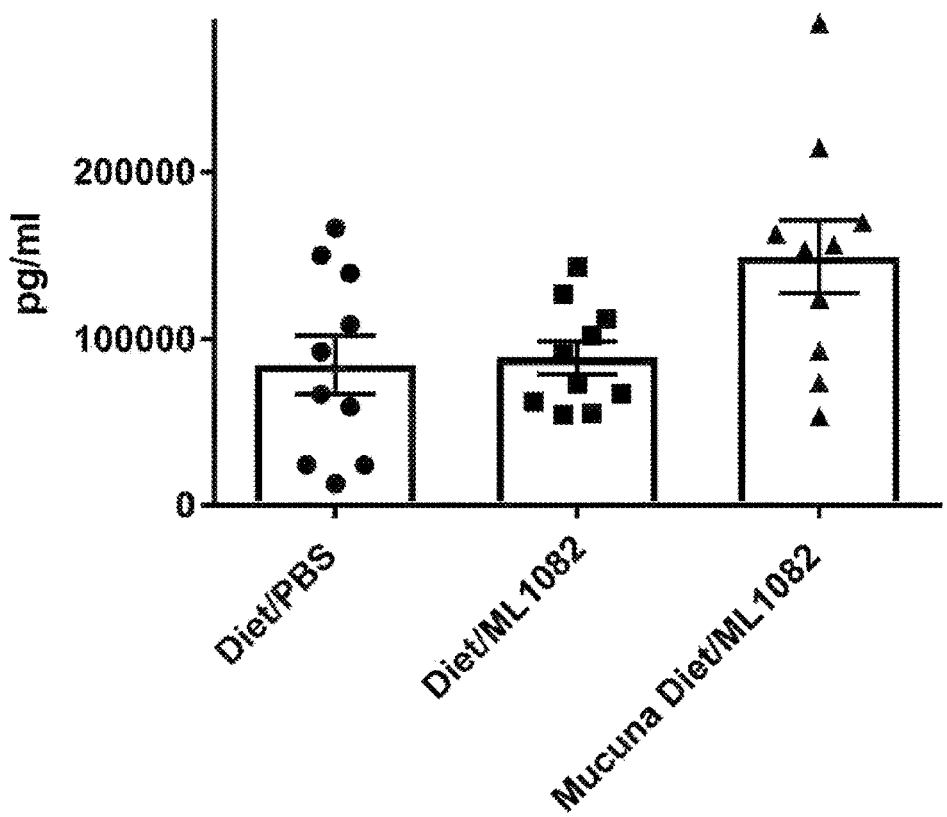
FIG. 11A is a graphical representation of corticosterone level in the serum on day 7 of the 7-day feeding trial.
Figure 11B:
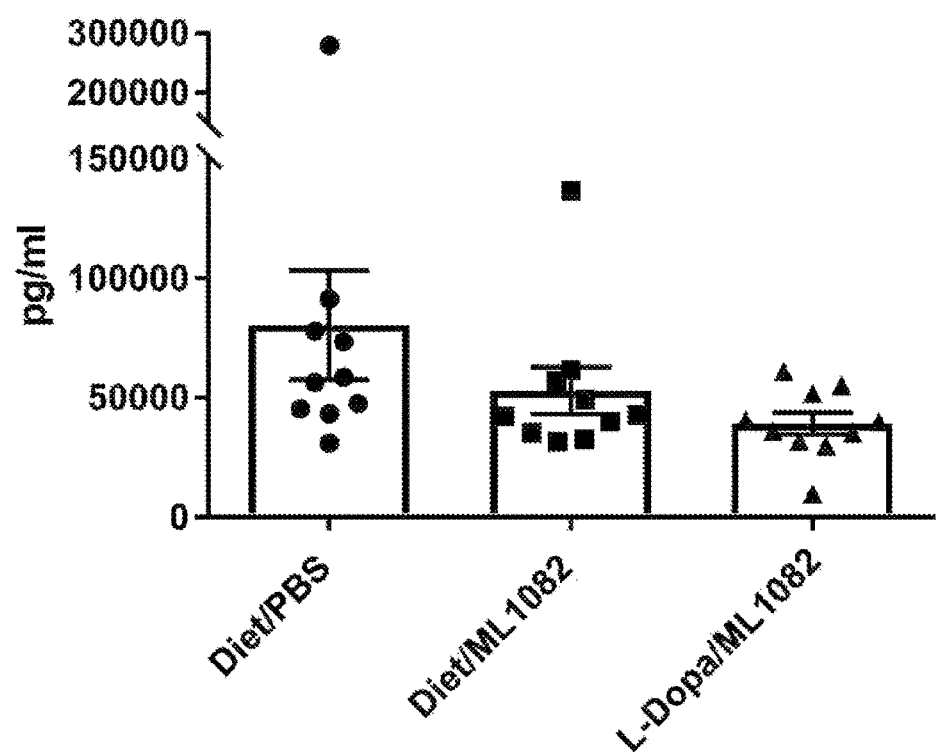
FIG. 11B is a graphical representation of corticosterone level in the serum on day 12 of the 12-day feeding trial.

This is further supported by the effect seen on corticosterone in the serum. Corticosterone levels in the synbiotic diets using the *Mucuna* powder on day 7 showed an increase in corticosterone, while the synbiotic diets using pure L-DOPA supplement showed a decrease in corticosterone on day 12 (see FIGS. 11A and 11B for day 7 and day 12, respectively). Without being limited to any particular theory, this may be due to the uptake of the pure L-DOPA being uptaken by the body and reducing stress levels in the body and the *Mucuna* powder prevents this early uptake and reduction in chronic stress.

Thus, depending on the delivery of the L-DOPA of a synbiotic diet, such as through a time-release tablet or capsule, it may be possible to target different regions of the alimentary tract to treat different conditions in a subject.

Example 13

Figure 12A:
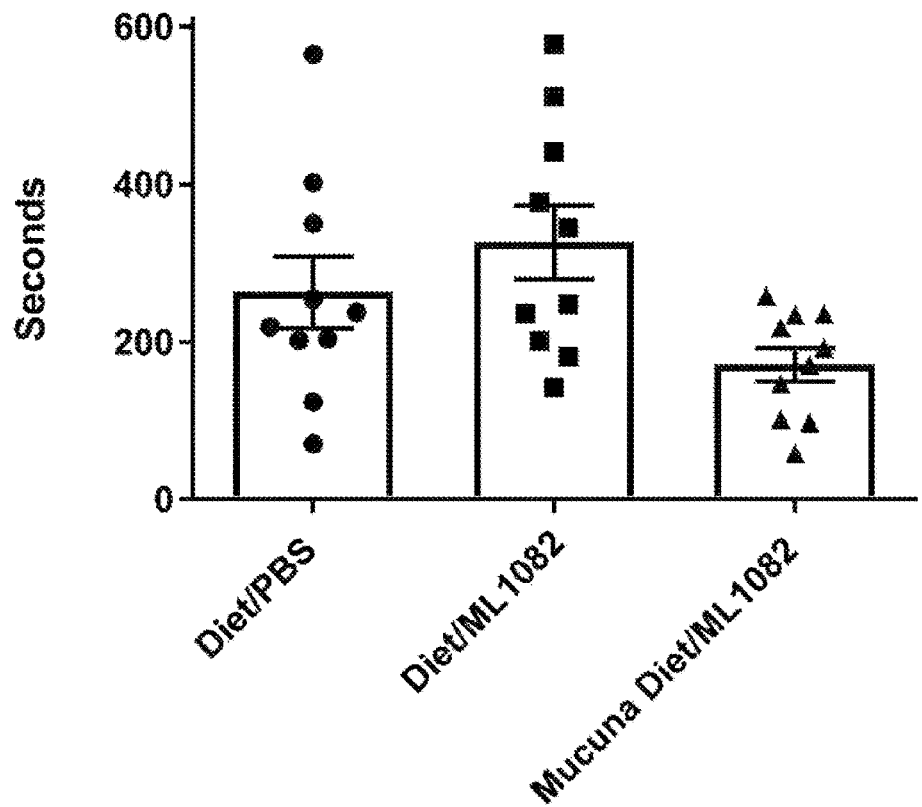
FIGS. 12A-K are graphical representations of behavioral traits in mice fed either a control diet of normal feed and PBS; normal feed supplemented with *E. faecium* strain ML1082; or a synbiotic diet of normal feed supplemented with *E. faecium* strain ML1082 plus *Mucuna* powder.
Figure 12B:
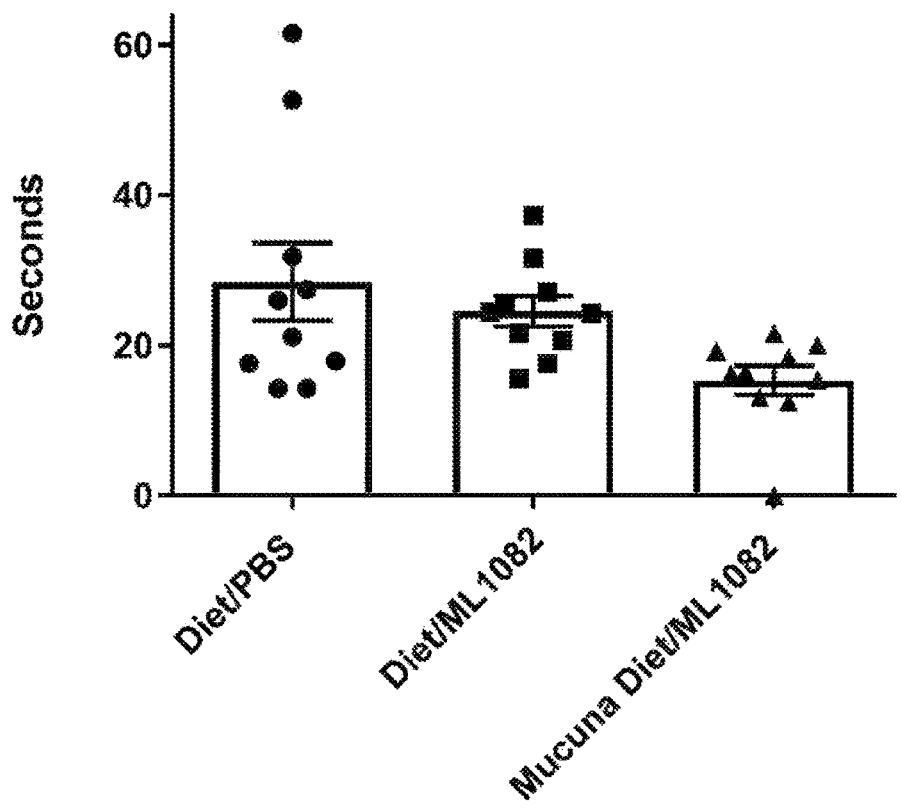
Figure 12C:
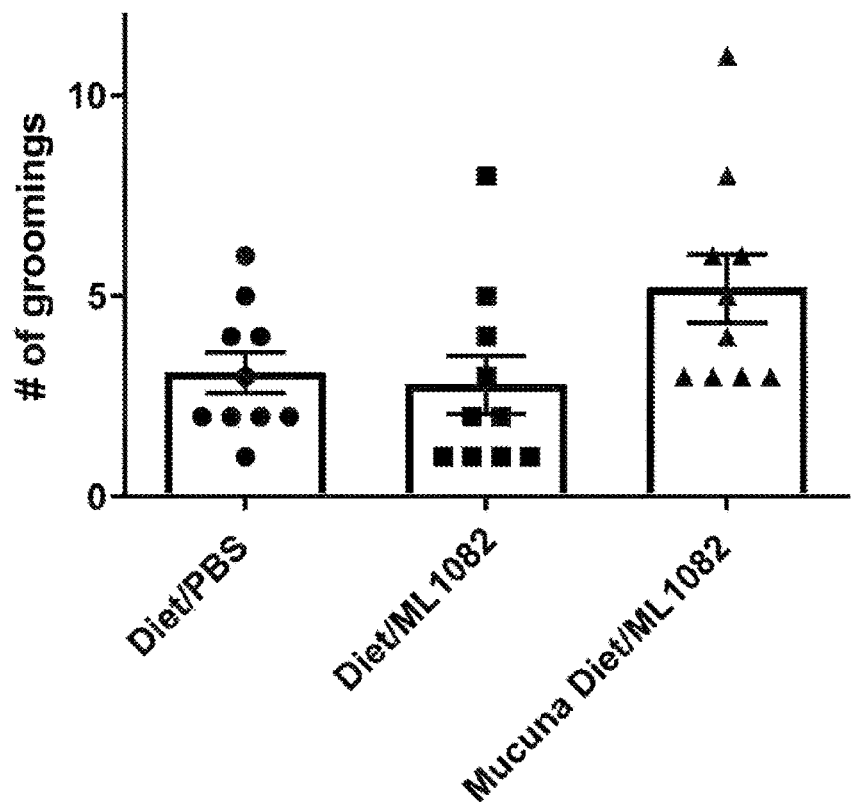
Figure 12D:
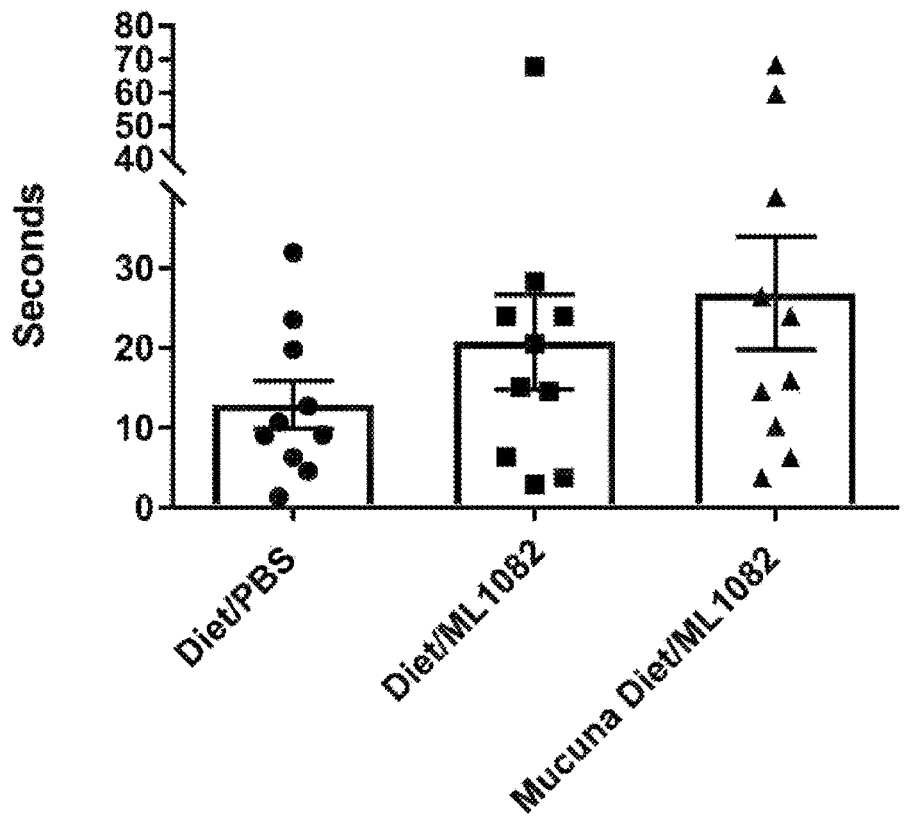
Figure 12E:
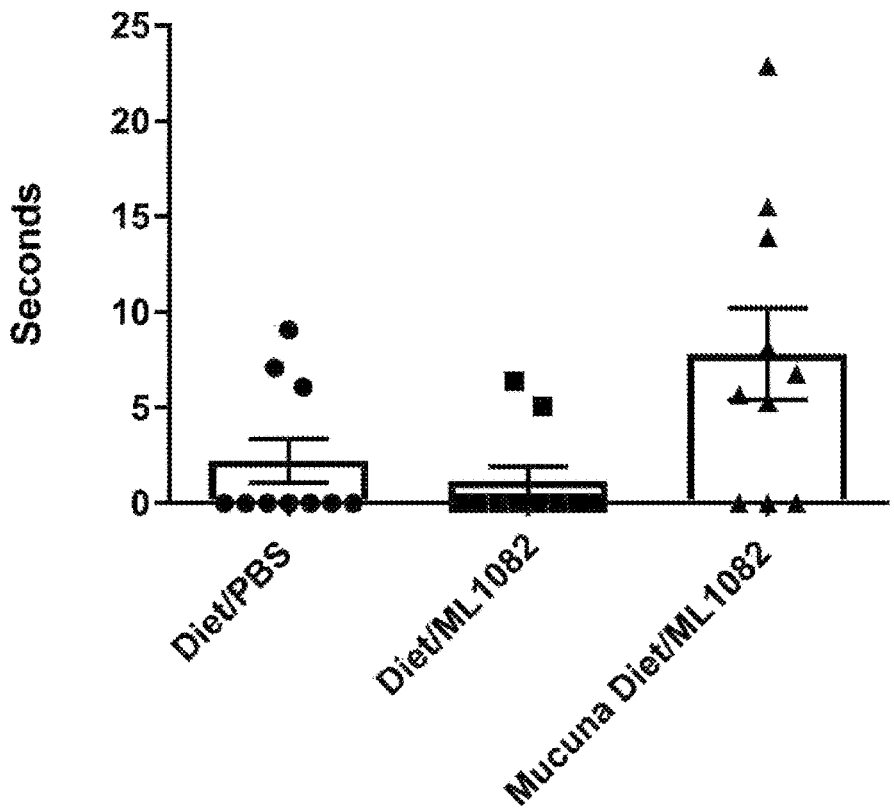
Figure 12F:
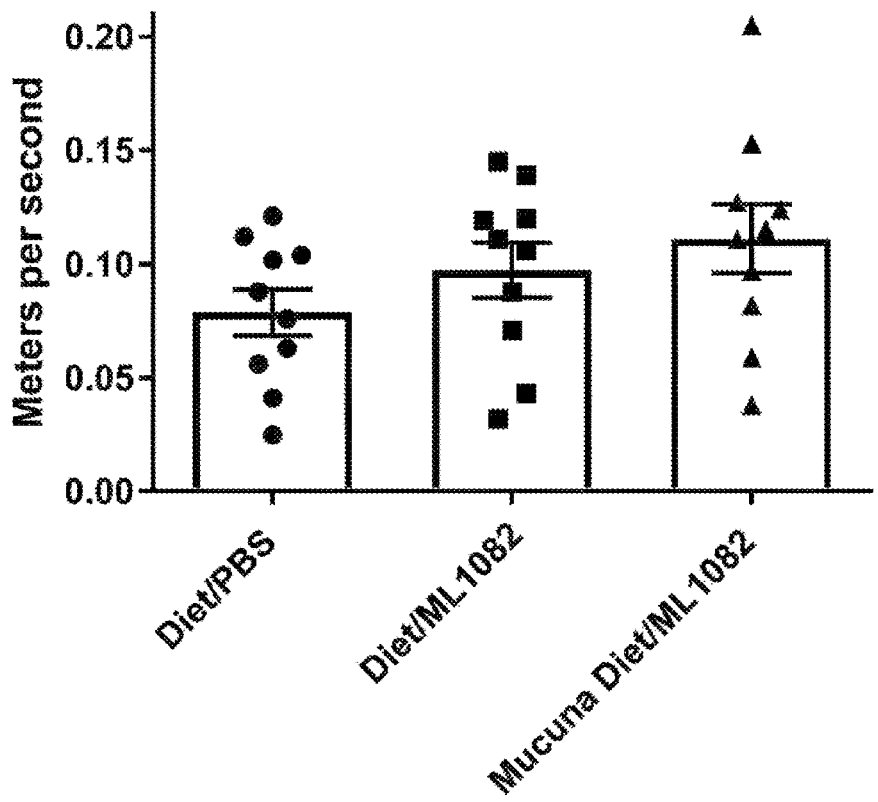
Figure 12G:
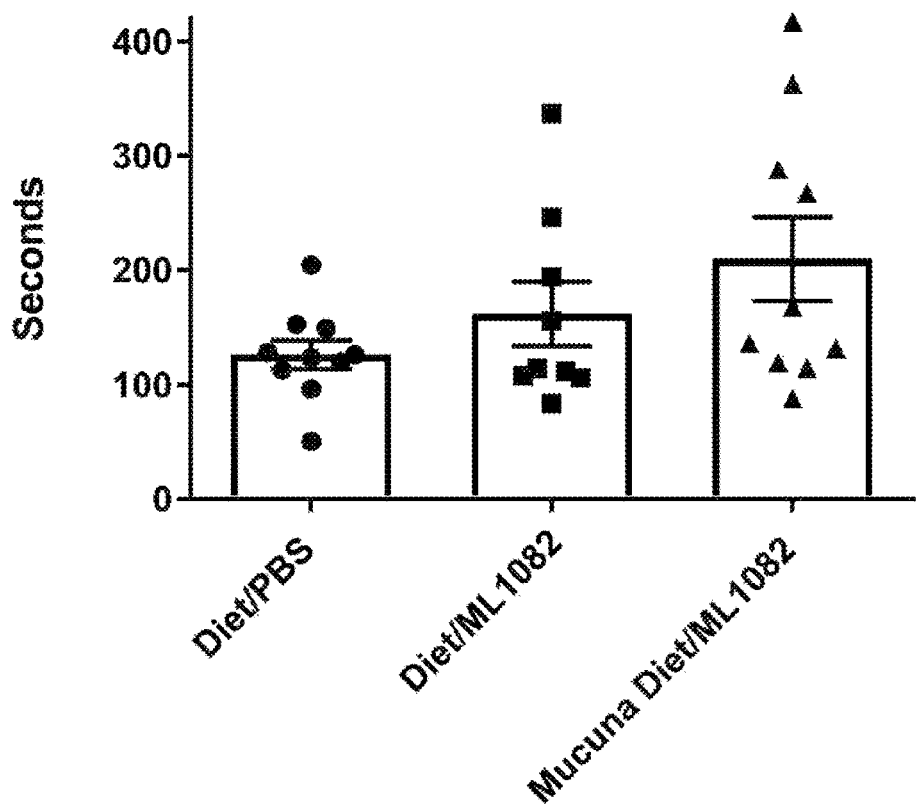
Figure 12H:
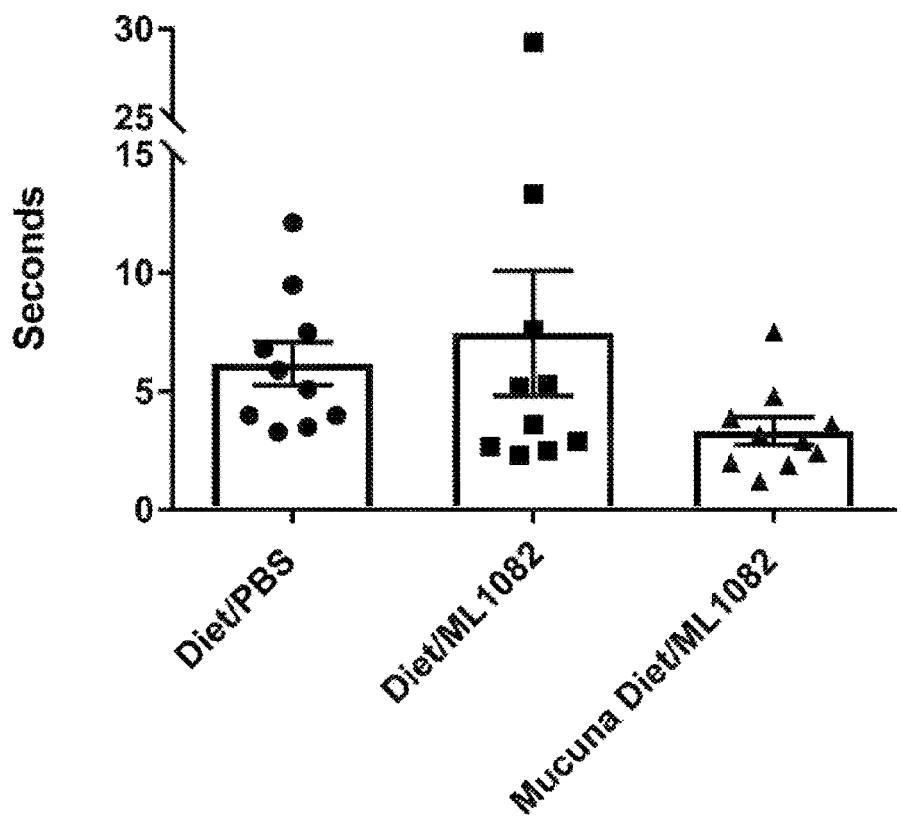
Figure 12I:
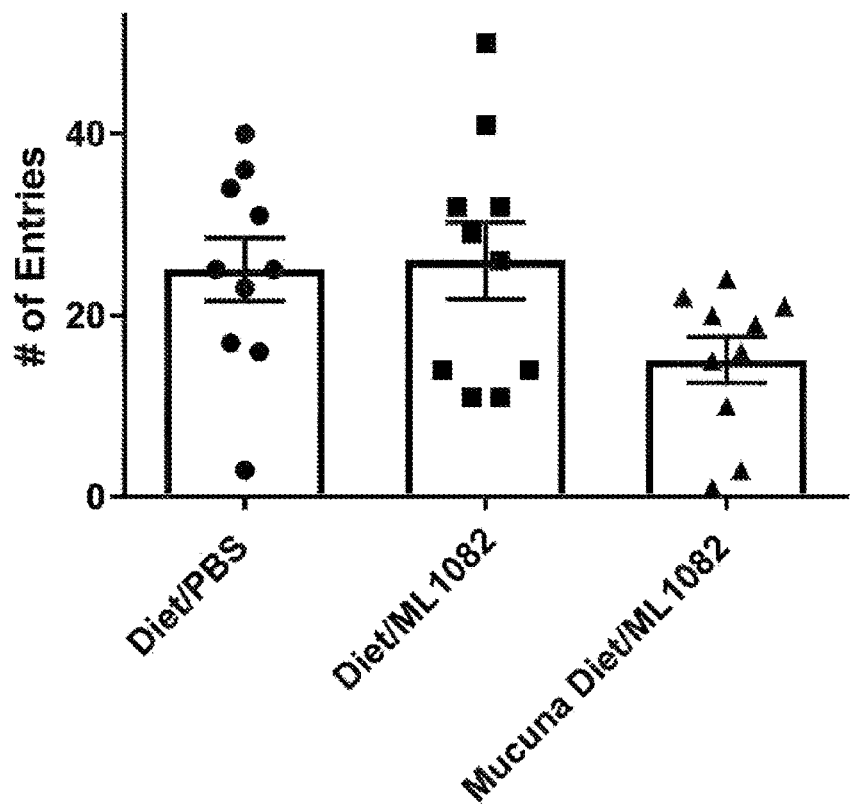
Figure 12J:
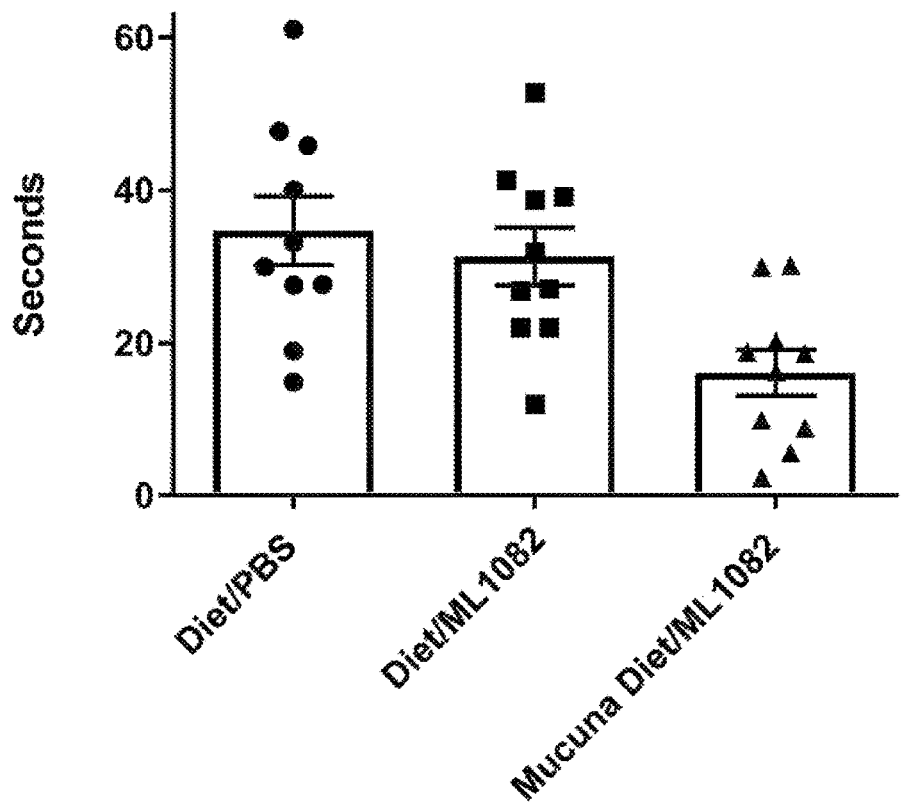
Figure 12K:
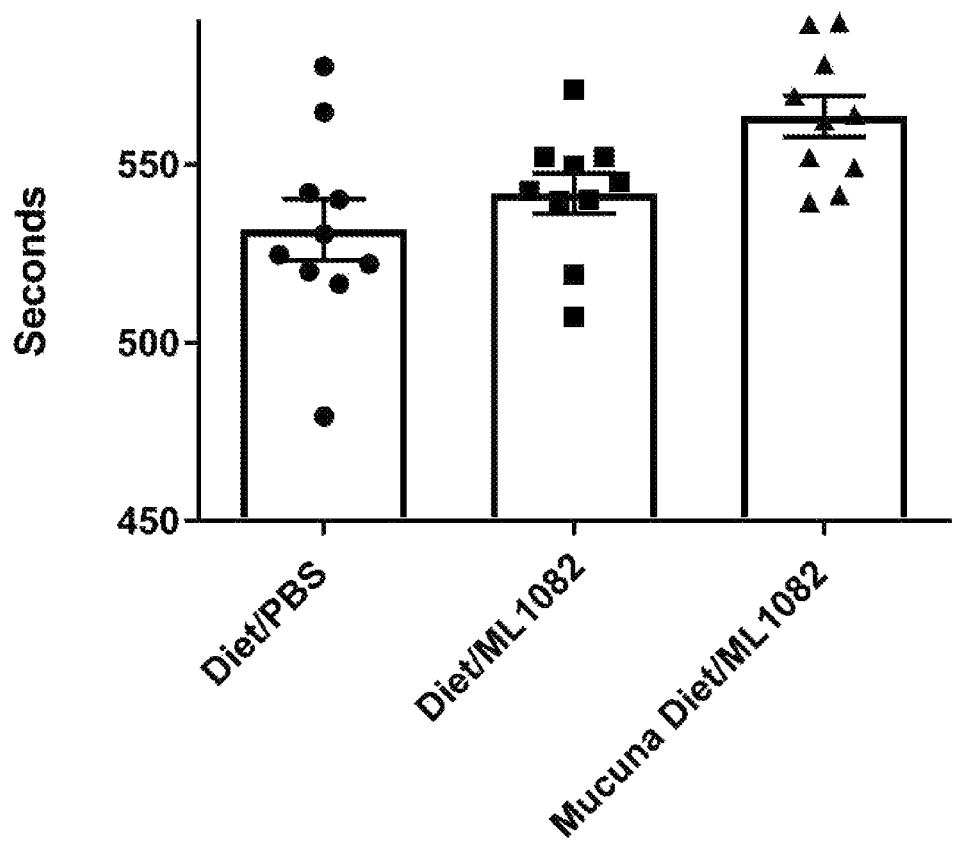
Figure 13A:
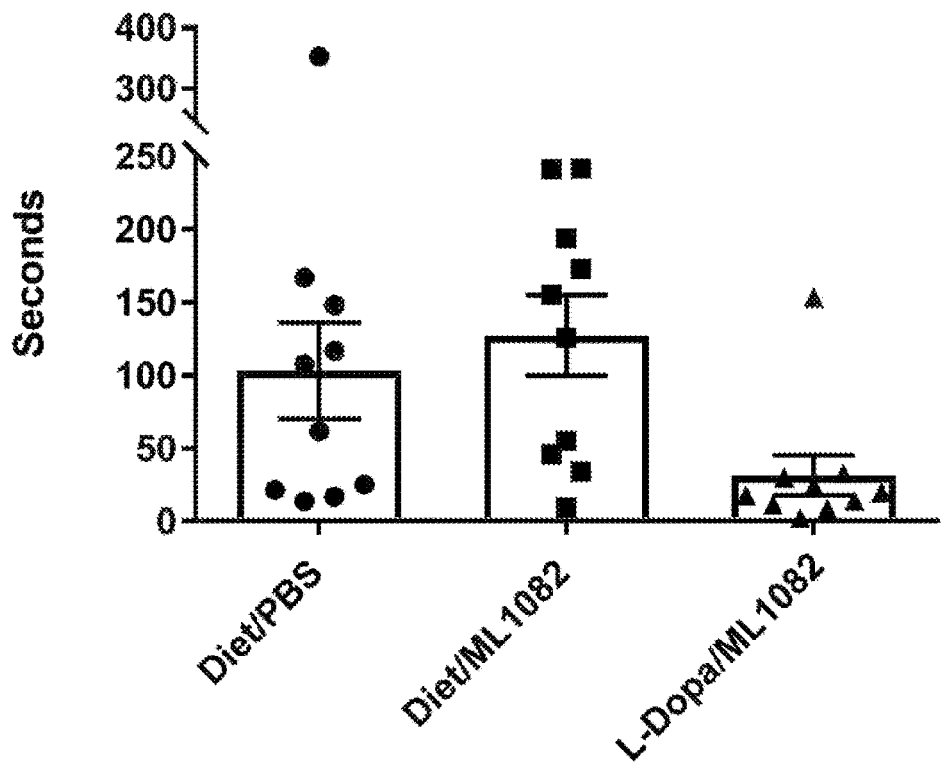
FIGS. 13A-C are graphical representations of behavioral measures of mice fed a control diet of normal feed supplemented with PBS; a probiotic diet of normal feed supplemented with *E. faecium*; or a synbiotic diet of a normal feed supplemented with *E. faecium* and purified L-DOPA.
Figure 13B:
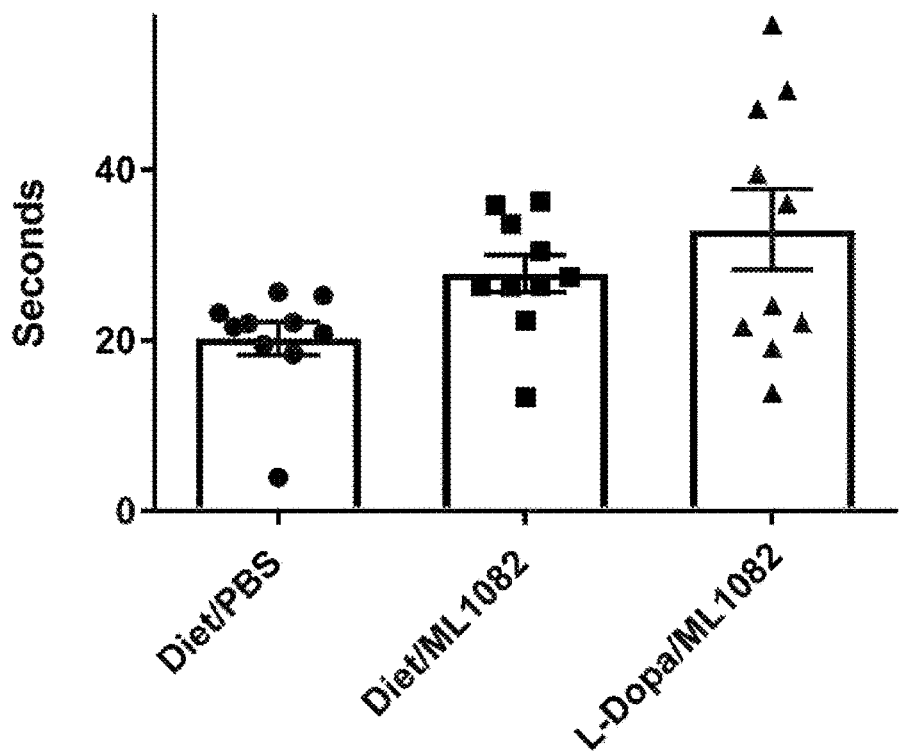
Figure 13C:
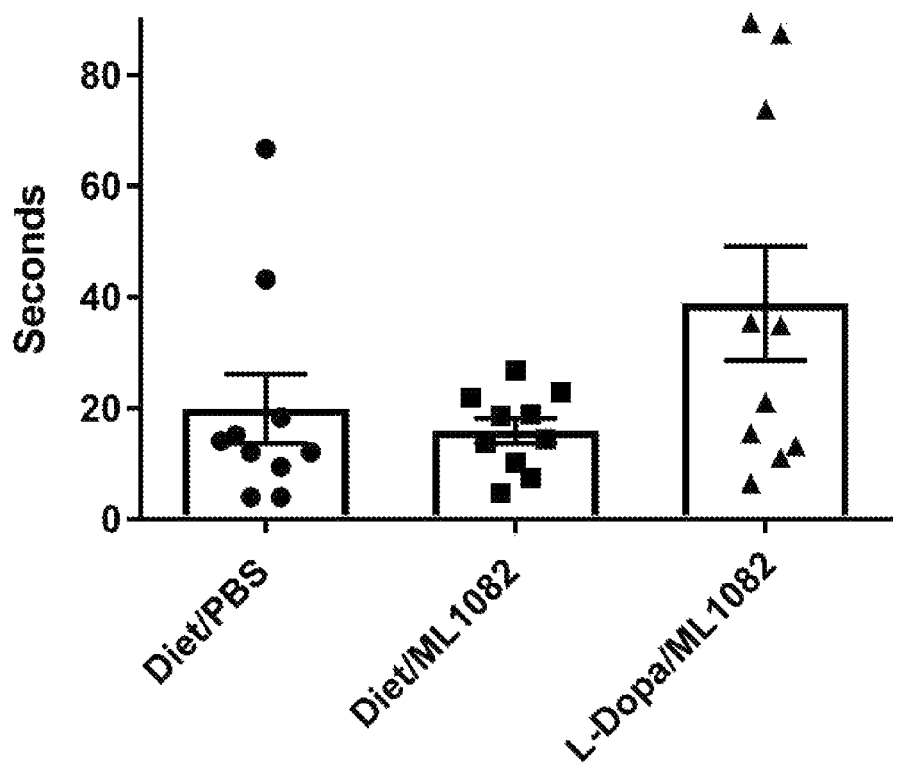

In addition to the in vivo production of dopamine, the 7-day and 12-day time courses were tested for behavioral changes. For the 7-day course, the mice were tested on an elevated plus maze on day 5 and an open field on day 7, using standard protocols (see Walf, A. A. and Frye, C. A., *The Use of the Elevated Plus Maze as an Assay of Anxiety-Related Behavior in Rodents*, Nature Protocols, 2007; 2:322-328; and Prut, L, and Belzung C., *The Open Field as a Paradigm to Measure the Effects of Drugs on Anxiety-like Behaviors: A Review*, European Journal of Pharmacology, 2003; 463:3-33, both incorporated herein by reference). For the 12-day course, the elevated plus maze was administered on day 11 and the open field was administered on day 12. Various measures of behavior were taken. For the 7-day trial on the elevated plus maze the latency to first grooming (FIG. 12A), longest visit to the open arms (FIG. 12B), number of grooming (FIG. 12C), total time spent grooming (FIG. 12D), and total time immobile (FIG. 12E) were accessed. For the 7-day trial on the open field the average speed in the center zone (FIG. 12F), the latency to first grooming (FIG. 12G), longest visit to center zone (FIG. 12H), number of entries to center zone (FIG. 12I), time spent in center zone (FIG. 12J), and the time spent in the periphery zone (FIG. 12K) were accessed. For the 12-day trial, only elevated plus maze was administered, with the latency to first entry into the open arms (FIG. 13A), the longest visit to open arms (FIG. 13B), and the total time spent grooming (FIG. 13C) was assessed.

As can be seen in FIGS. 12A-12K and 13A-13C, both sets of mice treated with a synbiotic diet showed changes to their behavior. The 7-day trial mice, in agreement with the elevated corticosterone levels, showed generally higher levels of stress, while the 12-day trial mice generally showed a lower level of stress. For example, while the longest visit to the open arms of the 7-day trial synbiotic group of mice (FIG. 12B) decreases in comparing to the probiotic and control mice, indicating the mice were more anxious by avoiding open spaces, the 12-day trial synbiotic group of mice (FIG. 13B) showed an increased time spent in the open arms compared to both the control and probiotic fed mice, indicating the mice were less anxious by exploring open areas.

Thus, the behavioral data further supports the use of time release tablets or capsules to fine tune treatments using synbiotic compositions.

What is claimed is:

1. A method for treating an animal, human, or fish subject with gut inflammation and/or need for gut health with a probiotic strain capable of producing neurochemicals in the gut of the animal, human, or fish subject, comprising:

administering to the animal, human, or fish subject a therapeutically effective amount of at least one probiotic strain and a precursor of the neurochemical, wherein the neurochemical comprises dopamine, and wherein the precursor of the neurochemical comprises L-DOPA.

2. The method of claim 1, further comprising:
administering to the subject a therapeutically effective amount of the precursor of the neurochemical, wherein the neurochemical is in need of production in the gut of the subject, wherein the probiotic strain and the precursor of the neurochemical are administered orally to the subject.

3. The method of claim 1, wherein the therapeutically effective amount of the probiotic strain(s) is from about ($10^4$ CFU/kg feed) to about ($10^{12}$ CFU/kg feed).

4. The method of claim 1, wherein said probiotic strain is a probiotic bacterial strain, wherein the precursor of the neurochemical is L-DOPA, and wherein the therapeutically effective amount of L-DOPA is from about (0.01 kg L-DOPA/metric ton feed) to about (30 kg L-DOPA/metric ton feed).

5. The method of claim 4, wherein said probiotic bacterial strain is an *Enterococcus* spp. or a *Vagococcus* spp.

6. The method of claim 2, wherein the therapeutically effective amount of the precursor of the neurochemical is from about (1 mg/kg animal) to about (10 mg/kg animal).

7. The method of claim 2, wherein said neurochemical is dopamine, wherein the precursor of the neurochemical is L-DOPA, and wherein a co-factor for the production of dopamine is pyridoxal phosphate.

8. The method of claim 2, wherein the probiotic strain and precursor of the neurochemical are co-administered in a single delivery system, and wherein the single delivery system comprises a co-formulation of the probiotic strain and the precursor of the neurochemical and/or a co-packaged formulation of the probiotic strain and the precursor of the neurochemical.

9. The method of claim 2, wherein the probiotic strain and precursor of the neurochemical are co-administered in distinct or separate delivery systems.

10. The method of claim 2, wherein the probiotic strain and precursor of the neurochemical are separately administered in sequence, and wherein the probiotic strain is administered first and thereafter the precursor of the neurochemical is administered second, or wherein the precursor of the neurochemical is administered first and thereafter the probiotic strain is administered second.

11. The method of claim 1, the method further comprising a food source that is an herbal, plant source, or fermentation product and wherein the precursor of the neurochemical is L-DOPA.

12. The method of claim 1, wherein the subject's behavior is changed.

* * * * *